US009453209B2

(12) United States Patent
Andrews et al.

(10) Patent No.: US 9,453,209 B2
(45) Date of Patent: Sep. 27, 2016

(54) ENHANCING HEALTH IN MAMMALS USING TELOMERASE REVERSE TRANSCRIPTASE GENE THERAPY

(71) Applicant: Sierra Sciences, LLC, Reno, NV (US)

(72) Inventors: William H. Andrews, Reno, NV (US); Lancer K. Brown, Sparks, NV (US); Hamid Mohammadpour, Reno, NV (US); Laura A. Briggs, Reno, NV (US)

(73) Assignee: Sierra Sciences, LLC, Reno, NV (US)

( * ) Notice: Subject to any disclaimer, the term of this patent is extended or adjusted under 35 U.S.C. 154(b) by 0 days.

(21) Appl. No.: 14/655,140

(22) PCT Filed: Dec. 23, 2013

(86) PCT No.: PCT/US2013/077619
§ 371 (c)(1),
(2) Date: Jun. 24, 2015

(87) PCT Pub. No.: WO2014/105870
PCT Pub. Date: Jul. 3, 2014

(65) Prior Publication Data

US 2015/0322416 A1 Nov. 12, 2015

Related U.S. Application Data

(60) Provisional application No. 61/746,438, filed on Dec. 27, 2012.

(51) Int. Cl.

| | |
|---|---|
| ***A61K 48/00*** | (2006.01) |
| ***C12N 9/12*** | (2006.01) |
| ***C12N 7/00*** | (2006.01) |
| *A61K 38/00* | (2006.01) |

(52) U.S. Cl.
CPC ............ *C12N 9/1276* (2013.01); *A61K 48/00* (2013.01); *A61K 48/005* (2013.01); *C12N 7/00* (2013.01); *A61K 38/00* (2013.01); *C12N 2710/10341* (2013.01); *C12N 2740/15041* (2013.01); *C12Y 207/07049* (2013.01)

(58) Field of Classification Search
None
See application file for complete search history.

(56) References Cited

U.S. PATENT DOCUMENTS 6,475,789 B1 * 11/2002 Cech .................... C12N 9/1241 424/94.1
2009/0175892 A1 * 7/2009 Langlade-Demoyen A61K 39/0011 424/185.1

FOREIGN PATENT DOCUMENTS

| | | | |
|---|---|---|---|
| WO | WO0216555 | A2 | 2/2002 |
| WO | WO0216657 | A1 | 2/2002 |
| WO | WO0216658 | A1 | 2/2002 |
| WO | WO02070668 | A2 | 9/2002 |
| WO | WO02072787 | A2 | 9/2002 |
| WO | WO02090570 | A2 | 11/2002 |
| WO | WO02090571 | A2 | 11/2002 |
| WO | WO02101010 | A2 | 12/2002 |
| WO | WO03000916 | A2 | 1/2003 |
| WO | WO03016474 | A2 | 2/2003 |
| WO | WO03034985 | A2 | 5/2003 |
| WO | WO2012001170 | A1 | 1/2012 |

OTHER PUBLICATIONS

Yamaguchi et al. (New Engl J Med 352:1413-1424.*
Sinn et al. (Gene Therapy 2005, 1089-1098).*
Cristofari et al., Telomere length homeostasis requires that telomerase levels are limiting, The EMBO Journal (2006) 25:565-574.
De Jesus et al., Telomerase gene therapy in adult and old mice delays aging and increases longevity without increasing cancer, EMBO Mol Med (2012) 4(8): 691-704.
Vidale et al., The catalytic and the RNA subunits of human telomerase are required to immortalize equid primary fibroblasts, Chromosoma (2012) 121:475-488.

* cited by examiner

*Primary Examiner* — Kimberly Chong
(74) *Attorney, Agent, or Firm* — Bret E. Field; Glenn J. Foulds; Bozicevic, Field & Francis LLP

(57) ABSTRACT

Methods of treating an age-related disorder in a subject are provided. Aspects of the methods include administering to the subject a nucleic acid vector including a coding sequence for telomerase reverse transcriptase (TERT) and/or telomerase RNA (TR). Gene therapy methods are also provided. Aspects of the invention further include compositions, e.g., nucleic acid vectors and kits, etc., that find use in methods of the invention.

19 Claims, 7 Drawing Sheets

SEQUENCE LISTING

```
<160> NUMBER OF SEQ ID NOS: 3

<210> SEQ ID NO 1
<211> LENGTH: 38420
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (2450)..(2450)
<223> OTHER INFORMATION: n is a, c, g, or t

<400> SEQUENCE: 1

tcacagaacc ctagtattca acctgccacc tccctcccaa cacacagagt acacagtcct     60

ttctccccgg ctggccttaa aaagcatcat atcatgggta acagacatat tcttaggtgt    120

tatattccac acggtttcct gtcgagccaa acgctcatca agtgatatta ataaactccc    180

cgggcagctc acttaagttc atgtcgctgt ccagctgctg agccacaggc tgctgtccaa    240

cttgcggttg cttaacgggc ggcgaaggag aagtccacgc ctacatgggg ggagagtcat    300

aatcgtgcat caggataggg cggtggtgct gcagcagcgc gcgaataaac tgctgccgcc    360

gccgctccgt cctgcaggaa tacaacatgg cagtggtctc ctcagcgatg attcgcaccg    420

cccgcagcat aaggcgcttg tcctccgggc acagcagcgc accctgatct cacttaaatc    480

agcacagtaa ctgcagcaca gcaccacaat attgttcaaa atcccacagt gcaaggcgct    540

gtatccaaag ctcatggcgg ggaccacaga acccacgtgg ccatcatacc acaagcgcag    600

gtagattaag tggcgacccc tcataaacac gctggacata aacattacct cttttggcat    660

gttgtaattc accacctccc ggtaccatat aaacctctga ttaaacatgg cgccatccac    720

caccatccta aaccagctgg ccaaaacctg ccccgccggg ntatacactg cagggaaccg    780

ggacttggac aatgacaagt gggagagccc aggactcgta accatggatc atcatgctcg    840

tcatgatatc aatgttggca caacacaggc acacgtgcat acacttcctc aggattacaa    900

gctcctcccg cgttagaacc atatcccagg gaacaaccca ttcctgaatc agcgtaaatc    960

ccacactgca gggaagacct cgcacgtaac tcacgttgtg cattgtcaaa gtgttacatt   1020

cgggcagcag cggatgatcc tccagtatgg tagcgcgggt ttctgtctca aaaggaggta   1080

gacgatccct actgtacgga gtgcgccgag acaaccgaga tcgtgttggt cgtagtgtca   1140

tgccaaatgg aacgccggac gtagtcatat ttcctgaagc aaaaccaggt gcgggcgtga   1200

caaacagatc tgcgtctccg gtctcgccgc ttagatcgct ctgtgtagta gttgtagtat   1260

atccactctc tcaaagcatc caggcgcccc ctggcttcgg gttctatgta aactccttca   1320

tgcgccgctg ccctgataac atccaccacc gcagaataag ccacacccag ccaacctaca   1380

cattcgttct gcgagtcaca cacgggagga gcgggaagag ctggaagaac catgtttttt   1440

tttttattcc aaaagattat ccaaaacctc aaaatgaaga tctattaagt gaacgcgctc   1500

ccctccggtg gcgtggtcaa actctacagc caaagaacag ataatggcat ttgtaagatg   1560

ttgcacaatg gcttccaaaa ggcaaacggc cctcacgtcc aagtggacgt aaaggctaaa   1620
```

```
cccttcaggg tgaatctcct ctataaacat tccagcacct tcaaccatgc ccaaataatt   1680
ctcatctcgc caccttctca atatatctct aagcaaatcc cgaatattta agtccgggcc   1740
attgtaaaaa atttggctcc agagcgccct ccaccttcag cctcaagcag cgaatcatga   1800
ttgcaaaaat tcaggttcct cacagacctg tataagattc aaaagcggaa cattaacaaa   1860
aataccgcga tcccgtaggt cccttcgcag ggccagctga acataatcgt gcaggtctgc   1920
acggaccagc gcggccactt ccccgccagg aaccatgaca aaagaaccca cactgattat   1980
gacacgcata ctcggagcta tgctaaccag cgtagccccg atgtaagctt gttgcatggg   2040
cggcgatata aaatgcaagg tgctgctcaa aaaatcaggc aaagcctcgc gcaaaaaaga   2100
aagcacatcg tagtcatgct catgcagata aaggcaggta agctccggaa ccaccacaga   2160
aaaagacacc atttttctct caaacatgtc tgcgggtttc tgcataaaca caaaataaaa   2220
taacaaaaaa acatttaaac attagaagcc tgtcttacaa caggaaaaac aacccttata   2280
agcataagac ggactacggc catgccggcg tgaccgtaaa aaaactggtc accgtgatta   2340
aaaagcacca ccgacagctc ctcggtcagt ccggagtcat aatgtaagac tcggtaaaca   2400
catcaggttg attcacatcg gtcagtgtta aaaagcgacc gaaatagccn gggggaatac   2460
aatacccgca ggcgtagaga caacattaca gcccccatag gaggtataac aaaattaata   2520
ggagagaaaa acacataaac acctgaaaaa ccctcctgcc taggcaaaat agcaccctcc   2580
cgctccagaa caacatacag cgcttccaca gcggcagcca taacagtcag ccttaccagt   2640
aaaaaagaaa acctattaaa aaaacaccac tcgacacggc accagctcaa tcagtcacag   2700
tgtaaaaaag ggccaagtgc agagcgagta tatataggac taaaaaatga cggtaacggt   2760
taaagtccac aaaaaacacc cagaaaaccg cacgcgaacc tacgcccaga aacgaaagcc   2820
aaaaaaccca caacttcctc aaatcgtcac ttccgttttc ccacgttacg tcacttccca   2880
ttttaagaaa actacaattc ccaacacata caagttactc cgccctaaaa cctacgtcac   2940
ccgccccgtt cccacgcccc gcgccacgtc acaaactcca ccccctcatt atcatattgg   3000
cttcaatcca aaataaggta tattattgat gatgttaatt aacatgcatg gatccatatg   3060
cggtgtgaaa taccgcacag atgcgtaagg agaaaatacc gcatcaggcg ctcttccgct   3120
tcctcgctca ctgactcgct gcgctcggtc gttcggctgc ggcgagcggt atcagctcac   3180
tcaaaggcgg taatacggtt atccacagaa tcaggggata acgcaggaaa gaacatgtga   3240
gcaaaaggcc agcaaaaggc caggaaccgt aaaaaggccg cgttgctggc gtttttccat   3300
aggctccgcc cccctgacga gcatcacaaa aatcgacgct caagtcagag gtggcgaaac   3360
ccgacaggac tataaagata ccaggcgttt ccccctggaa gctccctcgt gcgctctcct   3420
gttccgaccc tgccgcttac cggatacctg tccgcctttc tcccttcggg aagcgtggcg   3480
ctttctcata gctcacgctg taggtatctc agttcggtgt aggtcgttcg ctccaagctg   3540
ggctgtgtgc acgaaccccc cgttcagccc gaccgctgcg ccttatccgg taactatcgt   3600
cttgagtcca acccggtaag acacgactta tcgccactgg cagcagccac tggtaacagg   3660
attagcagag cgaggtatgt aggcggtgct acagagttct tgaagtggtg gcctaactac   3720
ggctacacta gaaggacagt atttggtatc tgcgctctgc tgaagccagt taccttcgga   3780
aaaagagttg gtagctcttg atccggcaaa caaaccaccg ctggtagcgg tggttttttt   3840
gtttgcaagc agcagattac gcgcagaaaa aaaggatctc aagaagatcc tttgatcttt   3900
tctacggggt ctgacgctca gtggaacgaa aactcacgtt aagggatttt ggtcatgaga   3960
ttatcaaaaa ggatcttcac ctagatcctt ttaaattaaa aatgaagttt taaatcaatc   4020
```

```
taaagtatat atgagtaaac ttggtctgac agttaccaat gcttaatcag tgaggcacct   4080
atctcagcga tctgtctatt tcgttcatcc atagttgcct gactccccgt cgtgtagata   4140
actacgatac gggagggctt accatctggc cccagtgctg caatgatacc gcgagaccca   4200
cgctcaccgg ctccagattt atcagcaata aaccagccag ccggaagggc cgagcgcaga   4260
agtggtcctg caactttatc cgcctccatc cagtctatta attgttgccg ggaagctaga   4320
gtaagtagtt cgccagttaa tagtttgcgc aacgttgttg ccattgctgc agccatgaga   4380
ttatcaaaaa ggatcttcac ctagatcctt ttcacgtaga aagccagtcc gcagaaacgg   4440
tgctgacccc ggatgaatgt cagctactgg gctatctgga caagggaaaa cgcaagcgca   4500
aagagaaagc aggtagcttg cagtgggctt acatggcgat agctagactg ggcggtttta   4560
tggacagcaa gcgaaccgga attgccagct ggggcgccct ctggtaaggt tgggaagccc   4620
tgcaaagtaa actggatggc tttcttgccg ccaaggatct gatggcgcag gggatcaagc   4680
tctgatcaag agacaggatg aggatcgttt cgcatgattg aacaagatgg attgcacgca   4740
ggttctccgg ccgcttgggt ggagaggcta ttcggctatg actgggcaca acagacaatc   4800
ggctgctctg atgccgccgt gttccggctg tcagcgcagg ggcgcccggt tctttttgtc   4860
aagaccgacc tgtccggtgc cctgaatgaa ctgcaagacg aggcagcgcg gctatcgtgg   4920
ctggccacga cgggcgttcc ttgcgcagct gtgctcgacg ttgtcactga agcgggaagg   4980
gactggctgc tattgggcga agtgccgggg caggatctcc tgtcatctca ccttgctcct   5040
gccgagaaag tatccatcat ggctgatgca atgcggcggc tgcatacgct tgatccggct   5100
acctgcccat tcgaccacca agcgaaacat cgcatcgagc gagcacgtac tcggatggaa   5160
gccggtcttg tcgatcagga tgatctggac gaagagcatc aggggctcgc gccagccgaa   5220
ctgttcgcca ggctcaaggc gagcatgccc gacggcgagg atctcgtcgt gacccatggc   5280
gatgcctgct tgccgaatat catggtggaa aatggccgct tttctggatt catcgactgt   5340
ggccggctgg gtgtggcgga ccgctatcag gacatagcgt tggctacccg tgatattgct   5400
gaagagcttg gcggcgaatg ggctgaccgc ttcctcgtgc tttacggtat cgccgctccc   5460
gattcgcagc gcatcgcctt ctatcgcctt cttgacgagt tcttctgaat tttgttaaaa   5520
tttttgttaa atcagctcat tttttaacca ataggccgaa atcggcaaca tcccttataa   5580
atcaaaagaa tagaccgcga tagggttgag tgttgttcca gtttggaaca agagtccact   5640
attaaagaac gtggactcca acgtcaaagg gcgaaaaacc gtctatcagg gcgatggccc   5700
actacgtgaa ccatcaccca aatcaagttt tttgcggtcg aggtgccgta aagctctaaa   5760
tcggaaccct aaagggagcc cccgatttag agcttgacgg ggaaagccgg cgaacgtggc   5820
gagaaaggaa gggaagaaag cgaaaggagc gggcgctagg gcgctggcaa gtgtagcggt   5880
cacgctgcgc gtaaccacca cacccgcgcg cttaatgcgc cgctacaggg cgcgtccatt   5940
cgccattcag gatcgaatta attcttaatt aacatcatca ataatatacc ttattttgga   6000
ttgaagccaa tatgataatg agggggtgga gtttgtgacg tggcgcgggg cgtgggaacg   6060
gggcgggtga cgtagtagtg tggcggaagt gtgatgttgc aagtgtggcg gaacacatgt   6120
aagcgacgga tgtggcaaaa gtgacgtttt tggtgtgcgc cggtgtacac aggaagtgac   6180
aattttcgcg cggttttagg cggatgttgt agtaaatttg ggcgtaaccg agtaagattt   6240
ggccattttc gcgggaaaac tgaataagag gaagtgaaat ctgaataatt ttgtgttact   6300
catagcgcgt aatactggta ccgcggccgc ctcgagtcta gagatatcga attcaagctt   6360
```

```
aaggtgcacg gcccacgtgg ccactagtaa tttttctgca gaaaacgtac ccggggatcc   6420
tctaggatcc caccgaaagg ttgctcctta acacaggcta aggaccagct tctttgggag   6480
agaacagacg caggggcggg agggaaaaag ggagaggcag acgtcacttc cccttggcgg   6540
ctctggcagc agattggtcg gttgagtggc agaaaggcag acggggactg ggcaaggcac   6600
tgtcggtgac atcacggaca gggcgacttc tatgtagatg aggcagcgca gaggctgctg   6660
cttcgccact tgctgcttcg ccacgaagga gttcccgtgc cctgggagcg ggttcaggac   6720
cgcggatcgg aagtgagaat cccagctgtg tgtcagggct ggaaagggct cgggagtgcg   6780
cggggcaagt gaccgtgtgt gtaaagagtg aggcgtatga ggctgtgtcg gggcagagcc   6840
cgaagatccg ggttgcggag ggtgggcctg ggaggggtgg tggccatttt ttgtctaacc   6900
ctaactgaga agggcgtagg cgccgtgctt ttgctccccg cgcgctgttt ttctcgctga   6960
ctttcagcgg gcggaaaagc ctcggcctgc cgccttccac cgttcattct agagcaaaca   7020
aaaaatgtca gctgctggcc cgttcgcccc tcccggggac ctgcggcggg tcgcctgccc   7080
agcccccgaa ccccgcctgg aggccgcggt cggcccgggg cttctccgga ggcacccact   7140
gccaccgcga agagttgggc tctgtcagcc gcgggtctct cgggggcgag ggcgaggttc   7200
aggcctttca ggccgcagga agaggaacgg agcgagtccc cgcgcgcggc gcgattccct   7260
gagctgtggg acgtgcaccc aggactcggc tcacacatgc agttcgcttt cctgttggtg   7320
gggggaacgc cgatcgtgcg catccgtcac ccctcgccgg caatgggggc ttgtgaaccc   7380
ccaaacctga ctgactgggc cagtgtgctg caaattggca ggagacgtga aggcacctcc   7440
aaagtcgact ttctggagtt tcaaaaacag accgtacgat gcattagtta ttaatagtaa   7500
tcaattacgg ggtcattagt tcatagccca tatatggagt tccgcgttac ataacttacg   7560
gtaaatggcc cgcctggctg accgcccaac gacccccgcc cattgacgtc aataatgacg   7620
tatgttccca tagtaacgcc aatagggact ttccattgac gtcaatgggt ggagtattta   7680
cggtaaactg cccacttggc agtacatcaa gtgtatcata tgccaagtac gccccctatt   7740
gacgtcaatg acggtaaatg gcccgcctgg cattatgccc agtacatgac cttatgggac   7800
tttcctactt ggcagtacat ctacgtatta gtcatcgcta ttaccatggt gatgcggttt   7860
tggcagtaca tcaatgggcg tggatagcgg tttgactcac ggggatttcc aagtctccac   7920
cccattgacg tcaatgggag tttgttttgg caccaaaatc aacgggactt tccaaaatgt   7980
cgtaacaact ccgccccatt gacgcaaatg ggcggtaggc gtgtacggtg ggaggtctat   8040
ataagcagag ctggtttagt gaaccgtcag atccgctagc ccaccatgc cgcgcgctcc    8100
ccgctgccga gccgtgcgct ccctgctgcg cagccactac cgcgaggtgc tgccgctggc   8160
cacgttcgtg cggcgcctgg ggccccaggg ctggcggctg gtgcagcgcg gggacccggc   8220
ggctttccgc gcgctggtgg cccagtgcct ggtgtgcgtg ccctgggacg cacggccgcc   8280
ccccgccgcc ccctccttcc gccaggtgtc ctgcctgaag gagctggtgg cccgagtgct   8340
gcagaggctg tgcgagcgcg gcgcgaagaa cgtgctggcc ttcggcttcg cgctgctgga   8400
cggggcccgc gggggccccc ccgaggcctt caccaccagc gtgcgcagct acctgcccaa   8460
cacggtgacc gacgcactgc gggggagcgg ggcgtggggg ctgctgttgc gccgcgtggg   8520
cgacgacgtg ctggttcacc tgctggcacg ctgcgcgctc tttgtgctgg tggctcccag   8580
ctgcgcctac caggtgtgcg ggccgccgct gtaccagctc ggcgctgcca ctcaggcccg   8640
gcccccgcca cacgctagtg gaccccgaag gcgtctggga tgcgaacggg cctggaacca   8700
tagcgtcagg gaggccgggg tcccccctggg cctgccagcc ccgggtgcga ggaggcgcgg   8760
```

```
gggcagtgcc agccgaagtc tgccgttgcc caagaggccc aggcgtggcg ctgcccctga   8820
gccggagcgg acgcccgttg ggcaggggtc ctgggcccac ccgggcagga cgcgtggacc   8880
gagtgaccgt ggtttctgtg tggtgtcacc tgccagaccc gccgaagaag ccacctcttt   8940
ggagggtgcg ctctctggca cgcgccactc ccacccatcc gtgggccgcc agcaccacgc   9000
gggcccccca tccacatcgc ggccaccacg tccctgggac acgccttgtc cccggtgta   9060
cgccgagacc aagcacttcc tctactcctc aggcgacaag gagcagctgc ggccctcctt   9120
cctactcagc tctctgaggc ccagcctgac tggcgctcgg aggctcgtgg agaccatctt   9180
tctgggttcc aggccctgga tgccagggac tccccgcagg ttgccccgcc tgccccagcg   9240
ctactggcaa atgcggcccc tgtttctgga gctgcttggg aaccacgcgc agtgccccta   9300
cggggtgctc ctcaagacgc actgcccgct gcgagctgcg gtcaccccag cagccggtgt   9360
ctgtgcccgg gagaagcccc agggctctgt ggcggccccc gaggaggagg acacagaccc   9420
ccgtcgcctg gtgcagctgc tccgccagca cagcagcccc tggcaggtgt acggcttcgt   9480
gcgggcctgc ctgcgccggc tggtgccccc aggcctctgg ggctccaggc acaacgaacg   9540
ccgcttcctc aggaacacca agaagttcat ctccctgggg aagcatgcca agctctcgct   9600
gcaggagctg acgtggaaga tgagcgtgcg gggctgcgct tggctgcgca ggagcccagg   9660
ggttggctgt gttccggccg cagagcaccg tctgcgtgag gagatcctgg ccaagttcct   9720
gcactggctg atgagtgtgt acgtcgtcga gctgctcagg tctttctttt atgtcacgga   9780
gaccacgttt caaaagaaca ggctcttttt ctaccggaag agtgtctgga gcaagttgca   9840
aagcattgga atcagacagc acttgaagag ggtgcagctg cgggagctgt cggaagcaga   9900
ggtcaggcag catcgggaag ccaggcccgc cctgctgacg tccagactcc gcttcatccc   9960
caagcctgac gggctgcggc cgattgtgaa catggactac gtcgtgggag ccagaacgtt  10020
ccgcagagaa aagagggccg agcgtctcac ctccagggtg aaggcactgt tcagcgtgct  10080
caactacgag cgggcgcggc gccccggcct cctgggcgcc tctgtgctgg gcctggacga  10140
tatccacagg gcctggcgca ccttcgtgct gcgtgtgcgg gcccaggacc cgccgcctga  10200
gctgtacttt gtcaaggtgg atgtgacggg cgcgtacgac accatccccc aggacaggct  10260
cacggaggtc atcgccagca tcatcaaacc ccagaacacg tactgcgtgc gtcggtatgc  10320
cgtggtccag aaggccgccc atgggcacgt ccgcaaggcc ttcaagagcc acgtctctac  10380
cttgacagac ctccagccgt acatgcgaca gttcgtggct cacctgcagg agaccagccc  10440
gctgagggat gccgtcgtca tcgagcagag ctcctccctg aatgaggcca gcagtggcct  10500
cttcgacgtc ttcctacgct tcatgtgcca ccacgccgtg cgcatcaggg gcaagtccta  10560
cgtccagtgc caggggatcc cgcagggctc catcctctcc acgctgctct gcagcctgtg  10620
ctacggcgac atggagaaca agctgtttgc ggggattcgg cgggacgggc tgctcctgcg  10680
tttggtggat gatttcttgt tggtgacacc tcacctcacc cacgcgaaaa ccttcctcag  10740
gaccctggtc cgaggtgtcc ctgagtatgg ctgcgtggtg aacttgcgga agacagtggt  10800
gaacttccct gtagaagacg aggccctggg tggcacggct tttgttcaga tgccggccca  10860
cggcctattc ccctggtgcg gcctgctgct ggatacccgg accctggagg tgcagagcga  10920
ctactccagc tatgcccgga cctccatcag agccagtctc accttcaacc gcggcttcaa  10980
ggctgggagg aacatgcgtc gcaaactctt tggggtcttg cggctgaagt gtcacagcct  11040
gtttctggat ttgcaggtga acagcctcca gacggtgtgc accaacatct acaagatcct  11100
```

```
cctgctgcag gcgtacaggt ttcacgcatg tgtgctgcag ctcccatttc atcagcaagt  11160
ttggaagaac cccacatttt tcctgcgcgt catctctgac acggcctccc tctgctactc  11220
catcctgaaa gccaagaacg cagggatgtc gctgggggcc aagggcgccg ccggccctct  11280
gccctccgag gccgtgcagt ggctgtgcca ccaagcattc ctgctcaagc tgactcgaca  11340
ccgtgtcacc tacgtgccac tcctggggtc actcaggaca gcccagacgc agctgagtcg  11400
gaagctcccg ggacgacgc tgactgccct ggaggccgca gccaacccgg cactgccctc  11460
agacttcaag accatcctgg actgagtcga aactcgcggc cgccatatgc atcctaggcc  11520
tattaatatt ccggagtata cgtagccggc taacgttaac ttgtttattg cagcttataa  11580
tggttacaaa taaagcaata gcatcacaaa tttcacaaat aaagcatttt tttcactgca  11640
ttctagttgt ggtttgtcca aactcatcaa tgtatcttaa cgcggatctg ggcgtggtta  11700
agggtgggaa agaatatata aggtgggggt cttatgtagt tttgtatctg ttttgcagca  11760
gccgccgccg ccatgagcac caactcgttt gatggaagca ttgtgagctc atatttgaca  11820
acgcgcatgc ccccatgggc cggggtgcgt cagaatgtga tgggctccag cattgatggt  11880
cgccccgtcc tgcccgcaaa ctctactacc ttgacctacg agaccgtgtc tggaacgccg  11940
ttggagactg cagcctccgc cgccgcttca gccgctgcag ccaccgcccg cgggattgtg  12000
actgactttg ctttcctgag cccgcttgca agcagtgcag cttcccgttc atccgcccgc  12060
gatgacaagt tgacggctct tttggcacaa ttggattctt tgacccggga acttaatgtc  12120
gtttctcagc agctgttgga tctgcgccag caggtttctg ccctgaaggc ttcctcccct  12180
cccaatgcgg tttaaaacat aaataaaaaa ccagactctg tttggatttg gatcaagcaa  12240
gtgtcttgct gtctttattt aggggttttg cgcgcgcggt aggcccggga ccagcggtct  12300
cggtcgttga gggtcctgtg tatttttttcc aggacgtggt aaaggtgact ctggatgttc  12360
agatacatgg gcataagccc gtctctgggg tggaggtagc accactgcag agcttcatgc  12420
tgcggggtgg tgttgtagat gatccagtcg tagcaggagc gctgggcgtg gtgcctaaaa  12480
atgtctttca gtagcaagct gattgccagg ggcaggccct tggtgtaagt gtttacaaag  12540
cggttaagct gggatgggtg catacgtggg gatatgagat gcatcttgga ctgtattttt  12600
aggttggcta tgttcccagc catatccctc cggggattca tgttgtgcag aaccaccagc  12660
acagtgtatc cggtgcactt gggaaatttg tcatgtagct tagaaggaaa tgcgtggaag  12720
aacttggaga cgcccttgtg acctccaaga ttttccatgc attcgtccat aatgatggca  12780
atgggcccac gggcggcggc ctgggcgaag atatttctgg gatcactaac gtcatagttg  12840
tgttccagga tgagatcgtc ataggccatt tttacaaagc gcgggcggag ggtgccagac  12900
tgcggtataa tggttccatc cggcccaggg gcgtagttac cctcacagat ttgcatttcc  12960
cacgctttga gttcagatgg ggggatcatg tctacctgcg gggcgatgaa gaaaacggtt  13020
tccggggtag gggagatcag ctgggaagaa agcaggttcc tgagcagctg cgacttaccg  13080
cagccggtgg gcccgtaaat cacacctatt accgggtgca actggtagtt aagagagctg  13140
cagctgccgt catccctgag caggggggcc acttcgttaa gcatgtccct gactcgcatg  13200
ttttccctga ccaaatccgc cagaaggcgc tcgccgccca gcgatagcag ttcttgcaag  13260
gaagcaaagt ttttcaacgg tttgagaccg tccgccgtag gcatgctttt gagcgtttga  13320
ccaagcagtt ccaggcggtc ccacagctcg gtcacctgct ctacggcatc tcgatccagc  13380
atatctcctc gtttcgcggg ttggggcggc tttcgctgta cggcagtagt cggtgctcgt  13440
ccagacgggc cagggtcatg tctttccacg ggcgcagggt cctcgtcagc gtagtctggg  13500
```

```
tcacggtgaa ggggtgcgct ccgggctgcg cgctggccag ggtgcgcttg aggctggtcc  13560
tgctggtgct gaagcgctgc cggtcttcgc cctgcgcgtc ggccaggtag catttgacca  13620
tggtgtcata gtccagcccc tccgcggcgt ggcccttggc gcgcagcttg cccttggagg  13680
aggcgccgca cgaggggcag tgcagacttt tgagggcgta gagcttgggc gcgagaaata  13740
ccgattccgg ggagtaggca tccgcgccgc aggccccgca gacggtctcg cattccacga  13800
gccaggtgag ctctggccgt tcggggtcaa aaaccaggtt tcccccatgc tttttgatgc  13860
gtttcttacc tctggtttcc atgagccggt gtccacgctc ggtgacgaaa aggctgtccg  13920
tgtccccgta tacagacttg agaggcctgt cctcgagcgg tgttccgcgg tcctcctcgt  13980
atagaaactc ggaccactct gagacaaagg ctcgcgtcca ggccagcacg aaggaggcta  14040
agtgggaggg gtagcggtcg ttgtccacta gggggtccac tcgctccagg gtgtgaagac  14100
acatgtcgcc ctcttcggca tcaaggaagg tgattggttt gtaggtgtag gccacgtgac  14160
cgggtgttcc tgaagggggg ctataaaagg gggtgggggc gcgttcgtcc tcactctctt  14220
ccgcatcgct gtctgcgagg gccagctgtt ggggtgagta ctccctctga aaagcgggca  14280
tgacttctgc gctaagattg tcagtttcca aaaacgagga ggatttgata ttcacctggc  14340
ccgcggtgat gcctttgagg gtggccgcat ccatctggtc agaaaagaca atctttttgt  14400
tgtcaagctt ggtggcaaac gacccgtaga gggcgttgga cagcaacttg gcgatggagc  14460
gcagggtttg gtttttgtcg cgatcggcgc gctccttggc cgcgatgttt agctgcacgt  14520
attcgcgcgc aacgcaccgc cattcgggaa agacggtggt gcgctcgtcg ggcaccaggt  14580
gcacgcgcca accgcggttg tgcagggtga caaggtcaac gctggtggct acctctccgc  14640
gtaggcgctc gttggtccag cagaggcggc cgcccttgcg cgagcagaat ggcggtaggg  14700
ggtctagctg cgtctcgtcc ggggggtctg cgtccacggt aaagaccccg ggcagcaggc  14760
gcgcgtcgaa gtagtctatc ttgcatcctt gcaagtctag cgcctgctgc catgcgcggg  14820
cggcaagcgc gcgctcgtat gggttgagtg ggggacccca tggcatgggg tgggtgagcg  14880
cggaggcgta catgccgcaa atgtcgtaaa cgtagagggg ctctctgagt attccaagat  14940
atgtagggta gcatcttcca ccgcggatgc tggcgcgcac gtaatcgtat agttcgtgcg  15000
agggagcgag gaggtcggga ccgaggttgc tacgggcggg ctgctctgct cggaagacta  15060
tctgcctgaa gatggcatgt gagttggatg atatggttgg acgctggaag acgttgaagc  15120
tggcgtctgt gagacctacc gcgtcacgca cgaaggaggc gtaggagtcg cgcagcttgt  15180
tgaccagctc ggcggtgacc tgcacgtcta gggcgcagta gtccagggtt tccttgatga  15240
tgtcatactt atcctgtccc ttttttttcc acagctcgcg gttgaggaca aactcttcgc  15300
ggtctttcca gtactcttgg atcggaaacc cgtcggcctc cgaacggtaa gagcctagca  15360
tgtagaactg gttgacggcc tggtaggcgc agcatccctt ttctacgggt agcgcgtatg  15420
cctgcgcggc cttccggagc gaggtgtggg tgagcgcaaa ggtgtccctg accatgactt  15480
tgaggtactg gtatttgaag tcagtgtcgt cgcatccgcc ctgctcccag agcaaaaagt  15540
ccgtgcgctt tttggaacgc ggatttggca gggcgaaggt gacatcgttg aagagtatct  15600
ttcccgcgcg aggcataaag ttgcgtgtga tgcggaaggg tcccggcacc tcggaacggt  15660
tgttaattac ctgggcggcg agcacgatct cgtcaaagcc gttgatgttg tggcccacaa  15720
tgtaaagttc caagaagcgc gggatgccct tgatggaagg caatttttta agttcctcgt  15780
aggtgagctc ttcaggggag ctgagcccgt gctctgaaag ggcccagtct gcaagatgag  15840
```

```
ggttggaagc gacgaatgag ctccacaggt cacgggccat tagcatttgc aggtggtcgc  15900
gaaaggtcct aaactggcga cctatggcca tttttctgg ggtgatgcag tagaaggtaa  15960
gcgggtcttg ttcccagcgg tcccatccaa ggttcgcggc taggtctcgc gcggcagtca  16020
ctagaggctc atctccgccg aacttcatga ccagcatgaa gggcacgagc tgcttcccaa  16080
aggcccccat ccaagtatag gtctctacat cgtaggtgac aaagagacgc tcggtgcgag  16140
gatgcgagcc gatcgggaag aactggatct cccgccacca attggaggag tggctattga  16200
tgtggtgaaa gtagaagtcc ctgcgacggg ccgaacactc gtgctggctt ttgtaaaaac  16260
gtgcgcagta ctggcagcgg tgcacgggct gtacatcctg cacgaggttg acctgacgac  16320
cgcgcacaag gaagcagagt gggaatttga gcccctcgcc tggcgggttt ggctggtggt  16380
cttctacttc ggctgcttgt ccttgaccgt ctggctgctc gaggggagtt acggtggatc  16440
ggaccaccac gccgcgcgag cccaaagtcc agatgtccgc gcgcggcggt cggagcttga  16500
tgacaacatc gcgcagatgg gagctgtcca tggtctggag ctcccgcggc gtcaggtcag  16560
gcgggagctc ctgcaggttt acctcgcata gacgggtcag ggcgcgggct agatccaggt  16620
gatacctaat ttccaggggc tggttggtgg cggcgtcgat ggcttgcaag aggccgcatc  16680
cccgcggcgc gactacggta ccgcgcggcg ggcggtgggc cgcgggggtg tccttggatg  16740
atgcatctaa aagcggtgac gcgggcgagc cccggaggt aggggggct ccggacccgc  16800
cgggagaggg ggcaggggca cgtcggcgcc gcgcgcgggc aggagctggt gctgcgcgcg  16860
taggttgctg gcgaacgcga cgacgcggcg gttgatctcc tgaatctggc gcctctgcgt  16920
gaagacgacg ggcccggtga gcttgagcct gaaagagagt tcgacagaat caatttcggt  16980
gtcgttgacg gcggcctggc gcaaaatctc ctgcacgtct cctgagttgt cttgataggc  17040
gatctcggcc atgaactgct cgatctcttc ctcctggaga tctccgcgtc cggctcgctc  17100
cacggtggcg gcgaggtcgt tggaaatgcg ggccatgagc tgcgagaagg cgttgaggcc  17160
tccctcgttc cagacgcggc tgtagaccac gccccttcg gcatcgcggg cgcgcatgac  17220
cacctgcgcg agattgagct ccacgtgccg ggcgaagacg gcgtagtttc gcaggcgctg  17280
aaagaggtag ttgagggtgg tggcggtgtg ttctgccacg aagaagtaca taacccagcg  17340
tcgcaacgtg gattcgttga tatcccccaa ggcctcaagg cgctccatgg cctcgtagaa  17400
gtccacggcg aagttgaaaa actgggagtt gcgcgccgac acggttaact cctcctccag  17460
aagacggatg agctcggcga cagtgtcgcg cacctcgcgc tcaaaggcta caggggcctc  17520
ttcttcttct tcaatctcct cttccataag ggcctcccct tcttcttctt ctggcggcgg  17580
tgggggaggg gggacacggc ggcgacgacg gcgcaccggg aggcggtcga caaagcgctc  17640
gatcatctcc ccgcggcgac ggcgcatggt ctcggtgacg gcgcggccgt tctcgcgggg  17700
gcgcagttgg aagacgccgc ccgtcatgtc ccggttatgg gttggcgggg ggctgccatg  17760
cggcagggat acggcgctaa cgatgcatct caacaattgt tgtgtaggta ctccgccgcc  17820
gagggacctg agcgagtccg catcgaccgg atcggaaaac ctctcgagaa aggcgtctaa  17880
ccagtcacag tcgcaaggta ggctgagcac cgtggcgggc ggcagcgggc ggcggtcggg  17940
gttgtttctg gcggaggtgc tgctgatgat gtaattaaag taggcggtct tgagacggcg  18000
gatggtcgac agaagcacca tgtccttggg tccggcctgc tgaatgcgca ggcggtcggc  18060
catgccccag gcttcgtttt gacatcggcg caggtctttg tagtagtctt gcatgagcct  18120
ttctaccggc acttcttctt ctccttcctc ttgtcctgca tctcttgcat ctatcgctgc  18180
ggcggcggcg gagtttggcc gtaggtggcg ccctcttcct cccatgcgtg tgaccccgaa  18240
```

```
gcccctcatc ggctgaagca gggctaggtc ggcgacaacg cgctcggcta atatggcctg  18300
ctgcacctgc gtgagggtag actggaagtc atccatgtcc acaaagcggt ggtatgcgcc  18360
cgtgttgatg gtgtaagtgc agttggccat aacggaccag ttaacggtct ggtgacccgg  18420
ctgcgagagc tcggtgtacc tgagacgcga gtaagccctc gagtcaaata cgtagtcgtt  18480
gcaagtccgc accaggtact ggtatcccac caaaaagtgc ggcggcggct ggcggtagag  18540
gggccagcgt agggtggccg gggctccggg ggcgagatct tccaacataa ggcgatgata  18600
tccgtagatg tacctggaca tccaggtgat gccggcggcg gtggtggagg cgcgcggaaa  18660
gtcgcggacg cggttccaga tgttgcgcag cggcaaaaag tgctccatgg tcgggacgct  18720
ctggccggtc aggcgcgcgc aatcgttgac gctctaccgt gcaaaaggag agcctgtaag  18780
cgggcactct tccgtggtct ggtggataaa ttcgcaaggg tatcatggcg gacgaccggg  18840
gttcgagccc cgtatccggc cgtccgccgt gatccatgcg gttaccgccc gcgtgtcgaa  18900
cccaggtgtg cgacgtcaga caacgggga gtgctccttt tggcttcctt ccaggcgcgg  18960
cggctgctgc gctagctttt ttggccactg gccgcgcgca gcgtaagcgg ttaggctgga  19020
aagcgaaagc attaagtggc tcgctccctg tagccggagg gttattttcc aagggttgag  19080
tcgcgggacc cccggttcga gtctcggacc ggccggactg cggcgaacgg gggtttgcct  19140
ccccgtcatg caagaccccg cttgcaaatt cctccggaaa cagggacgag ccccttttt  19200
gcttttccca gatgcatccg gtgctgcggc agatgcgccc ccctcctcag cagcggcaag  19260
agcaagagca gcggcagaca tgcagggcac cctcccctcc tcctaccgcg tcaggagggg  19320
cgacatccgc ggttgacgcg gcagcagatg gtgattacga accccgcgg cgccgggccc  19380
ggcactacct ggacttggag gagggcgagg gcctggcgcg gctaggagcg ccctctcctg  19440
agcggtaccc aagggtgcag ctgaagcgtg atacgcgtga ggcgtacgtg ccgcggcaga  19500
acctgtttcg cgaccgcgag ggagaggagc ccgaggagat gcgggatcga aagttccacg  19560
cagggcgcga gctgcggcat ggcctgaatc gcgagcggtt gctgcgcgag gaggactttg  19620
agcccgacgc gcgaaccggg attagtcccg cgcgcgcaca cgtggcggcc gccgacctgg  19680
taaccgcata cgagcagacg gtgaaccagg agattaactt tcaaaaaagc tttaacaacc  19740
acgtgcgtac gcttgtggcg cgcgaggagg tggctatagg actgatgcat ctgtgggact  19800
ttgtaagcgc gctggagcaa aacccaaata gcaagccgct catggcgcag ctgttcctta  19860
tagtgcagca cagcagggac aacgaggcat tcagggatgc gctgctaaac atagtagagc  19920
ccgagggccg ctggctgctc gatttgataa acatcctgca gagcatagtg gtgcaggagc  19980
gcagcttgag cctggctgac aaggtggccg ccatcaacta ttccatgctt agcctgggca  20040
agttttacgc ccgcaagata taccataccc cttacgttcc catagacaag gaggtaaaga  20100
tcgaggggtt ctacatgcgc atggcgctga aggtgcttac cttgagcgac gacctgggcg  20160
tttatcgcaa cgagcgcatc cacaaggccg tgagcgtgag ccggcggcgc gagctcagcg  20220
accgcgagct gatgcacagc ctgcaaaggg ccctggctgg cacgggcagc ggcgatagag  20280
aggccgagtc ctactttgac gcgggcgctg acctgcgctg ggccccaagc cgacgcgccc  20340
tggaggcagc tggggccgga cctgggctgg cggtggcacc cgcgcgcgct ggcaacgtcg  20400
gcggcgtgga ggaatatgac gaggacgatg agtacgagcc agaggacggc gagtactaag  20460
cggtgatgtt tctgatcaga tgatgcaaga cgcaacggac ccggcggtgc gggcggcgct  20520
gcagagccag ccgtccggcc ttaactccac ggacgactgg cgccaggtca tggaccgcat  20580
```

-continued

```
catgtcgctg actgcgcgca atcctgacgc gttccggcag cagccgcagg ccaaccggct  20640
ctccgcaatt ctggaagcgg tggtcccggc gcgcgcaaac cccacgcacg agaaggtgct  20700
ggcgatcgta aacgcgctgg ccgaaaacag ggccatccgg cccgacgagg ccggcctggt  20760
ctacgacgcg ctgcttcagc gcgtggctcg ttacaacagc ggcaacgtgc agaccaacct  20820
ggaccggctg gtgggggatg tgcgcgaggc cgtggcgcag cgtgagcgcg cgcagcagca  20880
gggcaacctg ggctccatgg ttgcactaaa cgccttcctg agtacacagc ccgccaacgt  20940
gccgcgggga caggaggact acaccaactt tgtgagcgca ctgcggctaa tggtgactga  21000
gacaccgcaa agtgaggtgt accagtctgg gccagactat tttttccaga ccagtagaca  21060
aggcctgcag accgtaaacc tgagccaggc tttcaaaaac ttgcaggggc tgtggggggt  21120
gcgggctccc acaggcgacc gcgcgaccgt gtctagcttg ctgacgccca actcgcgcct  21180
gttgctgctg ctaatagcgc ccttcacgga cagtggcagc gtgtcccggg acacatacct  21240
aggtcacttg ctgacactgt accgcgaggc cataggtcag gcgcatgtgg acgagcatac  21300
tttccaggag attacaagtg tcagccgcgc gctggggcag gaggacacgg gcagcctgga  21360
ggcaacccta aactacctgc tgaccaaccg gcggcagaag atcccctcgt tgcacagttt  21420
aaacagcgag gaggagcgca ttttgcgcta cgtgcagcag agcgtgagcc ttaacctgat  21480
gcgcgacggg gtaacgccca gcgtggcgct ggacatgacc gcgcgcaaca tggaaccggg  21540
catgtatgcc tcaaaccggc cgtttatcaa ccgcctaatg gactacttgc atcgcgcggc  21600
cgccgtgaac cccgagtatt tcaccaatgc catcttgaac ccgcactggc taccgccccc  21660
tggtttctac accgggggat tcgaggtgcc cgagggtaac gatggattcc tctgggacga  21720
catagacgac agcgtgtttt ccccgcaacc gcagaccctg ctagagttgc aacagcgcga  21780
gcaggcagag gcggcgctgc gaaaggaaag cttccgcagg ccaagcagct tgtccgatct  21840
aggcgctgcg gccccgcggt cagatgctag tagcccattt ccaagcttga tagggtctct  21900
taccagcact cgcaccaccc gcccgcgcct gctgggcgag gaggagtacc taaacaactc  21960
gctgctgcag ccgcagcgcg aaaaaaacct gcctccggca tttcccaaca acgggataga  22020
gagcctagtg gacaagatga gtagatggaa gacgtacgcg caggagcaca gggacgtgcc  22080
aggcccgcgc ccgcccaccc gtcgtcaaag gcacgaccgt cagcggggtc tggtgtggga  22140
ggacgatgac tcggcagacg acagcagcgt cctggatttg ggagggagtg gcaacccgtt  22200
tgcgcacctt cgccccaggc tggggagaat gttttaaaaa aaaaaaagca tgatgcaaaa  22260
taaaaaactc accaaggcca tggcaccgag cgttggtttt cttgtattcc ccttagtatg  22320
cggcgcgcgg cgatgtatga ggaaggtcct cctccctcct acgagagtgt ggtgagcgcg  22380
gcgccagtgg cggcggcgct gggttctccc ttcgatgctc ccctggaccc gccgtttgtg  22440
cctccgcggt acctgcggcc taccgggggg agaaacagca tccgttactc tgagttggca  22500
cccctattcg acaccacccg tgtgtacctg gtggacaaca agtcaacgga tgtggcatcc  22560
ctgaactacc agaacgacca cagcaacttt ctgaccacgg tcattcaaaa caatgactac  22620
agcccggggg aggcaagcac acagaccatc aatcttgacg accggtcgca ctggggcggc  22680
gacctgaaaa ccatcctgca taccaacatg ccaaatgtga acgagttcat gtttaccaat  22740
aagtttaagg cgcgggtgat ggtgtcgcgc ttgcctacta aggacaatca ggtggagctg  22800
aaatacgagt gggtggagtt cacgctgccc gagggcaact actccgagac catgaccata  22860
gaccttatga acaacgcgat cgtggagcac tacttgaaag tgggcagaca gaacggggtt  22920
ctggaaagcg acatcggggt aaagtttgac acccgcaact tcagactggg gtttgacccc  22980
```

```
gtcactggtc ttgtcatgcc tggggtatat acaaacgaag ccttccatcc agacatcatt  23040
ttgctgccag gatgcggggt ggacttcacc cacagccgcc tgagcaactt gttgggcatc  23100
cgcaagcggc aacccttcca ggagggcttt aggatcacct acgatgatct ggagggtggt  23160
aacattcccg cactgttgga tgtggacgcc taccaggcga gcttgaaaga tgacaccgaa  23220
cagggcgggg gtggcgcagg cggcagcaac agcagtggca gcggcgcgga agagaactcc  23280
aacgcggcag ccgcggcaat gcagccggtg gaggacatga acgatcatgc cattcgcggc  23340
gacacctttg ccacacgggc tgaggagaag cgcgctgagg ccgaagcagc ggccgaagct  23400
gccgcccccg ctgcgcaacc cgaggtcgag aagcctcaga agaaaccggt gatcaaaccc  23460
ctgacagagg acagcaagaa acgcagttac aacctaataa gcaatgacag caccttcacc  23520
cagtaccgca gctggtacct tgcatacaac tacggcgacc ctcagaccgg aatccgctca  23580
tggaccctgc tttgcactcc tgacgtaacc tgcggctcgg agcaggtcta ctggtcgttg  23640
ccagacatga tgcaagaccc cgtgaccttc cgctccacgc gccagatcag caactttccg  23700
gtggtgggcg ccgagctgtt gcccgtgcac tccaagagct tctacaacga ccaggccgtc  23760
tactcccaac tcatccgcca gtttacctct ctgacccacg tgttcaatcg ctttcccgag  23820
aaccagattt tggcgcgccc gccagccccc accatcacca ccgtcagtga aaacgttcct  23880
gctctcacag atcacgggac gctaccgctg cgcaacagca tcggaggagt ccagcgagtg  23940
accattactg acgccagacg ccgcacctgc ccctacgttt acaaggccct gggcatagtc  24000
tcgccgcgcg tcctatcgag ccgcactttt tgagcaagca tgtccatcct tatatcgccc  24060
agcaataaca caggctgggg cctgcgcttc ccaagcaaga tgtttggcgg ggccaagaag  24120
cgctccgacc aacacccagt gcgcgtgcgc gggcactacc gcgcgccctg gggcgcgcac  24180
aaacgcggcc gcactgggcg caccaccgtc gatgacgcca tcgacgcggt ggtggaggag  24240
gcgcgcaact acacgcccac gccgccacca gtgtccacag tggacgcggc cattcagacc  24300
gtggtgcgcg gagcccggcg ctatgctaaa atgaagagac ggcggaggcg cgtagcacgt  24360
cgccaccgcc gccgacccgg cactgccgcc caacgcgcgg cggcggccct gcttaaccgc  24420
gcacgtcgca ccggccgacg ggcggccatg cgggccgctc gaaggctggc cgcgggtatt  24480
gtcactgtgc cccccaggtc caggcgacga gcggccgccg cagcagccgc ggccattagt  24540
gctatgactc agggtcgcag gggcaacgtg tattgggtgc gcgactcggt tagcggcctg  24600
cgcgtgcccg tgcgcacccg ccccccgcgc aactagattg caagaaaaaa ctacttagac  24660
tcgtactgtt gtatgtatcc agcggcggcg gcgcgcaacg aagctatgtc caagcgcaaa  24720
atcaaagaag agatgctcca ggtcatcgcg ccggagatct atggcccccc gaagaaggaa  24780
gagcaggatt acaagccccg aaagctaaag cgggtcaaaa agaaaaagaa agatgatgat  24840
gatgaacttg acgacgaggt ggaactgctg cacgctaccg cgcccaggcg acgggtacag  24900
tggaaaggtc gacgcgtaaa acgtgttttg cgacccggca ccaccgtagt ctttacgccc  24960
ggtgagcgct ccacccgcac ctacaagcgc gtgtatgatg aggtgtacgg cgacgaggac  25020
ctgcttgagc aggccaacga gcgcctcggg gagtttgcct acggaaagcg gcataaggac  25080
atgctggcgt tgccgctgga cgagggcaac ccaacaccta gcctaaagcc cgtaacactg  25140
cagcaggtgc tgcccgcgct tgcaccgtcc gaagaaaagc gcggcctaaa gcgcgagtct  25200
ggtgacttgg cacccaccgt gcagctgatg gtacccaagc gccagcgact ggaagatgtc  25260
ttggaaaaaa tgaccgtgga acctgggctg gagcccgagg tccgcgtgcg gccaatcaag  25320
```

```
caggtggcgc cgggactggg cgtgcagacc gtggacgttc agatacccac taccagtagc  25380
accagtattg ccaccgccac agagggcatg gagacacaaa cgtccccggt tgcctcagcg  25440
gtggcggatg ccgcggtgca ggcggtcgct gcggccgcgt ccaagacctc tacggaggtg  25500
caaacggacc cgtggatgtt tcgcgtttca gcccccggc gcccgcgcgg ttcgaggaag  25560
tacggcgccg ccagcgcgct actgcccgaa tatgccctac atccttccat tgcgcctacc  25620
cccggctatc gtggctacac ctaccgcccc agaagacgag caactacccg acgccgaacc  25680
accactggaa cccgccgccg ccgtcgccgt cgccagcccg tgctggcccc gatttccgtg  25740
cgcagggtgg ctcgcgaagg aggcaggacc ctggtgctgc caacagcgcg ctaccacccc  25800
agcatcgttt aaaagccggt ctttgtggtt cttgcagata tggccctcac ctgccgcctc  25860
cgtttcccgg tgccgggatt ccgaggaaga atgcaccgta ggaggggcat ggccggccac  25920
ggcctgacgg gcggcatgcg tcgtgcgcac caccggcggc ggcgcgcgtc gcaccgtcgc  25980
atgcgcggcg gtatcctgcc cctccttatt ccactgatcg ccgcggcgat tggcgccgtg  26040
cccggaattg catccgtggc cttgcaggcg cagagacact gattaaaaac aagttgcatg  26100
tggaaaaatc aaaataaaaa gtctggactc tcacgctcgc ttggtcctgt aactattttg  26160
tagaatggaa gacatcaact ttgcgtctct ggccccgcga cacggctcgc gcccgttcat  26220
gggaaactgg caagatatcg gcaccagcaa tatgagcggt ggcgccttca gctggggctc  26280
gctgtggagc ggcattaaaa atttcggttc caccgttaag aactatggca gcaaggcctg  26340
gaacagcagc acaggccaga tgctgaggga taagttgaaa gagcaaaatt tccaacaaaa  26400
ggtggtagat ggcctggcct ctggcattag cggggtggtg gacctggcca accaggcagt  26460
gcaaaataag attaacagta agcttgatcc ccgccctccc gtagaggagc ctccaccggc  26520
cgtggagaca gtgtctccag aggggcgtgg cgaaaagcgt ccgcgccccg acagggaaga  26580
aactctggtg acgcaaatag acgagcctcc ctcgtacgag gaggcactaa agcaaggcct  26640
gcccaccacc cgtcccatcg cgcccatggc taccggagtg ctgggccagc acacacccgt  26700
aacgctggac ctgcctcccc ccgccgacac ccagcagaaa cctgtgctgc caggcccgac  26760
cgccgttgtt gtaacccgtc ctagccgcgc gtccctgcgc cgcgccgcca gcggtccgcg  26820
atcgttgcgg cccgtagcca gtggcaactg gcaaagcaca ctgaacagca tcgtgggtct  26880
gggggtgcaa tccctgaagc gccgacgatg cttctgaata gctaacgtgt cgtatgtgtg  26940
tcatgtatgc gtccatgtcg ccgccagagg agctgctgag ccgccgcgcg cccgctttcc  27000
aagatggcta ccccttcgat gatgccgcag tggtcttaca tgcacatctc gggccaggac  27060
gcctcggagt acctgagccc cgggctggtg cagtttgccc gcgccaccga gacgtacttc  27120
agcctgaata acaagtttag aaaccccacg gtggcgccta cgcacgacgt gaccacagac  27180
cggtcccagc gtttgacgct gcggttcatc cctgtggacc gtgaggatac tgcgtactcg  27240
tacaaggcgc ggttcaccct agctgtgggt gataaccgtg tgctggacat ggcttccacg  27300
tactttgaca tccgcggcgt gctggacagg ggccctactt ttaagcccta ctctggcact  27360
gcctacaacg ccctggctcc caagggtgcc ccaaatcctt gcgaatggga tgaagctgct  27420
actgctcttg aaataaacct agaagaagag gacgatgaca acgaagacga agtagacgag  27480
caagctgagc agcaaaaaac tcacgtattt gggcaggcgc cttattctgg tataaatatt  27540
acaaaggagg gtattcaaat aggtgtcgaa ggtcaaacac ctaaatatgc cgataaaaca  27600
tttcaacctg aacctcaaat aggagaatct cagtggtacg aaactgaaat taatcatgca  27660
gctgggagag tccttaaaaa gactacccca atgaaaccat gttacggttc atatgcaaaa  27720
```

```
cccacaaatg aaaatggagg gcaaggcatt cttgtaaagc aacaaaatgg aaagctagaa  27780
agtcaagtgg aaatgcaatt tttctcaact actgaggcga ccgcaggcaa tggtgataac  27840
ttgactccta aagtggtatt gtacagtgaa gatgtagata tagaaacccc agacactcat  27900
atttcttaca tgcccactat taaggaaggt aactcacgag aactaatggg ccaacaatct  27960
atgcccaaca ggcctaatta cattgctttt agggacaatt ttattggtct aatgtattac  28020
aacagcacgg gtaatatggg tgttctggcg ggccaagcat cgcagttgaa tgctgttgta  28080
gatttgcaag acagaaacac agagctttca taccagcttt tgcttgattc cattggtgat  28140
agaaccaggt acttttctat gtggaatcag gctgttgaca gctatgatcc agatgttaga  28200
attattgaaa atcatggaac tgaagatgaa cttccaaatt actgctttcc actgggaggt  28260
gtgattaata cagagactct taccaaggta aaacctaaaa caggtcagga aaatggatgg  28320
gaaaaagatg ctacagaatt ttcagataaa aatgaaataa gagttggaaa taattttgcc  28380
atggaaatca atctaaatgc caacctgtgg agaaatttcc tgtactccaa catagcgctg  28440
tatttgcccg acaagctaaa gtacagtcct tccaacgtaa aaatttctga taacccaaac  28500
acctacgact acatgaacaa gcgagtggtg gctcccgggt tagtggactg ctacattaac  28560
cttggagcac gctggtccct tgactatatg gacaacgtca acccatttaa ccaccaccgc  28620
aatgctggcc tgcgctaccg ctcaatgttg ctgggcaatg gtcgctatgt gcccttccac  28680
atccaggtgc ctcagaagtt ctttgccatt aaaaacctcc ttctcctgcc gggctcatac  28740
acctacgagt ggaacttcag gaaggatgtt aacatggttc tgcagagctc cctaggaaat  28800
gacctaaggg ttgacggagc cagcattaag tttgatagca tttgccttta cgccaccttc  28860
ttccccatgg cccacaacac cgcctccacg cttgaggcca tgcttagaaa cgacaccaac  28920
gaccagtcct ttaacgacta tctctccgcc gccaacatgc tctaccctat acccgccaac  28980
gctaccaacg tgcccatatc catcccctcc cgcaactggg cggctttccg cggctgggcc  29040
ttcacgcgcc ttaagactaa ggaaacccca tcactgggct cgggctacga cccttattac  29100
acctactctg gctctatacc ctacctagat ggaacctttt acctcaacca cacctttaag  29160
aaggtggcca ttacctttga ctcttctgtc agctggcctg gcaatgaccg cctgcttacc  29220
cccaacgagt ttgaaattaa gcgctcagtt gacggggagg gttacaacgt tgcccagtgt  29280
aacatgacca aagactggtt cctggtacaa atgctagcta actacaacat tggctaccag  29340
ggcttctata tcccagagag ctacaaggac cgcatgtact ccttctttag aaacttccag  29400
cccatgagcc gtcaggtggt ggatgatact aaatacaagg actaccaaca ggtgggcatc  29460
ctacaccaac acaacaactc tggatttgtt ggctaccttg cccccaccat gcgcgaagga  29520
caggcctacc ctgctaactt cccctatccg cttataggca agaccgcagt tgacagcatt  29580
acccagaaaa agtttctttg cgatcgcacc ctttggcgca tcccattctc cagtaacttt  29640
atgtccatgg gcgcactcac agacctgggc caaaaccttc tctacgccaa ctccgcccac  29700
gcgctagaca tgacttttga ggtggatccc atggacgagc ccacccttct ttatgttttg  29760
tttgaagtct ttgacgtggt ccgtgtgcac cggccgcacc gcggcgtcat cgaaaccgtg  29820
tacctgcgca cgcccttctc ggccggcaac gccacaacat aaagaagcaa gcaacatcaa  29880
caacagctgc cgccatgggc tccagtgagc aggaactgaa agccattgtc aaagatcttg  29940
gttgtgggcc atatttttg ggcacctatg acaagcgctt tccaggcttt gtttctccac  30000
acaagctcgc ctgcgccata gtcaatacgg ccggtcgcga gactgggggc gtacactgga  30060
```

tggcctttgc ctggaacccg cactcaaaaa catgctacct ctttgagccc tttggctttt 30120
ctgaccagcg actcaagcag gtttaccagt ttgagtacga gtcactcctg cgccgtagcg 30180
ccattgcttc ttcccccgac cgctgtataa cgctggaaaa gtccacccaa agcgtacagg 30240
ggcccaactc ggccgcctgt ggactattct gctgcatgtt tctccacgcc tttgccaact 30300
ggccccaaac tcccatggat cacaacccca ccatgaacct tattaccggg gtacccaact 30360
ccatgctcaa cagtccccag gtacagccca ccctgcgtcg caaccaggaa cagctctaca 30420
gcttcctgga gcgccactcg ccctacttcc gcagccacag tgcgcagatt aggagcgcca 30480
cttctttttg tcacttgaaa aacatgtaaa aataatgtac tagagacact ttcaataaag 30540
gcaaatgctt ttatttgtac actctcgggt gattatttac ccccaccctt gccgtctgcg 30600
ccgtttaaaa atcaaagggg ttctgccgcg catcgctatg cgccactggc agggacacgt 30660
tgcgatactg gtgtttagtg ctccacttaa actcaggcac aaccatccgc ggcagctcgg 30720
tgaagttttc actccacagg ctgcgcacca tcaccaacgc gtttagcagg tcgggcgccg 30780
atatcttgaa gtcgcagttg gggcctccgc cctgcgcgcg cgagttgcga tacacagggt 30840
tgcagcactg gaacactatc agcgccgggt ggtgcacgct ggccagcacg ctcttgtcgg 30900
agatcagatc cgcgtccagg tcctccgcgt tgctcagggc gaacggagtc aactttggta 30960
gctgccttcc caaaaagggc gcgtgcccag gctttgagtt gcactcgcac cgtagtggca 31020
tcaaaaggtg accgtgcccg gtctgggcgt taggatacag cgcctgcata aaagccttga 31080
tctgcttaaa agccacctga gcctttgcgc cttcagagaa gaacatgccg caagacttgc 31140
cggaaaactg attggccgga caggccgcgt cgtgcacgca gcaccttgcg tcggtgttgg 31200
agatctgcac cacatttcgg ccccaccggt tcttcacgat cttggccttg ctagactgct 31260
ccttcagcgc gcgctgcccg ttttcgctcg tcacatccat ttcaatcacg tgctccttat 31320
ttatcataat gcttccgtgt agacacttaa gctcgccttc gatctcagcg cagcggtgca 31380
gccacaacgc gcagcccgtg ggctcgtgat gcttgtaggt cacctctgca aacgactgca 31440
ggtacgcctg caggaatcgc cccatcatcg tcacaaaggt cttgttgctg gtgaaggtca 31500
gctgcaaccc gcggtgctcc tcgttcagcc aggtcttgca tacggccgcc agagcttcca 31560
cttggtcagg cagtagtttg aagttcgcct ttagatcgtt atccacgtgg tacttgtcca 31620
tcagcgcgcg cgcagcctcc atgcccttct cccacgcaga cacgatcggc acactcagcg 31680
ggttcatcac cgtaatttca ctttccgctt cgctgggctc ttcctcttcc tcttgcgtcc 31740
gcataccacg cgccactggg tcgtcttcat tcagccgccg cactgtgcgc ttacctcctt 31800
tgccatgctt gattagcacc ggtgggttgc tgaaacccac catttgtagc gccacatctt 31860
ctctttcttc ctcgctgtcc acgattacct ctggtgatgg cgggcgctcg ggcttgggag 31920
aagggcgctt ctttttcttc ttgggcgcaa tggccaaatc cgccgccgag gtcgatggcc 31980
gcgggctggg tgtgcgcggc accagcgcgt cttgtgatga gtcttcctcg tcctcggact 32040
cgatacgccg cctcatccgc ttttttgggg gcgcccgggg aggcggcggc gacggggacg 32100
gggacgacac gtcctccatg gttgggggac gtcgcgccgc accgcgtccg cgctcggggg 32160
tggtttcgcg ctgctcctct tcccgactgg ccatttcctt ctcctatagg cagaaaaaga 32220
tcatggagtc agtcgagaag aaggacagcc taaccgcccc ctctgagttc gccaccaccg 32280
cctccaccga tgccgccaac gcgcctacca ccttccccgt cgaggcaccc ccgcttgagg 32340
aggaggaagt gattatcgag caggacccag gttttgtaag cgaagacgac gaggaccgct 32400
cagtaccaac agaggataaa aagcaagacc aggacaacgc agaggcaaac gaggaacaag 32460

```
tcgggcgggg ggacgaaagg catggcgact acctagatgt gggagacgac gtgctgttga  32520
agcatctgca gcgccagtgc gccattatct gcgacgcgtt gcaagagcgc agcgatgtgc  32580
ccctcgccat agcggatgtc agccttgcct acgaacgcca cctattctca ccgcgcgtac  32640
cccccaaacg ccaagaaaac ggcacatgcg agcccaaccc gcgcctcaac ttctaccccg  32700
tatttgccgt gccagaggtg cttgccacct atcacatctt tttccaaaac tgcaagatac  32760
ccctatcctg ccgtgccaac cgcagccgag cggacaagca gctggccttg cggcagggcg  32820
ctgtcatacc tgatatcgcc tcgctcaacg aagtgccaaa aatctttgag ggtcttggac  32880
gcgacgagaa gcgcgcggca aacgctctgc aacaggaaaa cagcgaaaat gaaagtcact  32940
ctggagtgtt ggtggaactc gagggtgaca acgcgcgcct agccgtacta aaacgcagca  33000
tcgaggtcac ccactttgcc tacccggcac ttaacctacc ccccaaggtc atgagcacag  33060
tcatgagtga gctgatcgtg cgccgtgcgc agcccctgga gagggatgca aatttgcaag  33120
aacaaacaga ggagggccta cccgcagttg gcgacgagca gctagcgcgc tggcttcaaa  33180
cgcgcgagcc tgccgacttg gaggagcgac gcaaactaat gatggccgca gtgctcgtta  33240
ccgtggagct tgagtgcatg cagcggttct ttgctgaccc ggagatgcag cgcaagctag  33300
aggaaacatt gcactacacc tttcgacagg gctacgtacg ccaggcctgc aagatctcca  33360
acgtggagct ctgcaacctg gtctcctacc ttggaatttt gcacgaaaac cgccttgggc  33420
aaaacgtgct tcattccacg ctcaagggcg aggcgcgccg cgactacgtc cgcgactgcg  33480
tttacttatt tctatgctac acctggcaga cggccatggg cgtttggcag cagtgcttgg  33540
aggagtgcaa cctcaaggag ctgcagaaac tgctaaagca aaacttgaag gacctatgga  33600
cggccttcaa cgagcgctcc gtggccgcgc acctggcgga catcattttc cccgaacgcc  33660
tgcttaaaac cctgcaacag ggtctgccag acttcaccag tcaaagcatg ttgcagaact  33720
ttaggaactt tatcctagag cgctcaggaa tcttgcccgc cacctgctgt gcacttccta  33780
gcgactttgt gcccattaag taccgcgaat gccctccgcc gctttggggc cactgctacc  33840
ttctgcagct agccaactac cttgcctacc actctgacat aatggaagac gtgagcggtg  33900
acggtctact ggagtgtcac tgtcgctgca acctatgcac cccgcaccgc tccctggttt  33960
gcaattcgca gctgcttaac gaaagtcaaa ttatcggtac ctttgagctg cagggtccct  34020
cgcctgacga aaagtccgcg gctccggggt tgaaactcac tccggggctg tggacgtcgg  34080
cttaccttcg caaatttgta cctgaggact accacgccca cgagattagg ttctacgaag  34140
accaatcccg cccgccaaat gcggagctta ccgcctgcgt cattacccag ggccacattc  34200
ttggccaatt gcaagccatc aacaaagccc gccaagagtt tctgctacga aagggacggg  34260
gggtttactt ggacccccag tccggcgagg agctcaaccc aatccccccg ccgccgcagc  34320
cctatcagca gcagccgcgg gcccttgctt cccaggatgg cacccaaaaa gaagctgcag  34380
ctgccgccgc cacccacgga cgaggaggaa tactgggaca gtcaggcaga ggaggttttg  34440
gacgaggagg aggaggacat gatggaagac tgggagagcc tagacgagga agcttccgag  34500
gtcgaagagg tgtcagacga aacaccgtca ccctcggtcg cattcccctc gccggcgccc  34560
cagaaatcgg caaccggttc cagcatggct acaacctccg ctcctcaggc gccgccggca  34620
ctgcccgttc gccgacccaa ccgtagatgg gacaccactg gaaccagggc cggtaagtcc  34680
aagcagccgc cgccgttagc ccaagagcaa caacagcgcc aaggctaccg ctcatggcgc  34740
gggcacaaga acgccatagt tgcttgcttg caagactgtg ggggcaacat ctccttcgcc  34800
```

cgccgctttc ttctctacca tcacggcgtg gccttccccc gtaacatcct gcattactac 34860
cgtcatctct acagcccata ctgcaccggc ggcagcggca gcggcagcaa cagcagcggc 34920
cacacagaag caaaggcgac cggatagcaa gactctgaca aagcccaaga aatccacagc 34980
ggcggcagca gcaggaggag gagcgctgcg tctggcgccc aacgaacccg tatcgacccg 35040
cgagcttaga aacaggattt ttcccactct gtatgctata tttcaacaga gcaggggcca 35100
agaacaagag ctgaaaataa aaaacaggtc tctgcgatcc ctcacccgca gctgcctgta 35160
tcacaaaagc gaagatcagc ttcggcgcac gctggaagac gcggaggctc tcttcagtaa 35220
atactgcgcg ctgactctta aggactagtt tcgcgccctt tctcaaattt aagcgcgaaa 35280
actacgtcat ctccagcggc cacacccggc gccagcacct gtcgtcagcg ccattatgag 35340
caaggaaatt cccacgccct acatgtggag ttaccagcca caaatgggac ttgcggctgg 35400
agctgcccaa gactactcaa cccgaataaa ctacatgagc gcgggacccc acatgatatc 35460
ccgggtcaac ggaatccgcg cccaccgaaa ccgaattctc ttggaacagg cggctattac 35520
caccacacct cgtaataacc ttaatccccg tagttggccc gctgccctgg tgtaccagga 35580
aagtcccgct cccaccactg tggtacttcc cagagacgcc caggccgaag ttcagatgac 35640
taactcaggg gcgcagcttg cgggcggctt tcgtcacagg gtgcggtcgc ccgggcaggg 35700
tataactcac ctgacaatca gagggcgagg tattcagctc aacgacgagt cggtgagctc 35760
ctcgcttggt ctccgtccgg acgggacatt tcagatcggc ggcgccggcc gtccttcatt 35820
cacgcctcgt caggcaatcc taactctgca gacctcgtcc tctgagccgc gctctggagg 35880
cattggaact ctgcaattta ttgaggagtt tgtgccatcg gtctacttta acccctctc 35940
gggacctccc ggccactatc cggatcaatt tattcctaac tttgacgcgg taaaggactc 36000
ggcggacggc tacgactgaa tgttaagtgg agaggcagag caactgcgcc tgaaacacct 36060
ggtccactgt cgccgccaca agtgctttgc ccgcgactcc ggtgagtttt gctactttga 36120
attgcccgag gatcatatcg agggcccggc gcacggcgtc cggcttaccg cccagggaga 36180
gcttgcccgt agcctgattc gggagtttac ccagcgcccc ctgctagttg agcgggacag 36240
gggaccctgt gttctcactg tgatttgcaa ctgtcctaac cttggattac atcaagatcc 36300
tctagttata actagagtac ccggggatct tattcccttt aactaataaa aaaaaataat 36360
aaagcatcac ttacttaaaa tcagttagca aatttctgtc cagtttattc agcagcacct 36420
ccttgccctc ctcccagctc tggtattgca gcttcctcct ggctgcaaac tttctccaca 36480
atctaaatgg aatgtcagtt tcctcctgtt cctgtccatc cgcacccact atcttcatgt 36540
tgttgcagat gaagcgcgca agaccgtctg aagatacctt caaccccgtg tatccatatg 36600
acacggaaac cggtcctcca actgtgcctt ttcttactcc tccctttgta tcccccaatg 36660
ggtttcaaga gagtcccccct ggggtactct ctttgcgcct atccgaacct ctagttacct 36720
ccaatggcat gcttgcgctc aaaatgggca acggcctctc tctggacgag gccggcaacc 36780
ttacctccca aaatgtaacc actgtgagcc cacctctcaa aaaaaccaag tcaaacataa 36840
acctggaaat atctgcaccc ctcacagtta cctcagaagc cctaactgtg gctgccgccg 36900
cacctctaat ggtcgcgggc aacacactca ccatgcaatc acaggccccg ctaaccgtgc 36960
acgactccaa acttagcatt gccacccaag gacccctcac agtgtcagaa ggaaagctag 37020
ccctgcaaac atcaggcccc ctcaccacca ccgatagcag tacccttact atcactgcct 37080
cacccccctct aactactgcc actggtagct tgggcattga cttgaaagag cccatttata 37140
cacaaaatgg aaaactagga ctaaagtacg gggctccttt gcatgtaaca gacgacctaa 37200

```
acactttgac cgtagcaact ggtccaggtg tgactattaa taatacttcc ttgcaaacta  37260

aagttactgg agccttgggt tttgattcac aaggcaatat gcaacttaat gtagcaggag  37320

gactaaggat tgattctcaa aacagacgcc ttatacttga tgttagttat ccgtttgatg  37380

ctcaaaacca actaaatcta agactaggac agggccctct tttataaac tcagcccaca  37440

acttggatat taactacaac aaaggccttt acttgtttac agcttcaaac aattccaaaa  37500

agcttgaggt taacctaagc actgccaagg ggttgatgtt tgacgctaca gccatagcca  37560

ttaatgcagg agatgggctt gaatttggtt cacctaatgc accaaacaca aatcccctca  37620

aaacaaaaat tggccatggc ctagaatttg attcaaacaa ggctatggtt cctaaactag  37680

gaactggcct tagttttgac agcacaggtg ccattacagt aggaaacaaa aataatgata  37740

agctaacttt gtggaccaca ccagctccat ctcctaactg tagactaaat gcagagaaag  37800

atgctaaact cactttggtc ttaacaaaat gtggcagtca aatacttgct acagtttcag  37860

ttttggctgt taaaggcagt ttggctccaa tatctggaac agttcaaagt gctcatctta  37920

ttataagatt tgacgaaaat ggagtgctac taaacaattc cttcctggac ccagaatatt  37980

ggaactttag aaatggagat cttactgaag gcacagccta tacaaacgct gttggattta  38040

tgcctaacct atcagcttat ccaaaatctc acggtaaaac tgccaaaagt aacattgtca  38100

gtcaagttta cttaaacgga gacaaaacta aacctgtaac actaaccatt acactaaacg  38160

gtacacagga aacaggagac acaactccaa gtgcatactc tatgtcattt tcatgggact  38220

ggtctggcca caactacatt aatgaaatat ttgccacatc ctcttacact ttttcataca  38280

ttgcccaaga ataaagaatc gtttgtgtta tgtttcaacg tgtttatttt tcaattgcag  38340

aaaatttcaa gtcatttttc attcagtagt atagccccac caccacatag cttatacaga  38400

tcaccgtacc ttaatcaaac                                              38420
```

<210> SEQ ID NO 2
<211> LENGTH: 12741
<212> TYPE: DNA
<213> ORGANISM: Artificial Sequence
<220> FEATURE:
<223> OTHER INFORMATION: Synthetic polynucleotide

<400> SEQUENCE: 2

```
aatgtagtct tatgcaatac tcttgtagtc ttgcaacatg gtaacgatga gttagcaaca     60

tgccttacaa ggagagaaaa agcaccgtgc atgccgattg gtggaagtaa ggtggtacga    120

tcgtgcctta ttaggaaggc aacagacggg tctgacatgg attggacgaa ccactgaatt    180

gccgcattgc agagatattg tatttaagtg cctagctcga tacataaacg ggtctctctg    240

gttagaccag atctgagcct gggagctctc tggctaacta gggaacccac tgcttaagcc    300

tcaataaagc ttgccttgag tgcttcaagt agtgtgtgcc cgtctgttgt gtgactctgg    360

taactagaga tccctcagac ccttttagtc agtgtggaaa atctctagca gtggcgcccg    420

aacagggact tgaaagcgaa agggaaacca gaggagctct ctcgacgcag gactcggctt    480

gctgaagcgc gcacggcaag aggcgagggg cggcgactgg tgagtacgcc aaaaattttg    540

actagcggag gctagaagga gagagatggg tgcgagagcg tcagtattaa gcgggggaga    600

attagatcgc gatgggaaaa aattcggtta aggccagggg gaaagaaaaa atataaatta    660

aaacatatag tatgggcaag cagggagcta gaacgattcg cagttaatcc tggcctgtta    720

gaaacatcag aaggctgtag acaaatactg ggacagctac aaccatccct tcagacagga    780
```

-continued

```
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgatt   1800
gggcccgaga tctcgcgcgc gaggcctgcc atgggcatgc ctgcaggtcg atgcgtggcc   1860
ggcctaggat ccatatggta ccggtaaatg gcccgcctgg ctgaccgccc aacgaccccc   1920
gcccattgac gtcaataatg acgtatgttc ccatagtaac gccaataggg actttccatt   1980
gacgtcaatg ggtggagtat ttacggtaaa ctgcccactt ggcagtacat caagtgtatc   2040
atatgccaag tacgccccct attgacgtca atgacggtaa atggcccgcc tggcattatg   2100
cccagtacat gaccttatgg gactttccta cttggcagta catctagtat tagtcatcgc   2160
tattaccatg gtgatgcggt tttggcagta catcaatggg cgtggatagc ggtttgactc   2220
acggggattt ccaagtctcc accccattga cgtcaatggg agtttgtttt ggcaccaaaa   2280
tcaacgggac tttccaaaat gtcgtaacaa ctccgcccca ttgacgcaaa tgggcggtag   2340
gcgtgtacgg tgggaggtct atataagcag agctcgttta gtgaaccgtc agatcgcctg   2400
gagacgccat ccacgctgtt ttgacctcca tagaagacac cgggaccgat ccagcctccg   2460
cggccgggaa cggtgcattg gaacgcggat tccccgtgcc aagagtgacg taagtaccgc   2520
ctatagactc tataggcaca cccctttggc tcttatgcat gaattaatac gactcactat   2580
agggagacag actgttcctt tcctgggtct tttctgcagg ctagccccac catgccgcgc   2640
gctccccgct gccgagccgt gcgctccctg ctgcgcagcc actaccgcga ggtgctgccg   2700
ctggccacgt tcgtgcggcg cctggggccc cagggctggc ggctggtgca gcgcggggac   2760
ccggcggctt tccgcgcgct ggtggcccag tgcctggtgt gcgtgccctg ggacgcacgg   2820
ccgcccccccg ccgccccctc cttccgccag gtgtcctgcc tgaaggagct ggtggcccga   2880
gtgctgcaga ggctgtgcga gcgcggcgcg aagaacgtgc tggccttcgg cttcgcgctg   2940
ctggacgggg cccgcggggg ccccccccgag gccttcacca ccagcgtgcg cagctacctg   3000
cccaacacgg tgaccgacgc actgcggggg agcggggcgt gggggctgct gttgcgccgc   3060
gtgggcgacg acgtgctggt tcacctgctg gcacgctgcg cgctctttgt gctggtggct   3120
cccagctgcg cctaccaggt gtgcgggccg ccgctgtacc agctcggcgc tgccactcag   3180
```

```
gcccggcccc cgccacacgc tagtggaccc cgaaggcgtc tgggatgcga acgggcctgg   3240
aaccatagcg tcagggaggc cggggtcccc ctgggcctgc cagccccggg tgcgaggagg   3300
cgcgggggca gtgccagccg aagtctgccg ttgcccaaga ggcccaggcg tggcgctgcc   3360
cctgagccgg agcggacgcc cgttgggcag gggtcctggg cccacccggg caggacgcgt   3420
ggaccgagtg accgtggttt ctgtgtggtg tcacctgcca gacccgccga agaagccacc   3480
tctttggagg gtgcgctctc tggcacgcgc cactcccacc catccgtggg ccgccagcac   3540
cacgcgggcc ccccatccac atcgcggcca ccacgtccct gggacacgcc ttgtcccccg   3600
gtgtacgccg agaccaagca cttcctctac tcctcaggcg acaaggagca gctgcggccc   3660
tccttcctac tcagctctct gaggcccagc ctgactggcg ctcggaggct cgtggagacc   3720
atctttctgg gttccaggcc ctggatgcca gggactcccc gcaggttgcc ccgcctgccc   3780
cagcgctact ggcaaatgcg gcccctgttt ctggagctgc ttgggaacca cgcgcagtgc   3840
ccctacgggg tgctcctcaa gacgcactgc ccgctgcgag ctgcggtcac cccagcagcc   3900
ggtgtctgtg cccgggagaa gccccagggc tctgtggcgg cccccgagga ggaggacaca   3960
gacccccgtc gcctggtgca gctgctccgc cagcacagca gcccctggca ggtgtacggc   4020
ttcgtgcggg cctgcctgcg ccggctggtg cccccaggcc tctggggctc caggcacaac   4080
gaacgccgct tcctcaggaa caccaagaag ttcatctccc tggggaagca tgccaagctc   4140
tcgctgcagg agctgacgtg gaagatgagc gtgcggggct gcgcttggct gcgcaggagc   4200
ccaggggttg gctgtgttcc ggccgcagag caccgtctgc gtgaggagat cctggccaag   4260
ttcctgcact ggctgatgag tgtgtacgtc gtcgagctgc tcaggtcttt cttttatgtc   4320
acggagacca cgtttcaaaa gaacaggctc tttttctacc ggaagagtgt ctggagcaag   4380
ttgcaaagca ttggaatcag acagcacttg aagagggtgc agctgcggga gctgtcggaa   4440
gcagaggtca ggcagcatcg ggaagccagg cccgccctgc tgacgtccag actccgcttc   4500
atccccaagc ctgacgggct gcggccgatt gtgaacatgg actacgtcgt gggagccaga   4560
acgttccgca gagaaaagag ggccgagcgt ctcacctcca gggtgaaggc actgttcagc   4620
gtgctcaact acgagcgggc gcggcgcccc ggcctcctgg gcgcctctgt gctgggcctg   4680
gacgatatcc acagggcctg gcgcaccttc gtgctgcgtg tgcgggccca ggacccgccg   4740
cctgagctgt actttgtcaa ggtggatgtg acgggcgcgt acgacaccat cccccaggac   4800
aggctcacgg aggtcatcgc cagcatcatc aaaccccaga acacgtactg cgtgcgtcgg   4860
tatgccgtgg tccagaaggc cgcccatggg cacgtccgca aggccttcaa gagccacgtc   4920
tctaccttga cagacctcca gccgtacatg cgacagttcg tggctcacct gcaggagacc   4980
agcccgctga gggatgccgt cgtcatcgag cagagctcct ccctgaatga ggccagcagt   5040
ggcctcttcg acgtcttcct acgcttcatg tgccaccacg ccgtgcgcat caggggcaag   5100
tcctacgtcc agtgccaggg gatcccgcag ggctccatcc tctccacgct gctctgcagc   5160
ctgtgctacg gcgacatgga gaacaagctg tttgcgggga ttcggcggga cgggctgctc   5220
ctgcgtttgg tggatgattt cttgttggtg acacctcacc tcacccacgc gaaaaccttc   5280
ctcaggaccc tggtccgagg tgtccctgag tatggctgcg tggtgaactt gcggaagaca   5340
gtggtgaact tccctgtaga agacgaggcc ctgggtggca cggcttttgt tcagatgccg   5400
gcccacggcc tattcccctg gtgcggcctg ctgctggata cccggaccct ggaggtgcag   5460
agcgactact ccagctatgc ccggacctcc atcagagcca gtctcacctt caaccgcggc   5520
```

```
ttcaaggctg ggaggaacat gcgtcgcaaa ctctttgggg tcttgcggct gaagtgtcac   5580
agcctgtttc tggatttgca ggtgaacagc ctccagacgg tgtgcaccaa catctacaag   5640
atcctcctgc tgcaggcgta caggtttcac gcatgtgtgc tgcagctccc atttcatcag   5700
caagtttgga agaaccccac atttttcctg cgcgtcatct ctgacacggc ctccctctgc   5760
tactccatcc tgaaagccaa gaacgcaggg atgtcgctgg gggccaaggg cgccgccggc   5820
cctctgccct ccgaggccgt gcagtggctg tgccaccaag cattcctgct caagctgact   5880
cgacaccgtg tcacctacgt gccactcctg ggtcactca ggacagccca gacgcagctg   5940
agtcggaagc tcccggggac gacgctgact gccctggagg ccgcagccaa cccggcactg   6000
ccctcagact tcaagaccat cctggactga gtcgaaactc gaggatccgg ctgtggaatg   6060
tgtgtcagtt agggtgtgga aagtccccag gctccccagc aggcagaagt atgcaaagca   6120
tgcatctcaa ttagtcagca accaggtgtg gaaagtcccc aggctcccca gcaggcagaa   6180
gtatgcaaag catgcatctc aattagtcag caaccatagt cccgccccta actccgccca   6240
tcccgcccct aactccgccc agttccgccc attctccgcc ccatggctga ctaatttttt   6300
ttatttatgc agaggccgag gccgcctcgg cctctgagct attccagaag tagtgaggag   6360
gcttttttgg aggccgtcgg ccgccacgac cggtgccgcc accatcccct gacccacgcc   6420
cctgacccct cacaaggaga cgaccttcca tgaccgagta caagcccacg gtgcgcctcg   6480
ccacccgcga cgacgtcccc cgggccgtac gcaccctcgc cgccgcgttc gccgactacc   6540
ctgcaacacg ccatacagtg gaccctgacc gccacatcga gcgggtcacc gagctgcaag   6600
aactcttcct cacgcgcgtc gggctcgaca tcggcaaggt gtgggtcgcg gacgacggcg   6660
ccgcggtggc ggtctggacc acgccggaga gcgtcgaagc gggggcggtg ttcgccgaga   6720
tcggcccgcg catggccgag ttgagcggtt cccggctggc cgcgcagcaa cagatggaag   6780
gcctcctggc gccgcaccgg cccaaggagc ccgcgtggtt cctggccacc gtcggcgtct   6840
cgcccgacca ccagggcaag ggtctgggca gcgccgtcgt gctccccgga gtggaggcgg   6900
ccgagcgcgc cggggtgccc gccttcctgg agacctccgc gccccgcaac ctccccttct   6960
acgagcggct cggcttcacc gtcaccgccg acgtcgaggt gcccgaagga ccgcgcacct   7020
ggtgcatgac ccgcaagccc ggtgcctgac gcccgcccca cgacccgcag cgcccgaccg   7080
aaaggagcgc acgaccccat gcatcgataa aataaaagat tttatttagt ctccagaaaa   7140
agggggggaat gaaagacccc acctgtaggt ttggcaagct aggcctatta atattccgga   7200
gtatacgtag ccggctaacg ttaacaaccg gtacgatgca ttagttatta atagtaatca   7260
attacggggt cattagttca tagcccatat atggagttcc gcgttacata acttacggta   7320
aatggcccgc ctggctgacc gcccaacgac ccccgcccat tgacgtcaat aatgacgtat   7380
gttcccatag taacgccaat agggactttc cattgacgtc aatgggtgga gtatttacgg   7440
taaactgccc acttggcagt acatcaagtg tatcatatgc caagtacgcc ccctattgac   7500
gtcaatgacg gtaaatggcc cgcctggcat tatgcccagt acatgacctt atgggacttt   7560
cctacttggc agtacatcta cgtattagtc atcgctatta ccatggtgat gcggttttgg   7620
cagtacatca atgggcgtgg atagcggttt gactcacggg gatttccaag tctccacccc   7680
attgacgtca atgggagttt gttttggcac caaaatcaac gggactttcc aaaatgtcgt   7740
aacaactccg ccccattgac gcaaatgggc ggtaggcgtg tacggtggga ggtctatata   7800
agcagagctg gtttagtgaa ccgtcagatc cgctagcgct accggactca gatctcgagc   7860
tcaagcttcg aattctgcag tcgacccacc atggctcttt caaacaagtt tatcggagat   7920
```

```
gacatgaaaa tgacctacca tatggatggc tgtgtcaatg ggcattactt taccgtcaaa   7980
ggtgaaggca gcgggaagcc atacgaaggg acgcagacct cgacttttaa agtcaccatg   8040
gccaacggtg ggccccttgc attctccttt gacatactat ctacagtgtt catgtatgga   8100
aatcgatgct ttactgcgta tcctaccagt atgcccgact atttcaaaca agcatttcct   8160
gacggaatgt catatgaaag gacttttacc tatgaagatg gaggagttgc tacagccagt   8220
tgggaaataa gccttaaagg caactgcttt gagcacaaat ccacgtttca tggagtgaac   8280
tttcctgctg atggacctgt gatggcgaag atgacaactg gttgggaccc atcttttgag   8340
aaaatgactg tctgcgatgg aatattgaag ggtgatgtca ccgcgttcct catgctgcaa   8400
ggaggtggca attacagatg ccaattccac acttcttaca agacaaaaaa accggtgacg   8460
atgccaccaa accatgcggt ggaacatcgc attgcgagga ccgaccttga caaaggtggc   8520
aacagtgttc agctgacgga gcacgctgtt gcacatataa cctctgttgt ccctttctag   8580
cggccgcgat aatcaacctc tggattacaa aatttgtgaa agattgactg gtattcttaa   8640
ctatgttgct ccttttacgc tatgtggata cgctgcttta atgcctttgt atcatgctat   8700
tgcttcccgt atggctttca ttttctcctc cttgtataaa tcctggttgc tgtctcttta   8760
tgaggagttg tggcccgttg tcaggcaacg tggcgtggtg tgcactgtgt ttgctgacgc   8820
aacccccact ggttggggca ttgccaccac ctgtcagctc ctttccggga ctttcgcttt   8880
ccccctccct attgccacgg cggaactcat cgccgcctgc cttgcccgct gctggacagg   8940
ggctcggctg ttgggcactg acaattccgt ggtgttgtcg gggaagctga cgtcctttcc   9000
atggctgctc gcctgtgttg ccacctggat tctgcgcggg acgtccttct gctacgtccc   9060
ttcggccctc aatccagcgg accttccttc ccgcggcctg ctgccggctc tgcggcctct   9120
tccgcgtctt cgccttcgcc ctcagacgag tcggatctcc ctttgggccg cctccccgca   9180
tcggacgcgt ggtaccttta agaccaatga cttacaaggc agctgtagat cttagccact   9240
ttttaaaaga aaagggggga ctggaagggc taattcactc ccaacgaaga caagatctgc   9300
tttttgcttg tactgggtct ctctggttag accagatctg agcctgggag ctctctggct   9360
aactagggaa cccactgctt aagcctcaat aaagcttgcc ttgagtgctt caagtagtgt   9420
gtgcccgtct gttgtgtgac tctggtaact agagatccct cagacccttt tagtcagtgt   9480
ggaaaatctc tagcagtagt agttcatgtc atcttattat tcagtattta taacttgcaa   9540
agaaatgaat atcagagagt gagaggaact tgtttattgc agcttataat ggttacaaat   9600
aaagcaatag catcacaaat ttcacaaata aagcattttt ttcactgcat tctagttgtg   9660
gtttgtccaa actcatcaat gtatcttatc atgtctggct ctagctatcc cgcccctaac   9720
tccgcccatc ccgcccctaa ctccgcccag ttccgcccat tctccgcccc atggctgact   9780
aatttttttt atttatgcag aggccgaggc cgcctcggcc tctgagctat tccagaagta   9840
gtgaggaggc ttttttggag gcctagggac gtacccaatt cgccctatag tgagtcgtat   9900
tacgcgcgct cactggccgt cgttttacaa cgtcgtgact gggaaaaccc tggcgttacc   9960
caacttaatc gccttgcagc acatccccct ttcgccagct ggcgtaatag cgaagaggcc  10020
cgcaccgatc gcccttccca acagttgcgc agcctgaatg gcgaatggga cgcgccctgt  10080
agcggcgcat taagcgcggc gggtgtggtg gttacgcgca gcgtgaccgc tacacttgcc  10140
agcgccctag cgcccgctcc tttcgctttc ttcccttcct ttctcgccac gttcgccggc  10200
tttccccgtc aagctctaaa tcgggggctc cctttagggt tccgatttag tgctttacgg  10260
```

```
cacctcgacc ccaaaaaact tgattagggt gatggttcac gtagtgggcc atcgccctga  10320
tagacggttt ttcgcccttt gacgttggag tccacgttct ttaatagtgg actcttgttc  10380
caaactggaa caacactcaa ccctatctcg gtctattctt ttgatttata agggattttg  10440
ccgatttcgg cctattggtt aaaaaatgag ctgatttaac aaaaatttaa cgcgaatttt  10500
aacaaaatat taacgcttac aatttaggtg gcacttttcg gggaaatgtg cgcggaaccc  10560
ctatttgttt atttttctaa atacattcaa atatgtatcc gctcatgaga caataaccct  10620
gataaatgct tcaataatat tgaaaaagga agagtatgag tattcaacat ttccgtgtcg  10680
cccttattcc cttttttgcg gcattttgcc ttcctgtttt tgctcaccca gaaacgctgg  10740
tgaaagtaaa agatgctgaa gatcagttgg gtgcacgagt gggttacatc gaactggatc  10800
tcaacagcgg taagatcctt gagagttttc gccccgaaga acgttttcca atgatgagca  10860
cttttaaagt tctgctatgt ggcgcggtat tatcccgtat tgacgccggg caagagcaac  10920
tcggtcgccg catacactat tctcagaatg acttggttga gtactcacca gtcacagaaa  10980
agcatcttac ggatggcatg acagtaagag aattatgcag tgctgccata accatgagtg  11040
ataacactgc ggccaactta cttctgacaa cgatcggagg accgaaggag ctaaccgctt  11100
ttttgcacaa catgggggat catgtaactc gccttgatcg ttgggaaccg gagctgaatg  11160
aagccatacc aaacgacgag cgtgacacca cgatgcctgt agcaatggca acaacgttgc  11220
gcaaactatt aactggcgaa ctacttactc tagcttcccg gcaacaatta atagactgga  11280
tggaggcgga taaagttgca ggaccacttc tgcgctcggc ccttccggct ggctggttta  11340
ttgctgataa atctggagcc ggtgagcgtg ggtctcgcgg tatcattgca gcactggggc  11400
cagatggtaa gccctcccgt atcgtagtta tctacacgac ggggagtcag gcaactatgg  11460
atgaacgaaa tagacagatc gctgagatag gtgcctcact gattaagcat tggtaactgt  11520
cagaccaagt ttactcatat atactttaga ttgatttaaa acttcatttt taatttaaaa  11580
ggatctaggt gaagatcctt tttgataatc tcatgaccaa aatcccttaa cgtgagtttt  11640
cgttccactg agcgtcagac cccgtagaaa agatcaaagg atcttcttga gatccttttt  11700
ttctgcgcgt aatctgctgc ttgcaaacaa aaaaaccacc gctaccagcg gtggtttgtt  11760
tgccggatca agagctacca actctttttc cgaaggtaac tggcttcagc agagcgcaga  11820
taccaaatac tgttcttcta gtgtagccgt agttaggcca ccacttcaag aactctgtag  11880
caccgcctac atacctcgct ctgctaatcc tgttaccagt ggctgctgcc agtggcgata  11940
agtcgtgtct taccgggttg gactcaagac gatagttacc ggataaggcg cagcggtcgg  12000
gctgaacggg gggttcgtgc acacagccca gcttggagcg aacgacctac accgaactga  12060
gatacctaca gcgtgagcta tgagaaagcg ccacgcttcc cgaagggaga aaggcggaca  12120
ggtatccggt aagcggcagg gtcggaacag gagagcgcac gagggagctt ccagggggaa  12180
acgcctggta tctttatagt cctgtcgggt ttcgccacct ctgacttgag cgtcgatttt  12240
tgtgatgctc gtcagggggg cggagcctat ggaaaaacgc cagcaacgcg gcctttttac  12300
ggttcctggc cttttgctgg ccttttgctc acatgttctt tcctgcgtta tcccctgatt  12360
ctgtggataa ccgtattacc gcctttgagt gagctgatac cgctcgccgc agccgaacga  12420
ccgagcgcag cgagtcagtg agcgaggaag cggaagagcg cccaatacgc aaaccgcctc  12480
tccccgcgcg ttggccgatt cattaatgca gctggcacga caggtttccc gactggaaag  12540
cgggcagtga gcgcaacgca attaatgtga gttagctcac tcattaggca ccccaggctt  12600
tacactttat gcttccggct cgtatgttgt gtggaattgt gagcggataa caatttcaca  12660
```

```
caggaaacag ctatgaccat gattacgcca agcgcgcaat taaccctcac taaagggaac  12720

aaaagctgga gctgcaagct t                                            12741


<210> SEQ ID NO 3
<211> LENGTH: 11626
<212> TYPE: DNA
<213> ORGANISM: Artificial Sequence
<220> FEATURE:
<223> OTHER INFORMATION: Synthetic polynucleotide

<400> SEQUENCE: 3

aatgtagtct tatgcaatac tcttgtagtc ttgcaacatg gtaacgatga gttagcaaca     60

tgccttacaa ggagagaaaa agcaccgtgc atgccgattg gtggaagtaa ggtggtacga    120

tcgtgcctta ttaggaaggc aacagacggg tctgacatgg attggacgaa ccactgaatt    180

gccgcattgc agagatattg tatttaagtg cctagctcga tacataaacg ggtctctctg    240

gttagaccag atctgagcct gggagctctc tggctaacta gggaacccac tgcttaagcc    300

tcaataaagc ttgccttgag tgcttcaagt agtgtgtgcc cgtctgttgt gtgactctgg    360

taactagaga tccctcagac ccttttagtc agtgtggaaa atctctagca gtggcgcccg    420

aacagggact tgaaagcgaa agggaaacca gaggagctct ctcgacgcag gactcggctt    480

gctgaagcgc gcacggcaag aggcgagggg cggcgactgg tgagtacgcc aaaaattttg    540

actagcggag gctagaagga gagagatggg tgcgagagcg tcagtattaa gcgggggaga    600

attagatcgc gatgggaaaa aattcggtta aggccagggg gaaagaaaaa atataaatta    660

aaacatatag tatgggcaag cagggagcta gaacgattcg cagttaatcc tggcctgtta    720

gaaacatcag aaggctgtag acaaatactg ggacagctac aaccatccct tcagacagga    780

tcagaagaac ttagatcatt atataataca gtagcaaccc tctattgtgt gcatcaaagg    840

atagagataa aagacaccaa ggaagcttta gacaagatag aggaagagca aaacaaaagt    900

aagaccaccg cacagcaagc ggccgctgat cttcagacct ggaggaggag atatgaggga    960

caattggaga agtgaattat ataaatataa agtagtaaaa attgaaccat taggagtagc   1020

acccaccaag gcaaagagaa gagtggtgca gagagaaaaa agagcagtgg gaataggagc   1080

tttgttcctt gggttcttgg gagcagcagg aagcactatg ggcgcagcgt caatgacgct   1140

gacggtacag gccagacaat tattgtctgg tatagtgcag cagcagaaca atttgctgag   1200

ggctattgag gcgcaacagc atctgttgca actcacagtc tggggcatca agcagctcca   1260

ggcaagaatc ctggctgtgg aaagatacct aaaggatcaa cagctcctgg ggatttgggg   1320

ttgctctgga aaactcattt gcaccactgc tgtgccttgg aatgctagtt ggagtaataa   1380

atctctggaa cagatttgga atcacacgac ctggatggag tgggacagag aaattaacaa   1440

ttacacaagc ttaatacact ccttaattga agaatcgcaa aaccagcaag aaaagaatga   1500

acaagaatta ttggaattag ataaatgggc aagtttgtgg aattggttta acataacaaa   1560

ttggctgtgg tatataaaat tattcataat gatagtagga ggcttggtag gtttaagaat   1620

agtttttgct gtactttcta tagtgaatag agttaggcag ggatattcac cattatcgtt   1680

tcagacccac ctcccaaccc cgaggggacc cgacaggccc gaaggaatag aagaagaagg   1740

tggagagaga gacagagaca gatccattcg attagtgaac ggatctcgac ggtatcgata   1800

ctagtaattt ttctgcagaa aacgtacccg gggatcctct aggatcccac cgaaaggttg   1860

ctccttaaca caggctaagg accagcttct ttgggagaga acagacgcag ggcgggaggg   1920
```

```
gaaaaaggga gaggcagacg tcacttcccc ttggcggctc tggcagcaga ttggtcggtt   1980
gagtggcaga aaggcagacg gggactgggc aaggcactgt cggtgacatc acggacaggg   2040
cgacttctat gtagatgagg cagcgcagag gctgctgctt cgccacttgc tgcttcgcca   2100
cgaaggagtt cccgtgccct gggagcgggt tcaggaccgc ggatcggaag tgagaatccc   2160
agctgtgtgt cagggctgga aagggctcgg gagtgcgcgg ggcaagtgac cgtgtgtgta   2220
aagagtgagg cgtatgaggc tgtgtcgggg cagagcccga agatccgggt tgcggagggt   2280
gggcctggga ggggtggtgg ccattttttg tctaacccta actgagaagg gcgtaggcgc   2340
cgtgcttttg ctccccgcgc gctgtttttc tcgctgactt tcagcgggcg gaaaagcctc   2400
ggcctgccgc cttccaccgt tcattctaga gcaaacaaaa aatgtcagct gctggcccgt   2460
tcgcccctcc cggggacctg cggcgggtcg cctgcccagc ccccgaaccc cgcctggagg   2520
ccgcggtcgg cccggggctt ctccggaggc acccactgcc accgcgaaga gttgggctct   2580
gtcagccgcg ggtctctcgg gggcgagggc gaggttcagg cctttcaggc cgcaggaaga   2640
ggaacggagc gagtccccgc gcgcggcgcg attccctgag ctgtgggacg tgcacccagg   2700
actcggctca cacatgcagt tcgctttcct gttggtgggg ggaacgccga tcgtgcgcat   2760
ccgtcacccc tcgccggcaa tgggggcttg tgaacccccca aacctgactg actgggccag   2820
tgtgctgcaa attggcagga gacgtgaagg cacctccaaa gtcgactttc tggagtttca   2880
aaaacagacc gtacatgtcc gcggtcgcga cgtacctacc gggtagggga ggcgcttttc   2940
ccaaggcagt ctggagcatg cgctttagca gccccgctgg gcacttggcg ctacacaagt   3000
ggcctctggc ctcgcacaca ttccacatcc accggtaggc gccaaccggc tccgttcttt   3060
ggtggcccct tcgcgccacc ttctactcct cccctagtca ggaagttccc ccccgccccg   3120
cagctcgcgt cgtgcaggac gtgacaaatg gaagtagcac gtctcactag tctcgtgcag   3180
atggacagca ccgctgagca atggaagcgg gtaggccttt ggggcagcgg ccaatagcag   3240
ctttgctcct tcgctttctg ggctcagagg ctgggaaggg gtgggtccgg gggcgggctc   3300
aggggcgggc tcaggggcgg ggcgggcgcc cgaagtcctc cggaggcccg gcattctgca   3360
cgcttcaaaa gcgcacgtct gccgcgctgt tctcctcttc ctcatctccg ggcctttcga   3420
ctctagacac gtgttgacaa ttaatcatcg gcatagtata tcggcatagt ataatacgac   3480
aaggtgagga actaaaccat ggccaagcct ttgtctcaag aagaatccac cctcattgaa   3540
agagcaacgg ctacaatcaa cagcatcccc atctctgaag actacagcgt cgccagcgca   3600
gctctctcta gcgacggccg catcttcact ggtgtcaatg tatatcattt tactgggggga   3660
ccttgtgcag aactcgtggt gctgggcact gctgctgctg cggcagctgg caacctgact   3720
tgtatcgtcg cgatcggaaa tgagaacagg ggcatcttga gcccctgcgg acggtgccga   3780
caggtgcttc tcgatctgca tcctgggatc aaagccatag tgaaggacag tgatggacag   3840
ccgacggcag ttgggattcg tgaattgctg ccctctggtt atgtgtggga gggctaagca   3900
caattcgagc tcggtacgcg tatcgatggc gccagctgca ggcggccgcc atatgcatcc   3960
taggcctatt aatattccgg agtatacgta gccggctaac gttaacaacc ggtacgatgc   4020
attagttatt aatagtaatc aattacgggg tcattagttc atagcccata tatggagttc   4080
cgcgttacat aacttacggt aaatggcccg cctggctgac cgcccaacga cccccgccca   4140
ttgacgtcaa taatgacgta tgttcccata gtaacgccaa tagggacttt ccattgacgt   4200
caatgggtgg agtatttacg gtaaactgcc cacttggcag tacatcaagt gtatcatatg   4260
ccaagtacgc cccctattga cgtcaatgac ggtaaatggc ccgcctggca ttatgcccag   4320
```

```
tacatgacct tatgggactt tcctacttgg cagtacatct acgtattagt catcgctatt   4380
accatggtga tgcggttttg gcagtacatc aatgggcgtg gatagcggtt tgactcacgg   4440
ggatttccaa gtctccaccc cattgacgtc aatgggagtt tgttttggca ccaaaatcaa   4500
cgggactttc caaaatgtcg taacaactcc gccccattga cgcaaatggg cggtaggcgt   4560
gtacggtggg aggtctatat aagcagagct ggtttagtga accgtcagat ccgctagccc   4620
caccatgccg cgcgctcccc gctgccgagc cgtgcgctcc ctgctgcgca gccactaccg   4680
cgaggtgctg ccgctggcca cgttcgtgcg gcgcctgggg ccccagggct ggcggctggt   4740
gcagcgcggg gacccggcgg ctttccgcgc gctggtggcc cagtgcctgg tgtgcgtgcc   4800
ctgggacgca cggccgcccc ccgccgcccc ctccttccgc caggtgtcct gcctgaagga   4860
gctggtggcc cgagtgctgc agaggctgtg cgagcgcggc gcgaagaacg tgctggcctt   4920
cggcttcgcg ctgctggacg gggcccgcgg gggccccccc gaggccttca ccaccagcgt   4980
gcgcagctac ctgcccaaca cggtgaccga cgcactgcgg gggagcgggg cgtgggggct   5040
gctgttgcgc cgcgtgggcg acgacgtgct ggttcacctg ctggcacgct gcgcgctctt   5100
tgtgctggtg gctcccagct gcgcctacca ggtgtgcggg ccgccgctgt accagctcgg   5160
cgctgccact caggcccggc ccccgccaca cgctagtgga ccccgaaggc gtctgggatg   5220
cgaacgggcc tggaaccata gcgtcaggga ggccggggtc cccctgggcc tgccagcccc   5280
gggtgcgagg aggcgcgggg gcagtgccag ccgaagtctg ccgttgccca agaggcccag   5340
gcgtggcgct gcccctgagc cggagcggac gcccgttggg caggggtcct gggcccaccc   5400
gggcaggacg cgtggaccga gtgaccgtgg tttctgtgtg gtgtcacctg ccagacccgc   5460
cgaagaagcc acctctttgg agggtgcgct ctctggcacg cgccactccc acccatccgt   5520
gggccgccag caccacgcgg gcccccccatc cacatcgcgg ccaccacgtc cctgggacac   5580
gccttgtccc ccggtgtacg ccgagaccaa gcacttcctc tactcctcag gcgacaagga   5640
gcagctgcgg ccctccttcc tactcagctc tctgaggccc agcctgactg gcgctcggag   5700
gctcgtggag accatctttc tgggttccag gccctggatg ccagggactc cccgcaggtt   5760
gccccgcctg ccccagcgct actggcaaat gcggcccctg tttctggagc tgcttgggaa   5820
ccacgcgcag tgcccctacg gggtgctcct caagacgcac tgcccgctgc gagctgcggt   5880
caccccagca gccggtgtct gtgcccggga gaagccccag ggctctgtgg cggcccccga   5940
ggaggaggac acagaccccc gtcgcctggt gcagctgctc cgccagcaca gcagcccctg   6000
gcaggtgtac ggcttcgtgc gggcctgcct gcgccggctg gtgcccccag gcctctgggg   6060
ctccaggcac aacgaacgcc gcttcctcag gaacaccaag aagttcatct ccctggggaa   6120
gcatgccaag ctctcgctgc aggagctgac gtggaagatg agcgtgcggg gctgcgcttg   6180
gctgcgcagg agcccagggg ttggctgtgt tccggccgca gagcaccgtc tgcgtgagga   6240
gatcctggcc aagttcctgc actggctgat gagtgtgtac gtcgtcgagc tgctcaggtc   6300
tttcttttat gtcacggaga ccacgtttca aaagaacagg ctcttttct accggaagag   6360
tgtctggagc aagttgcaaa gcattggaat cagacagcac ttgaagaggg tgcagctgcg   6420
ggagctgtcg gaagcagagg tcaggcagca tcgggaagcc aggcccgccc tgctgacgtc   6480
cagactccgc ttcatcccca agcctgacgg gctgcggccg attgtgaaca tggactacgt   6540
cgtgggagcc agaacgttcc gcagagaaaa gagggccgag cgtctcacct ccagggtgaa   6600
ggcactgttc agcgtgctca actacgagcg ggcgcggcgc cccggcctcc tgggcgcctc   6660
```

```
tgtgctgggc ctggacgata tccacagggc ctggcgcacc ttcgtgctgc gtgtgcgggc   6720
ccaggacccg ccgcctgagc tgtactttgt caaggtggat gtgacgggcg cgtacgacac   6780
catcccccag gacaggctca cggaggtcat cgccagcatc atcaaacccc agaacacgta   6840
ctgcgtgcgt cggtatgccg tggtccagaa ggccgcccat gggcacgtcc gcaaggcctt   6900
caagagccac gtctctacct tgacagacct ccagccgtac atgcgacagt tcgtggctca   6960
cctgcaggag accagcccgc tgagggatgc cgtcgtcatc gagcagagct cctccctgaa   7020
tgaggccagc agtggcctct tcgacgtctt cctacgcttc atgtgccacc acgccgtgcg   7080
catcagggc aagtcctacg tccagtgcca ggggatcccg cagggctcca tcctctccac   7140
gctgctctgc agcctgtgct acggcgacat ggagaacaag ctgtttgcgg ggattcggcg   7200
ggacgggctg ctcctgcgtt tggtggatga tttcttgttg gtgacacctc acctcaccca   7260
cgcgaaaacc ttcctcagga ccctggtccg aggtgtccct gagtatggct gcgtggtgaa   7320
cttgcggaag acagtggtga acttccctgt agaagacgag gccctgggtg gcacggcttt   7380
tgttcagatg ccggcccacg gcctattccc ctggtgcggc ctgctgctgg atacccggac   7440
cctggaggtg cagagcgact actccagcta tgcccggacc tccatcagag ccagtctcac   7500
cttcaaccgc ggcttcaagg ctgggaggaa catgcgtcgc aaactctttg ggtcttgcg   7560
gctgaagtgt cacagcctgt ttctggattt gcaggtgaac agcctccaga cggtgtgcac   7620
caacatctac aagatcctcc tgctgcaggc gtacaggttt cacgcatgtg tgctgcagct   7680
cccatttcat cagcaagttt ggaagaaccc cacatttttc ctgcgcgtca tctctgacac   7740
ggcctccctc tgctactcca tcctgaaagc caagaacgca gggatgtcgc tgggggccaa   7800
gggcgccgcc ggccctctgc cctccgaggc cgtgcagtgg ctgtgccacc aagcattcct   7860
gctcaagctg actcgacacc gtgtcaccta cgtgccactc ctggggtcac tcaggacagc   7920
ccagacgcag ctgagtcgga agctcccggg gacgacgctg actgccctgg aggccgcagc   7980
caacccggca ctgccctcag acttcaagac catcctggac tgagtcgaaa ctcgcggccg   8040
catgcgtcga cgcgtatcga tgcatcttaa gtagatgtac ctttaagacc aatgacttac   8100
aaggcagctg tagatcttag ccactttta aaagaaaagg ggggactgga agggctaatt   8160
cactcccaac gaagacaaga tctgcttttt gcttgtactg ggtctctctg gttagaccag   8220
atctgagcct gggagctctc tggctaacta gggaacccac tgcttaagcc tcaataaagc   8280
ttgccttgag tgcttcaagt agtgtgtgcc cgtctgttgt gtgactctgg taactagaga   8340
tccctcagac ccttttagtc agtgtggaaa atctctagca gtagtagttc atgtcatctt   8400
attattcagt atttataact tgcaaagaaa tgaatatcag agagtgagag gaacttgttt   8460
attgcagctt ataatggtta caaataaagc aatagcatca caaatttcac aaataaagca   8520
tttttttcac tgcattctag ttgtggtttg tccaaactca tcaatgtatc ttatcatgtc   8580
tggctctagc tatcccgccc ctaactccgc ccatcccgcc cctaactccg cccagttccg   8640
cccattctcc gccccatggc tgactaattt tttttattta tgcagaggcc gaggccgcct   8700
cggcctctga gctattccag aagtagtgag gaggcttttt tggaggccta gggacgtacc   8760
caattcgccc tatagtgagt cgtattacgc gcgctcactg gccgtcgttt tacaacgtcg   8820
tgactgggaa aaccctggcg ttacccaact taatcgcctt gcagcacatc ccccttcgc   8880
cagctggcgt aatagcgaag aggcccgcac cgatcgccct tcccaacagt tgcgcagcct   8940
gaatggcgaa tgggacgcgc cctgtagcgg cgcattaagc gcggcgggtg tggtggttac   9000
gcgcagcgtg accgctacac ttgccagcgc cctagcgccc gctcctttcg ctttcttccc   9060
```

```
ttcctttctc gccacgttcg ccggctttcc ccgtcaagct ctaaatcggg ggctcccttt   9120
agggttccga tttagtgctt tacggcacct cgaccccaaa aaacttgatt agggtgatgg   9180
ttcacgtagt gggccatcgc cctgatagac ggtttttcgc cctttgacgt tggagtccac   9240
gttctttaat agtggactct tgttccaaac tggaacaaca ctcaacccta tctcggtcta   9300
ttcttttgat ttataaggga ttttgccgat ttcggcctat tggttaaaaa atgagctgat   9360
ttaacaaaaa tttaacgcga attttaacaa aatattaacg cttacaattt aggtggcact   9420
tttcggggaa atgtgcgcgg aacccctatt tgtttatttt tctaaataca ttcaaatatg   9480
tatccgctca tgagacaata accctgataa atgcttcaat aatattgaaa aaggaagagt   9540
atgagtattc aacatttccg tgtcgccctt attccctttt ttgcggcatt ttgccttcct   9600
gtttttgctc acccagaaac gctggtgaaa gtaaaagatg ctgaagatca gttgggtgca   9660
cgagtgggtt acatcgaact ggatctcaac agcggtaaga tccttgagag ttttcgcccc   9720
gaagaacgtt ttccaatgat gagcactttt aaagttctgc tatgtggcgc ggtattatcc   9780
cgtattgacg ccgggcaaga gcaactcggt cgccgcatac actattctca gaatgacttg   9840
gttgagtact caccagtcac agaaaagcat cttacggatg gcatgacagt aagagaatta   9900
tgcagtgctg ccataaccat gagtgataac actgcggcca acttacttct gacaacgatc   9960
ggaggaccga aggagctaac cgcttttttg cacaacatgg gggatcatgt aactcgcctt  10020
gatcgttggg aaccggagct gaatgaagcc ataccaaacg acgagcgtga caccacgatg  10080
cctgtagcaa tggcaacaac gttgcgcaaa ctattaactg gcgaactact tactctagct  10140
tcccggcaac aattaataga ctggatggag gcggataaag ttgcaggacc acttctgcgc  10200
tcggcccttc cggctggctg gtttattgct gataaatctg gagccggtga gcgtgggtct  10260
cgcggtatca ttgcagcact ggggccagat ggtaagccct cccgtatcgt agttatctac  10320
acgacgggga gtcaggcaac tatggatgaa cgaaatagac agatcgctga gataggtgcc  10380
tcactgatta agcattggta actgtcagac caagtttact catatatact ttagattgat  10440
ttaaaacttc atttttaatt taaaaggatc taggtgaaga tcctttttga taatctcatg  10500
accaaaatcc cttaacgtga gttttcgttc cactgagcgt cagaccccgt agaaaagatc  10560
aaaggatctt cttgagatcc tttttttctg cgcgtaatct gctgcttgca aacaaaaaaa  10620
ccaccgctac cagcggtggt ttgtttgccg gatcaagagc taccaactct ttttccgaag  10680
gtaactggct tcagcagagc gcagatacca aatactgttc ttctagtgta gccgtagtta  10740
ggccaccact tcaagaactc tgtagcaccg cctacatacc tcgctctgct aatcctgtta  10800
ccagtggctg ctgccagtgg cgataagtcg tgtcttaccg ggttggactc aagacgatag  10860
ttaccggata aggcgcagcg gtcgggctga acggggggtt cgtgcacaca gcccagcttg  10920
gagcgaacga cctacaccga actgagatac ctacagcgtg agctatgaga aagcgccacg  10980
cttcccgaag ggagaaaggc ggacaggtat ccggtaagcg gcagggtcgg aacaggagag  11040
cgcacgaggg agcttccagg gggaaacgcc tggtatcttt atagtcctgt cgggtttcgc  11100
cacctctgac ttgagcgtcg atttttgtga tgctcgtcag gggggcggag cctatggaaa  11160
aacgccagca acgcggcctt tttacggttc ctggcctttt gctggccttt tgctcacatg  11220
ttctttcctg cgttatcccc tgattctgtg gataaccgta ttaccgcctt tgagtgagct  11280
gataccgctc gccgcagccg aacgaccgag cgcagcgagt cagtgagcga ggaagcggaa  11340
gagcgcccaa tacgcaaacc gcctctcccc gcgcgttggc cgattcatta atgcagctgg  11400
```

-continued

```
cacgacaggt ttcccgactg gaaagcgggc agtgagcgca acgcaattaa tgtgagttag  11460

ctcactcatt aggcacccca ggctttacac tttatgcttc cggctcgtat gttgtgtgga  11520

attgtgagcg gataacaatt tcacacagga aacagctatg accatgatta cgccaagcgc  11580

gcaattaacc ctcactaaag ggaacaaaag ctggagctgc aagctt                 11626
```

ENHANCING HEALTH IN MAMMALS USING TELOMERASE REVERSE TRANSCRIPTASE GENE THERAPY

The improvement of health during aging is of interest in aging research. Markers of aging include conditions such as epithelial barrier fitness, osteoporosis, glucose intolerance with insulin insensitivity, loss of memory, and neuromuscular degeneration associated with loss of neuromuscular coordination. For example, bone loss is a well-characterized sign of the aging progress both in mammals including humans which results from bone resorption due to osteoblast insufficiency. Therefore, methods that increase life span and ameliorate various age-related parameters are of interest.

Telomeres are regions of repetitive DNA found at the ends of the chromosomes of most eukaryotes. For example, human telomeres include many kilobases of (TTAGGG)n and are associated with various proteins. Small portions of these terminal sequences of telomeric DNA are lost from the tips of the chromosomes during the S phase of the cell cycle because of incomplete DNA replication. Many human cells progressively lose terminal sequences with cell division, a loss that correlates with the apparent absence of telomerase in these cells. The resulting telomere shortening limits cellular lifespan.

Telomerase is a ribonucleoprotein that synthesizes telomeric DNA. Telomerase is made up of two components: (1) an essential structural RNA component (TR or TER) (in humans the component is referred to as hTR or hTER), and (2) a catalytic protein (telomerase reverse transcriptase or TERT) (in humans the component is referred to as hTERT). Telomerase works by adding multiple DNA sequence repeats to the 2+ end of DNA in the telomere region, where hTER serves as the template for nucleotide incorporation, and TERT as the catalyst. Both the catalytic protein component and the RNA template component of telomerase are activity-limiting components.

SUMMARY

Methods of treating an age-related disorder or condition in a subject are provided. Aspects of the methods include administering to the subject a nucleic acid vector including a coding sequence for telomerase reverse transcriptase (TERT) and/or telomerase RNA (TR). Gene therapy methods are also provided. Aspects of the invention further include compositions, e.g., nucleic acid vectors and kits, etc., that find use in methods of the invention.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
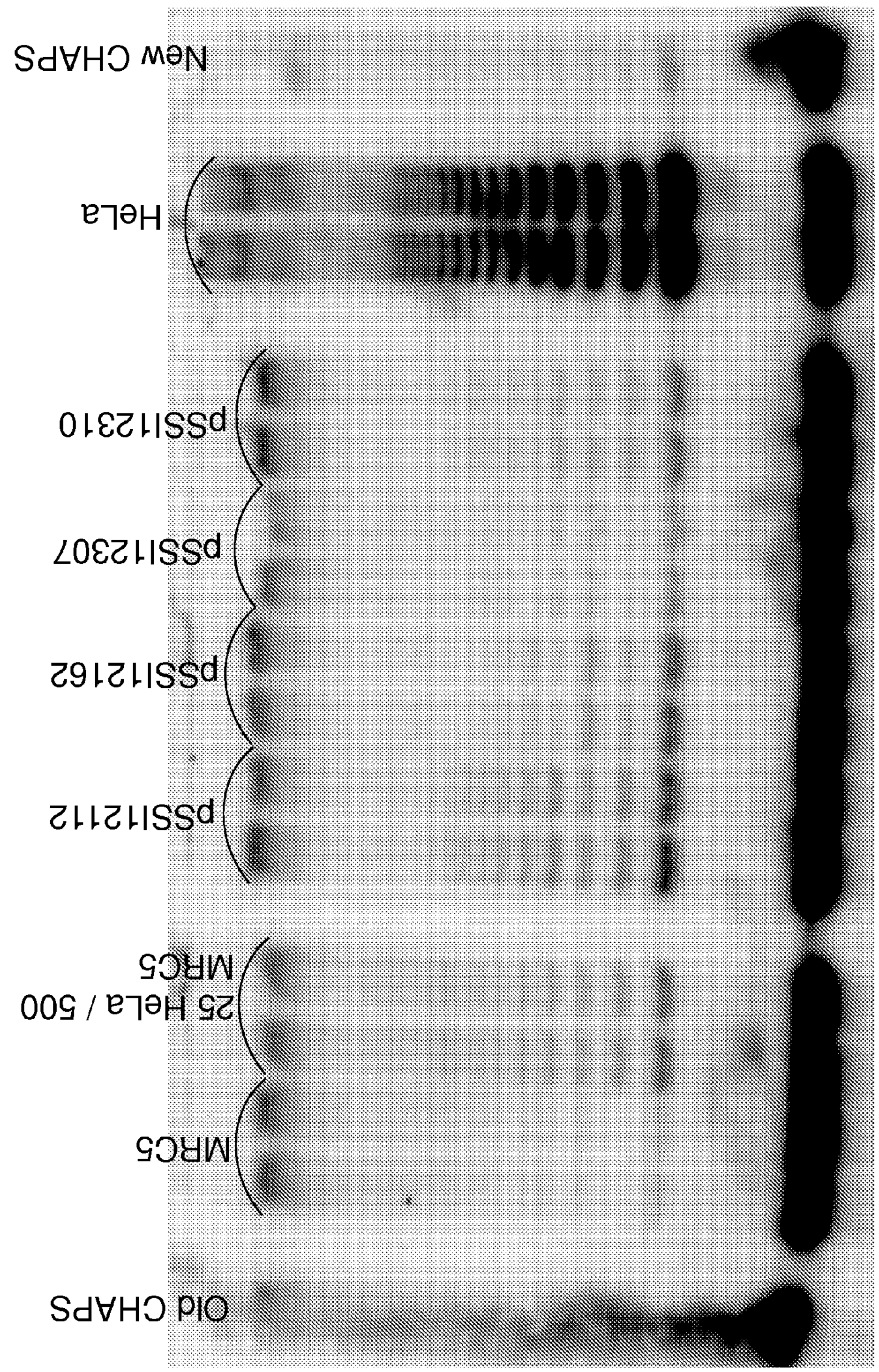
FIG. 1 depicts the results of a TRAP Assay using the vectors pSSI12112, pSSI12162, pSSI12307 and pSSI12310 where sample cells are collected at 7 days post BSD selection, 17 days post infection.

As summarized above, aspects of the invention include methods of treating an age-related disorder in a subject. Aspects of the methods include administering to the subject a nucleic acid vector including a coding sequence for telomerase reverse transcriptase (TERT). In some cases, the vector may include a coding sequence for telomerase RNA (TR). Gene therapy methods that utilize the subject vectors are also provided. Embodiments of the invention include compositions, e.g., nucleic acid vectors and kits, etc., that find use in the subject methods.

The subject methods may lead to increase the expression of telomerase reverse transcriptase and/or telomerase RNA when administered to adult mammals. Administration of the vectors to the subject may extend the lifespan of the subject (e.g., average or maximum lifespan), and may ameliorate one or more markers of ageing, including but not limited to epithelial barrier fitness, osteoporosis, glucose intolerance with insulin insensitivity, loss of memory, and neuromuscular degeneration associated with loss of neuromuscular coordination. The effect may be achieved without increasing the incidence of cancer (malignant neoplastic disease), as assessed by the number of spontaneous neoplasms evident among the population treated.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Vectors

As summarized above, one aspect of the invention is a nucleic acid vector. Application of the subject vector to a subject, e.g. using any convenient method such as a gene therapy method, may result in expression of one or more coding sequences of interest in cells of the subject, to produce a biologically active product that may modulate a biological activity of the cell. In some cases, the vector is a nucleic acid vector comprising a coding sequence for telomerase reverse transcriptase (TERT). In some cases, the nucleic acid vector comprises a coding sequence for one or more telomerase components, such as TERT and telomerase RNA (TR). In some embodiments, the vector does not include a cancer suppressing sequence.

In some instances, the vector comprises a coding sequence for telomerase reverse transcriptase (TERT) suitable for use in gene therapy. Gene therapy vectors of interest include any kind of particle that comprises a polynucleotide fragment encoding the telomerase reverse transcriptase (TERT) protein, operably linked to a regulatory element such as a promoter, which allows the expression of a functional TERT protein demonstrating telomerase reverse transcriptase activity in the targeted cells. In some cases, TERT is encoded by the nucleic acid sequence as set forth in SEQ ID NO:1 of WO2012001170 or SEQ ID NO:3 of WO2012001170, or is an active fragment or functional equivalent of TERT. In some instances, the vector include a regulatory sequence which is a constitutive promoter such as the cytomegalovirus (CMV) promoter.

The TERT and/or TR sequence used in the gene therapy vector may be derived from the same species as the subject. Any convenient TERT and/or TR sequences, or fragments or functional equivalents thereof, may be utilized in the subject vectors, including sequences from any convenient animal, such as a primate, ungulate, cat, dog, or other domestic pet or domesticated mammal, rabbit, pig, horse, sheep, cow, or a human. For example, gene therapy in humans may be carried out using the human TERT sequence. In some embodiments, the TERT and/or TR sequence is not a murine sequence.

As used herein, "functional equivalent" refers to a nucleic acid molecule that encodes a polypeptide that has TERT activity or a polypeptide that has TERT activity. The functional equivalent may displays 50%, 60%, 70%, 80%, 90%, 95%, 98%, 99%, 100% or more activity compared to a parent TERT sequence. Functional equivalents may be artificial or naturally-occurring. For example, naturally-occurring variants of the TERT sequence in a population fall within the scope of functional equivalent. TERT sequences derived from other species also fall within the scope of the term "functional equivalent", e.g., a murine TERT sequence. In a particular embodiment, the functional equivalent is a nucleic acid with a nucleotide sequence having at least 75%, 80%, 85%, 90%, 95%, 96%, 97%, 98%, 99%, 99.5%, 99.9% identity to the parent sequence. In a further embodiment, the functional equivalent is a polypeptide with an amino acid sequence having at least 75%, 80%, 85%, 90%, 95%, 96%, 97%, 98%, 99%, 99.5%, 99.9%identity to a parent sequence. In the case of functional equivalents, sequence identity should be calculated along the entire length of the nucleic acid. Functional equivalents may contain one or more, e.g. 2, 3, 4, 5, 10, 15, 20, 30 or more, nucleotide insertions, deletions and/or substitutions when compared to a parent sequence.

The term "functional equivalent" also encompasses nucleic acid sequences that encode a TERT polypeptide with at least 75%, 80%, 85%, 90%, 95%, 96%, 97%, 98%, 99%, 99.5%, 99.9% sequence identity to the parent amino acid sequence, but that show little homology to the parent nucleic acid sequence because of the degeneracy of the genetic code.

As used herein, the term "active fragment" refers to a nucleic acid molecule that encodes a polypeptide that has TERT activity or polypeptide that has TERT activity, but which is a fragment of the nucleic acid as set forth in the parent polynucleotide sequence or the amino acid sequence as set forth in parent polypeptide sequence. An active fragment may be of any size provided that TERT activity is retained. A fragment will have at least 75%, 80%, 85%, 90%, 95%, 96%, 97%, 98%, 99%, 99.5%, 100% identity to the parent sequence along the length of the alignment between the shorter fragment and longer parent sequence.

Fusion proteins including these fragments can be comprised in the nucleic acid vectors needed to carry out the invention. For example, an additional 5, 10, 20, 30, 40, 50 or even 100 amino acid residues from the polypeptide sequence, or from a homologous sequence, may be included at either or both the C terminal and/or N terminus without prejudicing the ability of the polypeptide fragment to fold correctly and exhibit biological activity. Sequence identity may be calculated by any one of the various methods in the art, including for example BLAST (Altschul S F, Gish W, Miller W, Myers E W, Lipman D J (1990). "Basic local alignment search tool". J Mol Biol 215 (3): 403-410) and PASTA (Lipman, D J; Pearson, W R (1985). "Rapid and sensitive protein similarity searches". Science 227 (4693): 1435-41; http://fasta.bioch.virginia.edu/fasta www2/fasta list2.shtml) and variations on these alignment programs.

The vector may further include one or more regulatory sequences. Any convenient regulatory sequences or promoter sequences may be utilized in the subject vectors, e.g., as described herein. In some embodiments, the regulatory sequence that is operatively linked to the coding sequence (e.g., the TERT and/or TR sequence) is the cytomegalovirus promoter (CMV), although any other convenient regulatory sequences may be utilized.

Viral Vectors

Any convenient viruses may be utilized in delivering the vector of interest to the subject. Viruses of interest include, but are not limited to a retrovirus, an adenovirus, an adeno-associated virus (AAV), a herpes simplex virus and a lentivirus. Viral gene therapy vectors are well known in the art, see e.g., Heilbronn & Weger (2010) Handb Exp Pharmacal. 197:143-70. Vectors of interest include integrative and non-integrative vectors such as those based on retroviruses, adenoviruses (AdV), adeno-associated viruses (AAV), lentiviruses, pox viruses, alphaviruses, and herpes viruses.

In some cases, non-integrative viral vectors, such as AAV, may be utilized. In one aspect, non-integrative vectors do not cause any permanent genetic modification. The vectors may be targeted to adult tissues to avoid having the subjects under the effect of constitutive telomerase expression from early stages of development. In some instances, non-integrative vectors effectively incorporate a safety mechanism to avoid over-proliferation of TERT expressing cells. The cells may lose the vector (and, as a consequence, the telomerase expression) if they start proliferating quickly.

Non-integrative vectors of interest include those based on adenoviruses (AdV) such as gutless adenoviruses, adeno-associated viruses (AAV), integrase deficient lentiviruses, pox viruses, alphaviruses, and herpes viruses. In certain embodiments, the non-integrative vector used in the invention is an adeno-associated virus-based non-integrative vector, similar to natural adeno-associated virus particles. Examples of adena-associated virus-based non integrative vectors include vectors based on any AAV serotype, i.e. AAV1, AAV2, AAV3, AAV4, AAV5, AAV6, AAV7, AAV8, AAV9, AAVIO, AAVII and pseudotyped AAV. Vectors of interest include those capable of transducing a broad range of tissues at high efficiency, with poor immunogenicity and an excellent safety profile. In some cases, the vectors transduce post-mitotic cells and can sustain long-term gene expression (up to several years) both in small and large animal models of age-related disorders.

Methods

As summarized above, aspects of the invention include methods of administering a nucleic acid vector to a subject. As such, aspects of the invention include contacting the subject with a viral vector, e.g., as described above, under conditions by which expression of one or more telomerase components (such as TERT and/or TR) in the subject results in a beneficial effect on one or more aspects of the subject's health, including increased longevity, delayed osteoporosis, improved epithelial barrier fitness, improved glucose tolerance, improved memory function, and improved neuromuscular coordination. In some cases, the subject did not develop increased incidence of cancer, illustrating the safety of this type of strategy.

In gene therapy methods, genes are directly inserted into cells affected by an age-related condition so that the function of the cells is normalized by expressing the inserted genes. The gene therapy methods may be used to prevent various diseases or age-related conditions or to reinforce treatment by inserting a specific gene into a body cell and granting a new function to the body cell. One aspect in the treatment of such conditions using gene therapy is that the inserted gene be successfully delivered to the nucleus of the target cell and that the gene be expressed strongly. The gene enters the target cell through endocytosis and is transported into the nucleus to be expressed. The gene can be inserted using a carrier such as a liposome since most DNAs are destroyed when entering the cell. However, most of the liposomes are also destroyed when entering the nucleus, thereby decreasing the transporting efficiency. A virus capable of infecting a human can be treated using gene therapy because the virus effectively inserts exogeneous genes into the human body. Specifically, the gene can effectively be transported and expressed by inserting the gene for the gene therapy into the DNA of the virus using gene recombination and infecting the subject (e.g., a human) with the recombinant virus, which can be mass produced in vitro. In some cases, an adenovirus can be effectively used for the gene therapy by using a mechanism of transporting the gene into the nucleus of the target cell with a high efficiency. In addition, retroviruses are being used in many internationally permissible clinical trials (Wiley—The Journal of Gene Medicine Website: http://www.wiley.co.uk/genetherapy). Retroviruses are effective for gene therapy when inserted into cell chromosomal DNA to allow long term expression of the desired protein.

In certain instances, the expression of the TERT and/or TR following gene therapy according to the invention persists for a time of one or more weeks, such as one or more months, e.g., several months to several years.

When treating specific age related disorders, it is advantageous to target the treatment to the effected tissues. The serotype of the capsid protein of the gene therapy vector may thus be selected based on the desired site of gene therapy, e.g., skeletal muscle tissue for treating neuromuscular coordination.

Any convenient methods may be employed. Methods and vectors of interest that may be adapted for use in the subject invention include, but are not limited to the methods and vectors of WO 2012/001170 and Vidale et al. "The catalytic and the RNA subunits of human telomerase are required to immortalize equid primary fibroblasts." Chromosoma. 2012 Jul. 14. Epub, the disclosures of which are herein incorporated by reference.

In some embodiments, the method of treatment is a gene therapy method and/or the nucleic acid vector used is a gene therapy vector. Gene therapy methods and vectors are well known in the art and generally include delivering a nucleic acid encoding a therapeutically active protein to a subject. The nucleic acid may be delivered in a number of ways including delivering naked DNA such as plasmid or mini-circles, the use of liposomes or cationic polymers or other engineered nano-particles containing the nucleic acid, or viral vectors that encapsidate the nucleic acid.

In a further embodiment, the gene therapy is achieved using stable transformation of organisms with an inducible expression system. In certain embodiments, this aspect of the invention does not extend to human subjects. Expression of TERT or TR can be induced at a later date following transformation, for example, once the subject is an adult or an aged adult, or begins to show signs of age-related disorders. Suitable inducible expression systems are known in the art and include the CRE-LOX recombinase based system and the tetracycline-regulated system.

In some embodiments, the present invention is limited to the expression of TERT an/or TR in adult or aged subjects. In certain embodiments, the methods and vectors are utilized with post-mitotic cells within the subjects, and avoid any increased incidence of cancer.

Any convenient subjects may be treated according to the subject methods. The subject may be an adult animal, such as an adult mammal. The mammal may be a primate, ungulate, cat, dog, domestic pet or domesticated mammal. In some cases, the mammal may be a rabbit, pig, horse, sheep, cow, cat or dog, or a human. In certain embodiments the subject is not a murine mammal. An adult subject treated according to the invention may be aged. The term "aged" is applied to an individual who is older than the period of life during which the individuals of its species are generally healthy and free of chronic illness. According to the present application, an "adult" should be a fully developed individual who has attained reproductive ability, is fertile, or who evidences secondary sex characteristics. As used herein, the term adult when applied to humans, for example, describes early adulthood commencing at around 20 years of age and extending to 39; middle adulthood (40 to 59) and late adulthood (60+). As a comparison, a one year old mouse can be considered to be approximately equivalent in age to a 45 year old human. A 2 year old mouse can be considered to be approximately equivalent to an 80 year old human.

The particular protocol that is employed may vary. Administration of the vectors may be achieved using any convenient protocol. Vectors as described above (e.g., retroviral vectors and lentiviral vectors) may be administered in vivo to subjects by any convenient route. The term "administration" refers to the route of introduction of a formulated vector into the body. For example, administration may be intravenous, intramuscular, topical, oral, or by gene gun or hypospray instrumentation. Thus, administration can be direct to a target tissue or through systemic delivery. Administration directly to the target tissue can involve needle injection, hypospray, electroporation, or the gene gun. See, e.g., WO 93/18759, hereby incorporated by reference herein. Alternatively, vectors of the invention can be administered ex vivo or in vitro to cells or tissues using any convenient transfection techniques.

The vectors of the invention can also be transduced into host cells, including but not limited to, embryonic stem cells, somatic stem cells, or progenitor cells. Examples of progenitor host cells which can be transduced by the vectors of the invention include precursors of erythrocytes and hematopoietic stem cells. In another embodiment, the host cell is an erythrocyte. Transduced host cells can be used as a method of achieving erythroid-specific expression of the gene of interest in the treatment of hemoglobinopathies.

In some embodiments, the method does not include concomitant use of a cancer suppressor.

The step of facilitating the production of infectious viral particles in the cells may be carried out using conventional techniques, such as standard cell culture growth techniques. If desired by the skilled artisan, lentiviral stock solutions may be prepared using the vectors and methods of the present invention. Methods of preparing viral stock solutions are known in the art and are illustrated by, e.g., Y. Soneoka et al. (1995) Nucl. Acids Res. 23:628-633, and N. R. Landau et al. (1992) J. Virol. 66:5110-5113. In a method of producing a stock solution in the present invention, lentiviral-permissive cells (referred to herein as producer cells) are transfected with the vector system of the present invention. The cells are then grown under suitable cell culture conditions, and the lentiviral particles collected from either the cells themselves or from the cell media as described above. Suitable producer cell lines include, but are not limited to, the human embryonic kidney cell line 293, the equine dermis cell line NBL-6, and the canine fetal thymus cell line Cf2TH.

The step of collecting the infectious virus particles also can be carried out using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

Other methods relating to the use of viral vectors in gene therapy can be found in, e.g., Kay, M. A. (1997) Chest 111(6 Supp.): 138S-142S; Ferry, N. and Heard, J. M. (1998) Hum. Gene Ther. 9:1975-81; Shiratory, Y. et al. (1999) Liver 19:265-74; Oka, K. et al. (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J. Hepatol. 23:746-58;

Brody, S. L. and Crystal, R. G. (1994) Ann. N.Y. Acad. Sci. 716:90-101; Strayer, D. S. (1999) Expert Opin. Investig. Drugs 8:2159-2172; Smith-Arica, J. R. and Bartlett, J. S. (2001) Curr. Cardiol. Rep. 3:43-49; and Lee, H. C. et al. (2000) Nature 408:483-8.

As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier is suitable for administration directly into an affected joint. The carrier can be suitable for intravenous, intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Another aspect of the invention pertains to pharmaceutical compositions of the vectors of the invention. In one embodiment, the composition includes a vector in a therapeutically effective amount sufficient to treat or prevent (e.g. ameliorate one or more age-related conditions), and a pharmaceutically acceptable carrier. A "therapeutically effective amount" refers to an amount effective, at dosages and for periods of time necessary, to achieve the desired therapeutic result, such as treatment or amelioration of an age-related condition. A therapeutically effective amount of vector may vary according to factors such as the disease state, age, sex, and weight of the individual, and the ability of the viral vector to elicit a desired response in the individual. Dosage regimens may be adjusted to provide the optimum therapeutic response. A therapeutically effective amount is also one in which any toxic or detrimental effects of the viral vector are outweighed by the therapeutically beneficial effects. The potential toxicity of the viral vectors of the invention can be assayed using cell-based assays or art recognized animal models and a therapeutically effective modulator can be selected which does not exhibit significant toxicity. In a preferred embodiment, a therapeutically effective amount of a viral vector is sufficient to treat or ameliorate one or more age-related conditions in as subject.

Sterile injectable solutions can be prepared by incorporating viral vector in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

It is to be noted that dosage values may vary with the severity of the condition to be ameliorated. It is to be further understood that for any particular subject, specific dosage regimens can be adjusted over time according to the individual need and the professional judgment of the person administering or supervising the administration of the compositions, and that dosage ranges set forth herein are exemplary only and are not intended to limit the scope or practice of the claimed composition.

The amount of viral vector in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In Vitro Methods

Also included are in vitro methods, where the subject vectors, e.g., as described above are contacted with a sample. The particular protocol that is employed may vary, e.g., depending on the sample. For in vitro protocols, contact of the vector with the sample may be achieved using any convenient protocol. In some instances, the sample includes cells that are maintained in a suitable culture medium, and the vector is introduced into the culture medium. Depending upon the nature of the vector (e.g., a viral vector), the response desired, the manner of contacting or administration, the number of cells present, various protocols may be employed. The term “sample” as used herein relates to a material or mixture of materials, typically, although not necessarily, in fluid form, containing one or more components of interest.

Utility

The vectors and methods of the invention, e.g., as described above, find use in a variety of applications. Applications of interest include, but are not limited to: research applications and therapeutic applications. Methods of the invention find use in a variety of different applications including any convenient application where the subject is experiencing one or more age-related conditions. In some cases, age-related disorders or conditions that may be modulated or ameliorated using the subject vectors and methods include, but are not limited to, osteoporosis, arthrosis, glucose intolerance, insulin resistant, reduced heart, circulatory and/or lung function, cardiovascular disease, loss of memory, loss of neuromuscular coordination and decrease of longevity, or combinations thereof.

The subject vectors and methods find use in a variety of research applications. The subject vectors and methods may be used to analyze the role of telomerase various biological processes including age-related disorders and conditions.

The subject vectors and methods find use in a variety of therapeutic applications. Therapeutic applications of interest include those applications in which the subject is suffering from one or more age-related disorders or conditions. As such, the subject vectors find use in the treatment of a variety of different age-related conditions in various subjects, and may lead to an extended lifespan. For example, the subject vectors and methods may find use in regulated gene therapy.

Extended lifespan may be an increase in the maximum lifespan possible for any particular species of subject. Extended lifespan may be an increase in the average lifespan of an individual of that species who reaches adulthood. Thus, extended lifespan may be a 5%, 10%, 15%, 20% or more increase in maximum lifespan and/or a 5%, 10%, 15%, 20% or more increase in average lifespan.

The application of the invention extends the period of time for which an individual is generally healthy and free of chronic illness and/or the invention ameliorates disorders that appear often in aged and ageing adult population, including reduced epithelial barrier fitness, osteoporosis, glucose intolerance and neuromuscular degeneration associated with loss of neuromuscular coordination. These are well established indicators of ageing progression.

Accordingly, the invention has beneficial effects in at least one of the following group: reducing the incidence of cancer, on delaying and/or ameliorating osteoporosis, improving epithelial barrier fitness, improving glucose tolerance, improving memory function, and improving neuromuscular coordination. The amelioration of age-related disorders provided by the invention can be as a result of reduction of symptoms in an affected subject or a reduction of incidence of the disease or disorder in a population as compared to an untreated population. The application of gene therapy according to the invention has the effect of treating and/or preventing various age-related conditions and diseases, as assessed by particular markers and disorders of ageing. In a further aspect, therefore, the invention refers to a gene therapy method or the used of a nucleic acid vector as described above, for use in the treatment or prevention in a subject of at least a disorder or marker of ageing that is selected from the group of reduced epithelial barrier fitness, osteoporosis, arthrosis, glucose intolerance, insulin resistanance, loss of memory, loss of neuromuscular coordination, increase in cardiovascular disease, decrease in heart, circulatory or lung function and decrease in longevity, or combinations thereof. The gene therapy ameliorates at least one marker of ageing, selected for example, from the group of reduced epithelial barrier fitness, osteoporosis, arthrosis, glucose intolerance, insulin resistance, cardiovascular disease, reduced heart and circulatory function, reduced lung function, loss of memory, loss of neuromuscular coordination or decrease of longevity or combinations thereof.

Kits

Aspects of the invention further include kits, where the kits include one or more components employed in methods of the invention, e.g., vectors, as described herein. In some embodiments, the subject kit includes a vector (as described herein), and one or more components selected from a promoter, a virus, a cell, and a buffer. Any of the components described herein may be provided in the kits, e.g., cells, constructs (e.g., vectors) encoding for TERT and/or TR, components suitable for use in expression systems (e.g., cells, cloning vectors, multiple cloning sites (MSC), bi-directional promoters, an internal ribosome entry site (IRES), etc.), etc. A variety of components suitable for use in making and using constructs, cloning vectors and expression systems may find use in the subject kits. Kits may also include tubes, buffers, etc., and instructions for use. The various reagent components of the kits may be present in separate containers, or some or all of them may be pre-combined into a reagent mixture in a single container, as desired.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), Hard Drive etc., on which the information has been recorded. Yet another form of these instructions that may be present is a website address which may be used via the internet to access the information at a removed site.

Aspects of the invention include providing a virus particle that includes a nucleic acid vector, e.g., as described above. Any convenient virus particles may be utilized, and include viral vector particles described above.

Aspects of the invention include providing a cell that includes a nucleic acid vector. The cell that is provided with the vector of interest may vary depending on the specific application being performed. Target cells of interest include eukaryotic cells, e.g., animal cells, where specific types of animal cells include, but are not limited to: insect, worm or mammalian cells. Various mammalian cells may be used, including, by way of example, equine, bovine, ovine, canine, feline, murine, non- human primate and human cells. Among the various species, various types of cells may be used, such as hematopoietic, neural, glial, mesenchymal, cutaneous, mucosal, stromal, muscle (including smooth muscle cells), spleen, reticulo-endothelial, epithelial, endothelial, hepatic, kidney, gastrointestinal, pulmonary, fibroblast, and other cell types. Hematopoietic cells of interest include any of the nucleated cells which may be involved with the erythroid, lymphoid or myelomonocytic lineages, as well as myoblasts and fibroblasts. Also of interest are stem and progenitor cells, such as hematopoietic, neural, stromal, muscle, hepatic, pulmonary, gastrointestinal and mesenchymal stem cells, such as ES cells, epi-ES cells and induced pluripotent stem cells (iPS cells).

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Construction of Vectors pSSI14342: Adeno vector containing hTR and hTERT was constructed. LITR-U1-hTR-CMV-hTERT-SV40pA-RITR Region base locations:

Adeno RITR: 2928-3030
U1 promoter: 6459-6668
hTR: 6850-7300
U1-3' box: 7458-7472
CMV promoter: 7485-8073
Kozak: 8082-8098
TERT: 8087-11482
SV40pA: 11558-11679
Adeno LITR: 5973-6075 pSSI10902: Lentiviral vector pSSI10902 was constructed and contains hTERT, Puro gene (for selection of infected cells) and AmCyan gene (a fluorescent protein for color). In pSSI10902, hTERT is expressed using the CMV promoter, Puro gene is expressed using the SV40 promoter, and AmCyan gene is expressed using the CMV promoter. Below is shown the schematic for the pSSI10902 expression cassette. The sequence of this entire vector is also provided (SEQ ID NO:2).

pSSI10902: 5'-LTR-CMV-hTERT-SV40-Puro-CMV-AmCyan-LTR-2'

Region base locations:
5' LTR: 230-410
CMV promoter: 1883-2374
Kozak: 2627-2643
hTERT: 2632-6027
SV40 promoter: 6053-6286
CMV promoter: 7242-7830
AmCyan: 7891-8577
3' LTR: 9315-9495 pSSI12112: The lentiviral vector pSSI12112 was constructed as a dual vector containing both hTR and hTERT in the same vector. hTR is expressed using the U1 promoter and hTERT is expressed using the CMV promoter. Note: this plasmid also contains the BSD gene being expressed by the PGK promoter which allows selection for cells infected with the lentivirus created using this plasmid. Below is shown a schematic of the expression cassette for pSSI12112. The sequence of this entire vector is also attached (SEQ ID NO:3).

pSSI12112: 5'-LTR-U1-hTR-PGK-BSD-CMV-hTERT-LTR-3'

Region base locations:
5' LTR: 230-410
U1 promoter: 1876-2085
hTR: 2267-2717

U1-3' box: 2875-2889
PGK promoter: 2916-3421
BSD: 3499-3894
CMV promoter: 4023-4611
Kozak: 4620-4636
hTERT: 4625-8020
3' LTR: 8200-8380

Further vectors were constructed and tested as described herein.

pSSI12112=LTR-U1-hTR-PGK-BSD-CMV-TSS-hTERT-LTR pSSI12162=LTR-U1-hTR-PGK-BSD-CMV-TSS-nonhTERT-LTR pSSI12307=LTR-PGK-BSD-CMV-TSS-hTERT-LTR pSSI12310=LTR-PGK-BSD-CMV-TSS-nonhTERT-LTR The viral vectors are tested in vitro or in vivo using any convenient methods. Methods of interest that are adapted for use in testing the viral vectors described herein include those methods described by WO 2012/001170 and Vidale et al. "The catalytic and the RNA subunits of human telomerase are required to immortalize equid primary fibroblasts." Chromosoma. 2012 Jul. 14. Epub.

Project 2273 pSSI12112 (hTR+hTERT) was tested in MRC5 cells. At 7 days post BSD selection, the TRAP activity from pSSI12112 is slightly stronger than the other 3 test samples (pSSI12162 (hTR +non-functional hTERT), pSSI12307 (hTERT), and pSSI12310 (non-functional hTERT)). At 14 days post selection, the pSSI12112 TRAP activity is less than the other 3 samples and eventually diminishes to no TRAP signal at 21 days post BSD selection. FIG. 1 depicts the results of a TRAP Assay using the vectors pSSI12112, pSSI12162, pSS112307 and pSSI12310 where sample cells are collected at 7 days post BSD selection, 17 days post infection.

Figure 2:
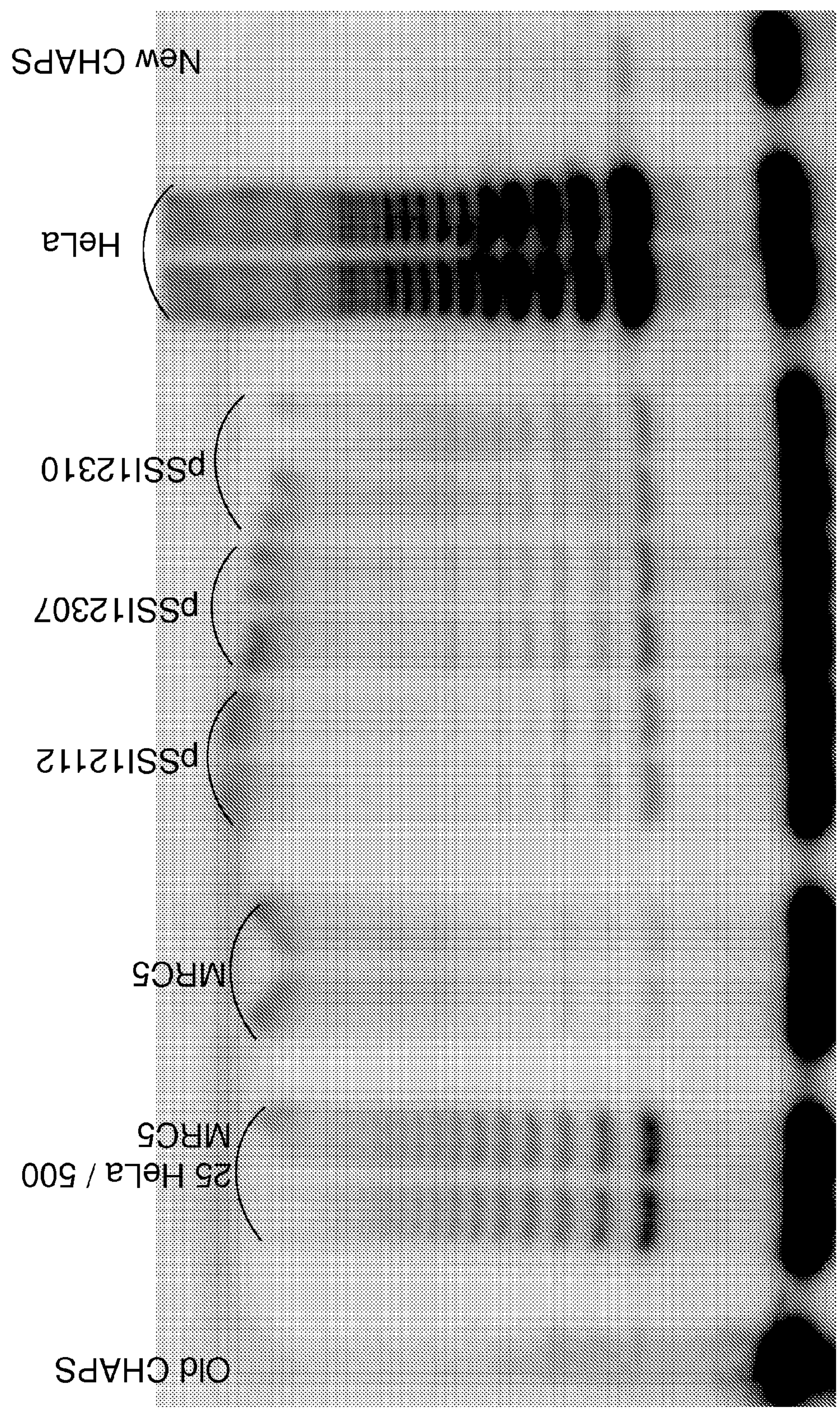
FIG. 2 depicts the results of a TRAP Assay using the vectors pSSI12112, pSSI12307 and pSSI12310 where sample cells are collected at 14 days post BSD selection, 24 days post infection.

FIG. 2 depicts the results of a TRAP Assay using the vectors pSSI12112, pSSI12307 and pSSI12310 where sample cells are collected at 14 days post BSD selection, 24 days post infection.

Figure 3:
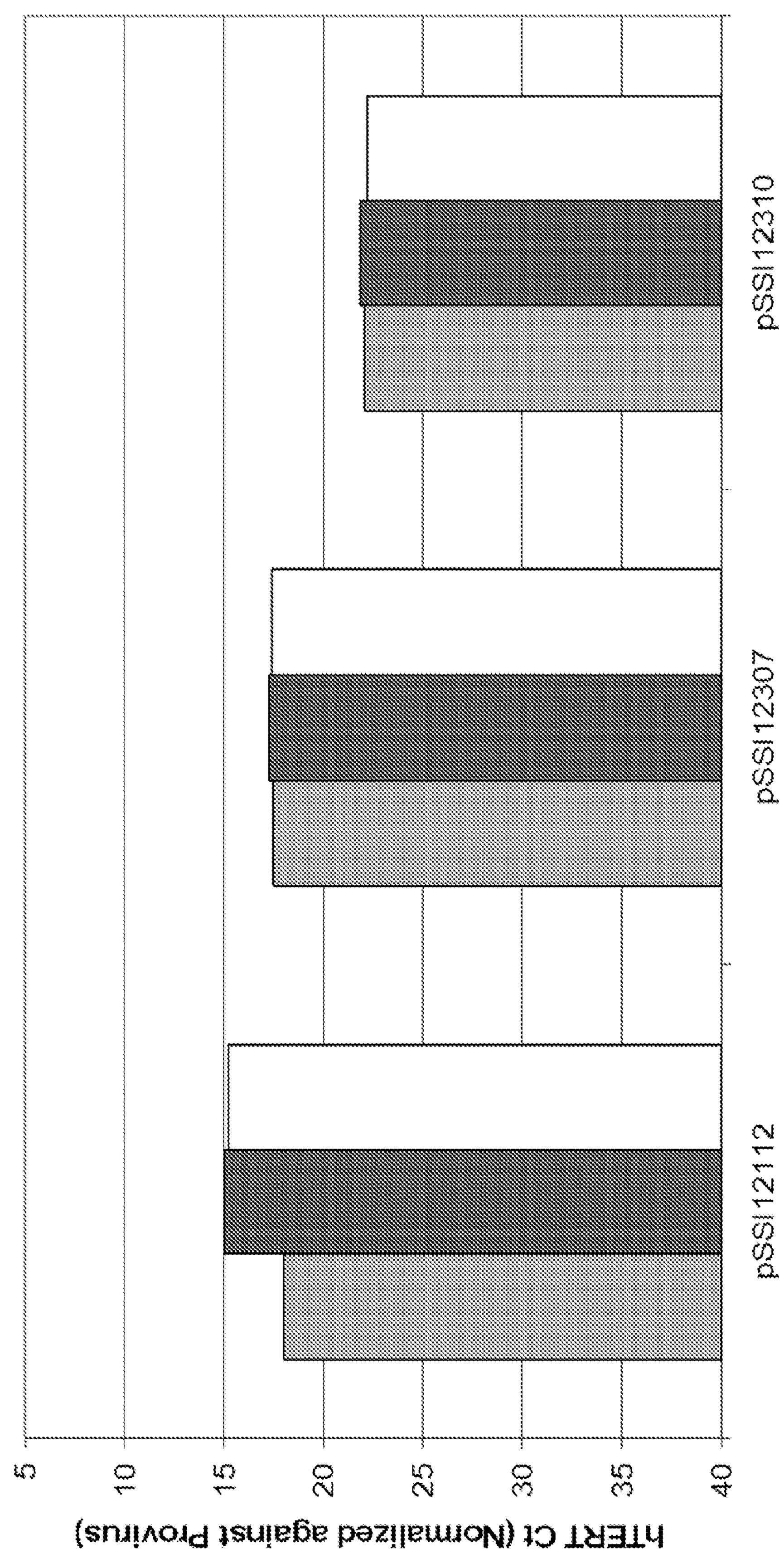
FIG. 3 illustrates RT-PCR results for hTERT Ct (normalized against provirus) using the vectors pSSI12112, pSSI12307 and pSSI12310 where sample cells are collected at 14 days post BSD selection, 24 days post infection.

FIG. 3 illustrates RT-PCR results for hTERT Ct (normalized against provirus) using the vectors pSSI12112, pSSI12307 and pSSI12310 where sample cells are collected at 14 days post BSD selection, 24 days post infection.

Figure 4:
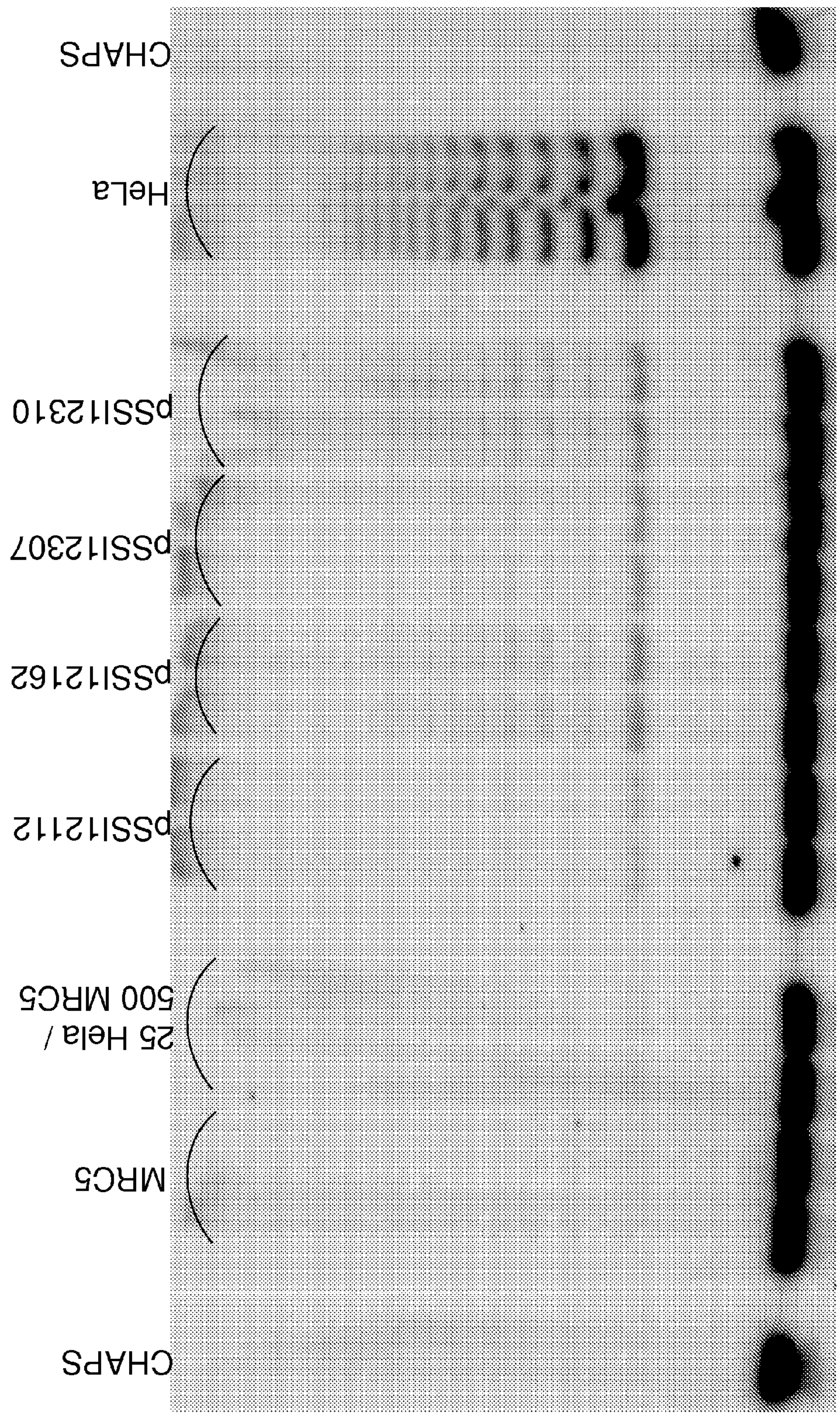
FIG. 4 depicts the results of a TRAP Assay using the vectors pSSI12112, pSSI12162, pSSI12307 and pSSI12310 where sample cells are collected at 21 days post BSD selection, 31 days post infection.

FIG. 4 depicts the results of a TRAP Assay using the vectors pSSI12112, pSSI12162, pSSI12307 and pSSI12310 where sample cells are collected at 21 days post BSD selection, 31 days post infection.

Figure 5:
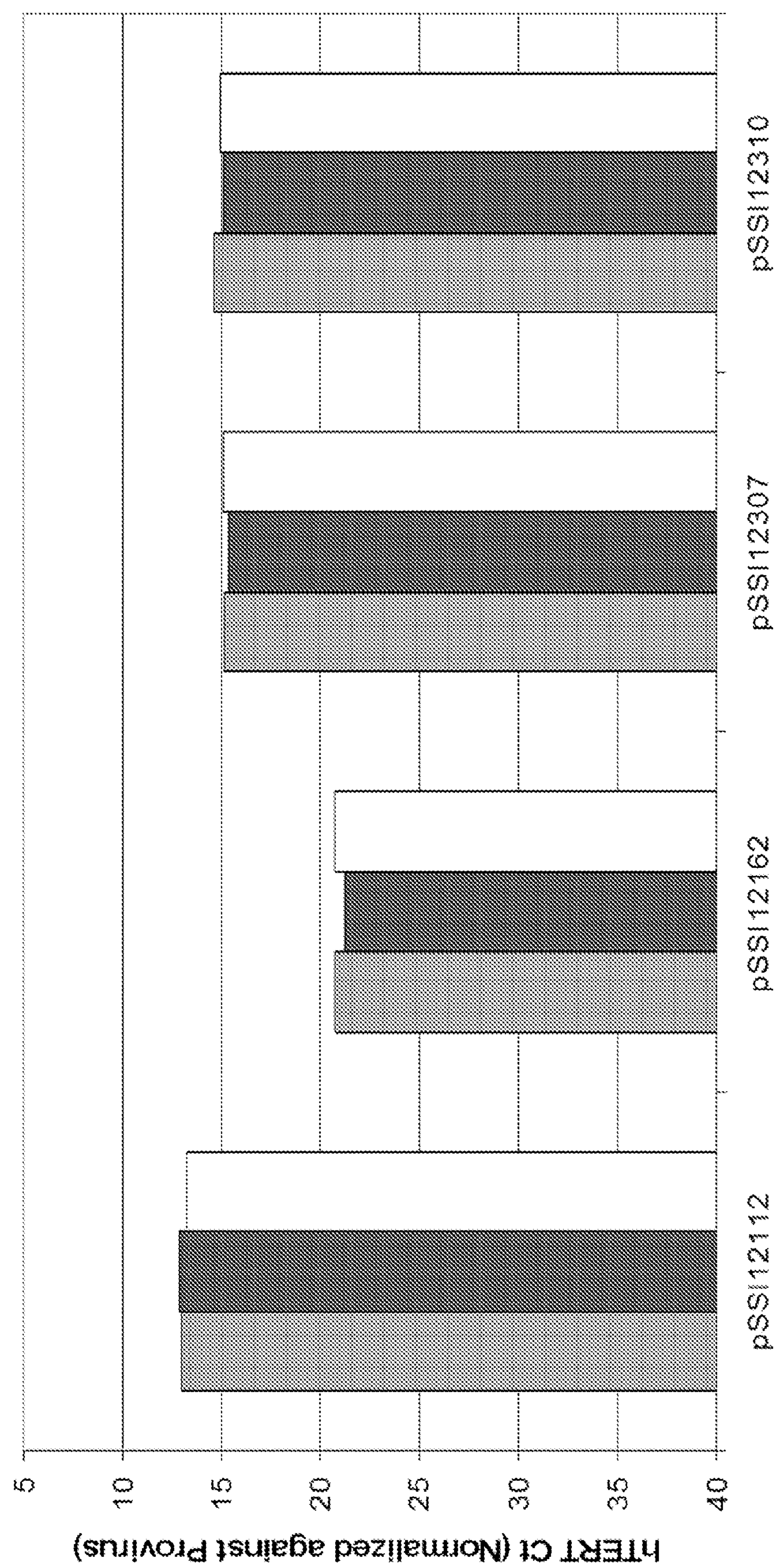
FIG. 5 illustrates RT-PCR results for hTERT Ct (normalized against provirus) using the vectors pSSI12112, pSSI12162, pSSI12307 and pSSI12310 where sample cells are collected at 14 days post BSD selection, 24 days post infection.

FIG. 5 illustrates RT-PCR results for hTERT Ct (normalized against provirus) using the vectors pSSI12112, pSSI12162, pSSI12307 and pSSI12310 where sample cells are collected at 14 days post BSD selection, 24 days post infection.

Figure 6:
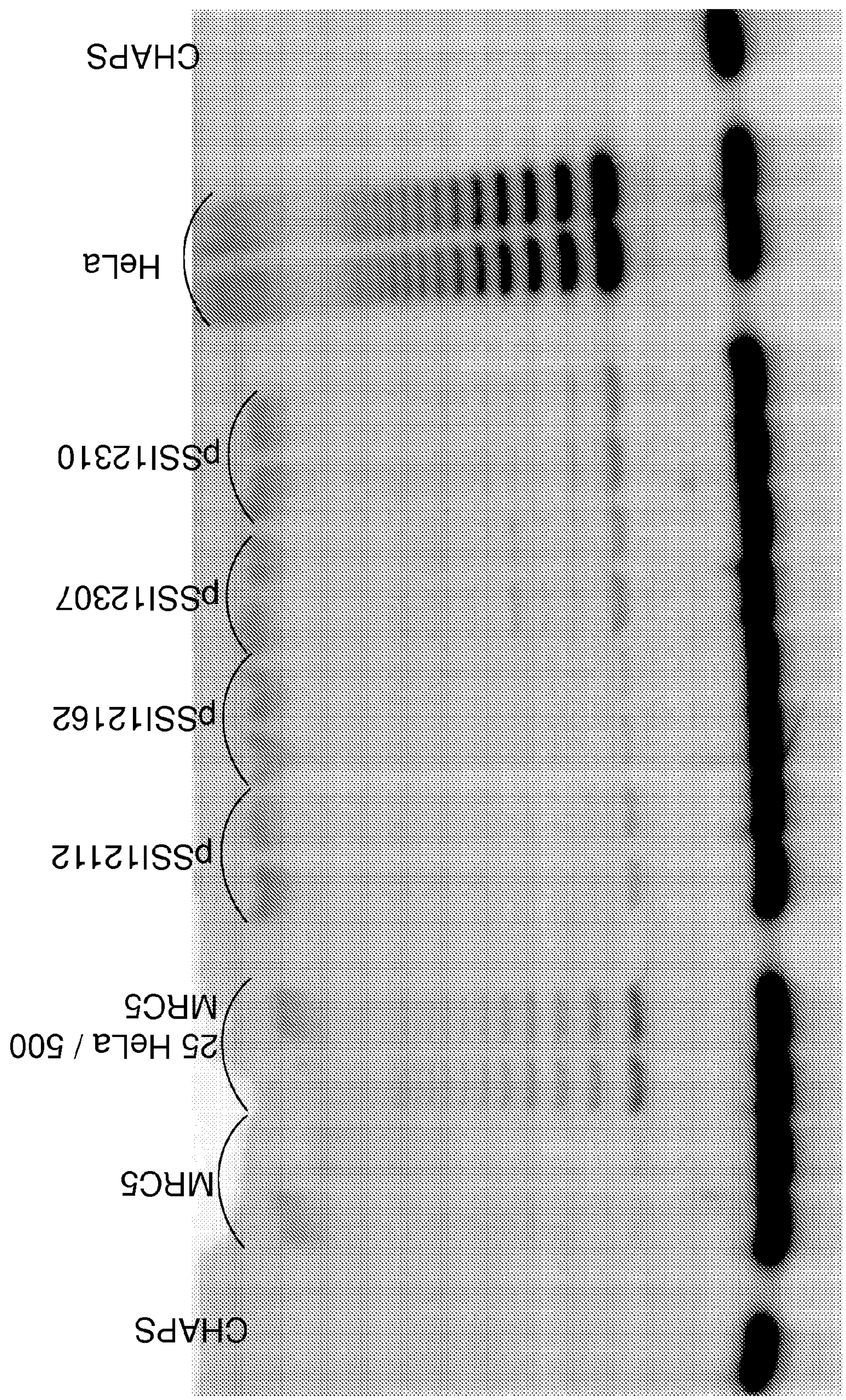
FIG. 6 depicts the results of a TRAP Assay using the vectors pSSI12112, pSSI12162, pSSI12307 and pSSI12310 where sample cells are collected at 49 days post BSD selection, 59 days post infection.

FIG. 6 depicts the results of a TRAP Assay using the vectors pSSI12112, pSSI12162, pSSI12307 and pSSI12310 where sample cells are collected at 49 days post BSD selection, 59 days post infection.

Figure 7:
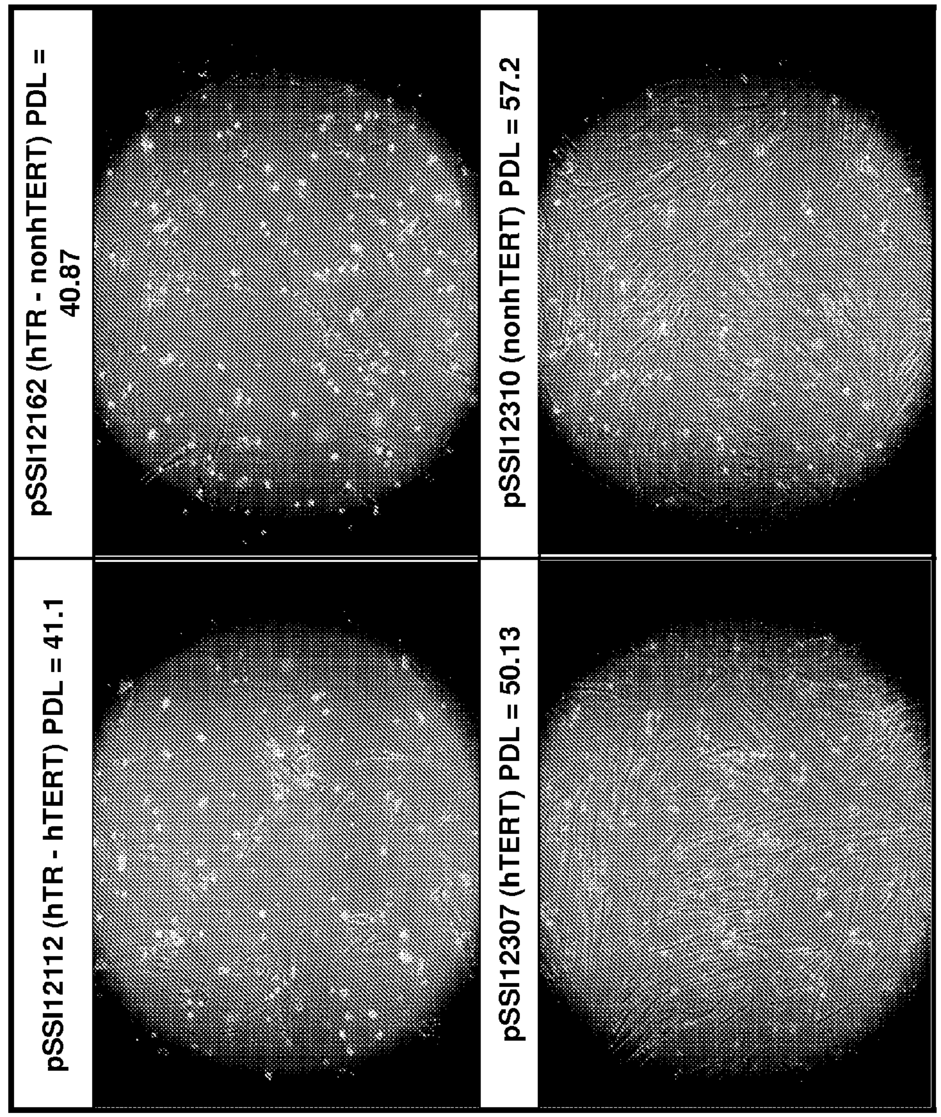
FIG. 7 depicts images comparing cell growth of cells that were maintained in 1.5 ug/ml BSD for 55 days post selection using the vectors pSSI12112, pSSI12162, pSSI12307 and pSSI12310.

FIG. 7 depicts images comparing cell growth of cells that were maintained in 1.5 ug/ml BSD for 55 days post selection using the vectors pSSI12112, pSSI12162, pSSI12307 and pSSI12310.

```
pSSI14342
                                                         (SEQ ID NO: 1)
TCACAGAACCCTAGTATTCAACCTGCCACCTCCCTCCCAACACACAGAGTACACAGTCCTTTCTC

CCCGGCTGGCCTTAAAAAGCATCATATCATGGGTAACAGACATATTCTTAGGTGTTATATTCCACA

CGGTTTCCTGTCGAGCCAAACGCTCATCAAGTGATATTAATAAACTCCCCGGGCAGCTCACTTAA

GTTCATGTCGCTGTCCAGCTGCTGAGCCACAGGCTGCTGTCCAACTTGCGGTTGCTTAACGGGC

GGCGAAGGAGAAGTCCACGCCTACATGGGGGGAGAGTCATAATCGTGCATCAGGATAGGGCGG

TGGTGCTGCAGCAGCGCGCGAATAAACTGCTGCCGCCGCCGCTCCGTCCTGCAGGAATACAACA

TGGCAGTGGTCTCCTCAGCGATGATTCGCACCGCCCGCAGCATAAGGCGCTTGTCCTCCGGGCA

CAGCAGCGCACCCTGATCTCACTTAAATCAGCACAGTAACTGCAGCACAGCACCACAATATTGTT

CAAAATCCCACAGTGCAAGGCGCTGTATCCAAAGCTCATGGCGGGGACCACAGAACCCACGTGG

CCATCATACCACAAGCGCAGGTAGATTAAGTGGCGACCCCTCATAAACACGCTGGACATAAACAT

TACCTCTTTTGGCATGTTGTAATTCACCACCTCCCGGTACCATATAAACCTCTGATTAAACATGGC

GCCATCCACCACCATCCTAAACCAGCTGGCCAAAACCTGCCCCGCCGGGNTATACACTGCAGGG

AACCGGGACTTGGACAATGACAAGTGGGAGAGCCCAGGACTCGTAACCATGGATCATCATGCTC

GTCATGATATCAATGTTGGCACAACACAGGCACACGTGCATACACTTCCTCAGGATTACAAGCTC

CTCCCGCGTTAGAACCATATCCCAGGGAACAACCCATTCCTGAATCAGCGTAAATCCCACACTGC

AGGGAAGACCTCGCACGTAACTCACGTTGTGCATTGTCAAAGTGTTACATTCGGGCAGCAGCGG

ATGATCCTCCAGTATGGTAGCGCGGGTTTCTGTCTCAAAAGGAGGTAGACGATCCCTACTGTACG

GAGTGCGCCGAGACAACCGAGATCGTGTTGGTCGTAGTGTCATGCCAAATGGAACGCCGGACGT

AGTCATATTTCCTGAAGCAAAACCAGGTGCGGGCGTGACAAACAGATCTGCGTCTCCGGTCTCG

CCGCTTAGATCGCTCTGTGTAGTAGTTGTAGTATATCCACTCTCTCAAAGCATCCAGGCGCCCCC

TGGCTTCGGGTTCTATGTAAACTCCTTCATGCGCCGCTGCCCTGATAACATCCACCACCGCAGAA
```

-continued

TAAGCCACACCCAGCCAACCTACACATTCGTTCTGCGAGTCACACACGGGAGGAGCGGGAAGAG

CTGGAAGAACCATGTTTTTTTTTTTATTCCAAAAGATTATCCAAAACCTCAAAATGAAGATCTATTA

AGTGAACGCGCTCCCCTCCGGTGGCGTGGTCAAACTCTACAGCCAAAGAACAGATAATGGCATT

TGTAAGATGTTGCACAATGGCTTCCAAAAGGCAAACGGCCCTCACGTCCAAGTGGACGTAAAGG

CTAAACCCTTCAGGGTGAATCTCCTCTATAAACATTCCAGCACCTTCAACCATGCCCAAATAATTC

TCATCTCGCCACCTTCTCAATATATCTCTAAGCAAATCCCGAATATTTAAGTCCGGGCCATTGTAA

AAAATTTGGCTCCAGAGCGCCCTCCACCTTCAGCCTCAAGCAGCGAATCATGATTGCAAAAATTC

AGGTTCCTCACAGACCTGTATAAGATTCAAAAGCGGAACATTAACAAAAATACCGCGATCCCGTA

GGTCCCTTCGCAGGGCCAGCTGAACATAATCGTGCAGGTCTGCACGGACCAGCGCGGCCACTT

CCCCGCCAGGAACCATGACAAAAGAACCCACACTGATTATGACACGCATACTCGGAGCTATGCTA

ACCAGCGTAGCCCCGATGTAAGCTTGTTGCATGGGCGGCGATATAAAATGCAAGGTGCTGCTCA

AAAAATCAGGCAAAGCCTCGCGCAAAAAAGAAAGCACATCGTAGTCATGCTCATGCAGATAAAGG

CAGGTAAGCTCCGGAACCACCACAGAAAAAGACACCATTTTTCTCTCAAACATGTCTGCGGGTTT

CTGCATAAACACAAAATAAAATAACAAAAAAACATTTAAACATTAGAAGCCTGTCTTACAACAGGAA

AAACAACCCTTATAAGCATAAGACGGACTACGGCCATGCCGGCGTGACCGTAAAAAAACTGGTCA

CCGTGATTAAAAAGCACCACCGACAGCTCCTCGGTCAGTCCGGAGTCATAATGTAAGACTCGGTA

AACACATCAGGTTGATTCACATCGGTCAGTGTTAAAAAGCGACCGAAATAGCCNGGGGGAATACA

ATACCCGCAGGCGTAGAGACAACATTACAGCCCCCATAGGAGGTATAACAAAATTAATAGGAGAG

AAAAACACATAAACACCTGAAAAACCCTCCTGCCTAGGCAAAATAGCACCCTCCCGCTCCAGAAC

AACATACAGCGCTTCCACAGCGGCAGCCATAACAGTCAGCCTTACCAGTAAAAAAGAAAACCTAT

TAAAAAAACACCACTCGACACGGCACCAGCTCAATCAGTCACAGTGTAAAAAAGGGCCAAGTGCA

GAGCGAGTATATATAGGACTAAAAAATGACGGTAACGGTTAAAGTCCACAAAAAACACCCAGAAA

ACCGCACGCGAACCTACGCCCAGAAACGAAAGCCAAAAAACCCACAACTTCCTCAAATCGTCACT

TCCGTTTTCCCACGTTACGTCACTTCCCATTTTAAGAAAACTACAATTCCCAACACATACAAGTTAC

TCCGCCCTAAAACCTACGTCACCCGCCCCGTTCCCACGCCCCGCGCCACGTCACAAACTCCACC

CCCTCATTATCATATTGGCTTCAATCCAAAATAAGGTATATTATTGATGATGTTAATTAACATGCAT

GGATCCATATGCGGTGTGAAATACCGCACAGATGCGTAAGGAGAAAATACCGCATCAGGCGCTC

TTCCGCTTCCTCGCTCACTGACTCGCTGCGCTCGGTCGTTCGGCTGCGGCGAGCGGTATCAGCT

CACTCAAAGGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTCCATAGGCT

CCGCCCCCCTGACGAGCATCACAAAAATCGACGCTCAAGTCAGAGGTGGCGAAACCCGACAGGA

CTATAAAGATACCAGGCGTTTCCCCCTGGAAGCTCCCTCGTGCGCTCTCCTGTTCCGACCCTGCC

GCTTACCGGATACCTGTCCGCCTTTCTCCCTTCGGGAAGCGTGGCGCTTTCTCATAGCTCACGCT

GTAGGTATCTCAGTTCGGTGTAGGTCGTTCGCTCCAAGCTGGGCTGTGTGCACGAACCCCCCGT

TCAGCCCGACCGCTGCGCCTTATCCGGTAACTATCGTCTTGAGTCCAACCCGGTAAGACACGAC

TTATCGCCACTGGCAGCAGCCACTGGTAACAGGATTAGCAGAGCGAGGTATGTAGGCGGTGCTA

CAGAGTTCTTGAAGTGGTGGCCTAACTACGGCTACACTAGAAGGACAGTATTTGGTATCTGCGCT

CTGCTGAAGCCAGTTACCTTCGGAAAAAGAGTTGGTAGCTCTTGATCCGGCAAACAAACCACCGC

TGGTAGCGGTGGTTTTTTTGTTTGCAAGCAGCAGATTACGCGCAGAAAAAAAGGATCTCAAGAAG

ATCCTTTGATCTTTTCTACGGGGTCTGACGCTCAGTGGAACGAAAACTCACGTTAAGGGATTTTG

-continued

GTCATGAGATTATCAAAAAGGATCTTCACCTAGATCCTTTTAAATTAAAAATGAAGTTTTAAATCAA

TCTAAAGTATATATGAGTAAACTTGGTCTGACAGTTACCAATGCTTAATCAGTGAGGCACCTATCT

CAGCGATCTGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCACCGGCTC

CAGATTTATCAGCAATAAACCAGCCAGCCGGAAGGGCCGAGCGCAGAAGTGGTCCTGCAACTTT

ATCCGCCTCCATCCAGTCTATTAATTGTTGCCGGGAAGCTAGAGTAAGTAGTTCGCCAGTTAATA

GTTTGCGCAACGTTGTTGCCATTGCTGCAGCCATGAGATTATCAAAAAGGATCTTCACCTAGATC

CTTTTCACGTAGAAAGCCAGTCCGCAGAAACGGTGCTGACCCCGGATGAATGTCAGCTACTGGG

CTATCTGGACAAGGGAAAACGCAAGCGCAAAGAGAAAGCAGGTAGCTTGCAGTGGGCTTACATG

GCGATAGCTAGACTGGGCGGTTTTATGGACAGCAAGCGAACCGGAATTGCCAGCTGGGGCGCC

CTCTGGTAAGGTTGGGAAGCCCTGCAAAGTAAACTGGATGGCTTTCTTGCCGCCAAGGATCTGAT

GGCGCAGGGGATCAAGCTCTGATCAAGAGACAGGATGAGGATCGTTTCGCATGATTGAACAAGA

TGGATTGCACGCAGGTTCTCCGGCCGCTTGGGTGGAGAGGCTATTCGGCTATGACTGGGCACAA

CAGACAATCGGCTGCTCTGATGCCGCCGTGTTCCGGCTGTCAGCGCAGGGGCGCCCGGTTCTTT

TTGTCAAGACCGACCTGTCCGGTGCCCTGAATGAACTGCAAGACGAGGCAGCGCGGCTATCGTG

GCTGGCCACGACGGGCGTTCCTTGCGCAGCTGTGCTCGACGTTGTCACTGAAGCGGGAAGGGA

CTGGCTGCTATTGGGCGAAGTGCCGGGGCAGGATCTCCTGTCATCTCACCTTGCTCCTGCCGAG

AAAGTATCCATCATGGCTGATGCAATGCGGCGGCTGCATACGCTTGATCCGGCTACCTGCCCATT

CGACCACCAAGCGAAACATCGCATCGAGCGAGCACGTACTCGGATGGAAGCCGGTCTTGTCGAT

CAGGATGATCTGGACGAAGAGCATCAGGGGCTCGCGCCAGCCGAACTGTTCGCCAGGCTCAAG

GCGAGCATGCCCGACGGCGAGGATCTCGTCGTGACCCATGGCGATGCCTGCTTGCCGAATATCA

TGGTGGAAAATGGCCGCTTTTCTGGATTCATCGACTGTGGCCGGCTGGGTGTGGCGGACCGCTA

TCAGGACATAGCGTTGGCTACCCGTGATATTGCTGAAGAGCTTGGCGGCGAATGGGCTGACCGC

TTCCTCGTGCTTTACGGTATCGCCGCTCCCGATTCGCAGCGCATCGCCTTCTATCGCCTTCTTGA

CGAGTTCTTCTGAATTTTGTTAAAATTTTTGTTAAATCAGCTCATTTTTTAACCAATAGGCCGAAAT

CGGCAACATCCCTTATAAATCAAAAGAATAGACCGCGATAGGGTTGAGTGTTGTTCCAGTTTGGA

ACAAGAGTCCACTATTAAAGAACGTGGACTCCAACGTCAAAGGGCGAAAAACCGTCTATCAGGGC

GATGGCCCACTACGTGAACCATCACCCAAATCAAGTTTTTTGCGGTCGAGGTGCCGTAAAGCTCT

AAATCGGAACCCTAAAGGGAGCCCCCGATTTAGAGCTTGACGGGGAAAGCCGGCGAACGTGGC

GAGAAAGGAAGGGAAGAAAGCGAAAGGAGCGGGCGCTAGGGCGCTGGCAAGTGTAGCGGTCA

CGCTGCGCGTAACCACCACACCCGCGCGCTTAATGCGCCGCTACAGGGCGCGTCCATTCGCCA

TTCAGGATCGAATTAATTCTTAATTAACATCATCAATAATATACCTTATTTTGGATTGAAGCCAATAT

GATAATGAGGGGGTGGAGTTTGTGACGTGGCGCGGGGCGTGGGAACGGGGCGGGTGACGTAG

TAGTGTGGCGGAAGTGTGATGTTGCAAGTGTGGCGGAACACATGTAAGCGACGGATGTGGCAAA

AGTGACGTTTTTGGTGTGCGCCGGTGTACACAGGAAGTGACAATTTTCGCGCGGTTTTAGGCGG

ATGTTGTAGTAAATTTGGGCGTAACCGAGTAAGATTTGGCCATTTTCGCGGGAAAACTGAATAAG

AGGAAGTGAAATCTGAATAATTTTGTGTTACTCATAGCGCGTAATACTGGTACCGCGGCCGCCTC

GAGTCTAGAGATATCGAATTCAAGCTTAAGGTGCACGGCCCACGTGGCCACTAGTAATTTTTCTG

CAGAAAACGTACCCGGGGATCCTCTAGGATCCCACCGAAAGGTTGCTCCTTAACACAGGCTAAG

GACCAGCTTCTTTGGGAGAGAACAGACGCAGGGGCGGGAGGGAAAAAGGGAGAGGCAGACGTC

ACTTCCCCTTGGCGGCTCTGGCAGCAGATTGGTCGGTTGAGTGGCAGAAAGGCAGACGGGGAC

-continued

TGGGCAAGGCACTGTCGGTGACATCACGGACAGGGCGACTTCTATGTAGATGAGGCAGCGCAG

AGGCTGCTGCTTCGCCACTTGCTGCTTCGCCACGAAGGAGTTCCCGTGCCCTGGGAGCGGGTTC

AGGACCGCGGATCGGAAGTGAGAATCCCAGCTGTGTGTCAGGGCTGGAAAGGGCTCGGGAGTG

CGCGGGGCAAGTGACCGTGTGTGTAAAGAGTGAGGCGTATGAGGCTGTGTCGGGGCAGAGCCC

GAAGATCCGGGTTGCGGAGGGTGGGCCTGGGAGGGGTGGTGGCCATTTTTTGTCTAACCCTAAC

TGAGAAGGGCGTAGGCGCCGTGCTTTTGCTCCCCGCGCGCTGTTTTTCTCGCTGACTTTCAGCG

GGCGGAAAAGCCTCGGCCTGCCGCCTTCCACCGTTCATTCTAGAGCAAACAAAAAATGTCAGCT

GCTGGCCCGTTCGCCCCTCCCGGGGACCTGCGGCGGGTCGCCTGCCCAGCCCCCGAACCCCG

CCTGGAGGCCGCGGTCGGCCCGGGGCTTCTCCGGAGGCACCCACTGCCACCGCGAAGAGTTG

GGCTCTGTCAGCCGCGGGTCTCTCGGGGGCGAGGGCGAGGTTCAGGCCTTTCAGGCCGCAGG

AAGAGGAACGGAGCGAGTCCCCGCGCGCGGCGCGATTCCCTGAGCTGTGGGACGTGCACCCA

GGACTCGGCTCACACATGCAGTTCGCTTTCCTGTTGGTGGGGGGAACGCCGATCGTGCGCATCC

GTCACCCCTCGCCGGCAATGGGGGCTTGTGAACCCCCAAACCTGACTGACTGGGCCAGTGTGCT

GCAAATTGGCAGGAGACGTGAAGGCACCTCCAAAGTCGACTTTCTGGAGTTTCAAAAACAGACC

GTACGATGCATTAGTTATTAATAGTAATCAATTACGGGGTCATTAGTTCATAGCCCATATATGGAG

TTCCGCGTTACATAACTTACGGTAAATGGCCCGCCTGGCTGACCGCCCAACGACCCCCGCCCAT

TGACGTCAATAATGACGTATGTTCCCATAGTAACGCCAATAGGGACTTTCCATTGACGTCAATGG

GTGGAGTATTTACGGTAAACTGCCCACTTGGCAGTACATCAAGTGTATCATATGCCAAGTACGCC

CCCTATTGACGTCAATGACGGTAAATGGCCCGCCTGGCATTATGCCCAGTACATGACCTTATGGG

ACTTTCCTACTTGGCAGTACATCTACGTATTAGTCATCGCTATTACCATGGTGATGCGGTTTTGGC

AGTACATCAATGGGCGTGGATAGCGGTTTGACTCACGGGGATTTCCAAGTCTCCACCCCATTGAC

GTCAATGGGAGTTTGTTTTGGCACCAAAATCAACGGGACTTTCCAAAATGTCGTAACAACTCCGC

CCCATTGACGCAAATGGGCGGTAGGCGTGTACGGTGGGAGGTCTATATAAGCAGAGCTGGTTTA

GTGAACCGTCAGATCCGCTAGCCCCACCATGCCGCGCGCTCCCCGCTGCCGAGCCGTGCGCTC

CCTGCTGCGCAGCCACTACCGCGAGGTGCTGCCGCTGGCCACGTTCGTGCGGCGCCTGGGGC

CCCAGGGCTGGCGGCTGGTGCAGCGCGGGGACCCGGCGGCTTTCCGCGCGCTGGTGGCCCAG

TGCCTGGTGTGCGTGCCCTGGGACGCACGGCCGCCCCCCGCCGCCCCCTCCTTCCGCCAGGTG

TCCTGCCTGAAGGAGCTGGTGGCCCGAGTGCTGCAGAGGCTGTGCGAGCGCGGCGCGAAGAAC

GTGCTGGCCTTCGGCTTCGCGCTGCTGGACGGGGCCCGCGGGGGCCCCCCCGAGGCCTTCAC

CACCAGCGTGCGCAGCTACCTGCCCAACACGGTGACCGACGCACTGCGGGGGAGCGGGGCGT

GGGGGCTGCTGTTGCGCCGCGTGGGCGACGACGTGCTGGTTCACCTGCTGGCACGCTGCGCG

CTCTTTGTGCTGGTGGCTCCCAGCTGCGCCTACCAGGTGTGCGGGCCGCCGCTGTACCAGCTC

GGCGCTGCCACTCAGGCCCGGCCCCCGCCACACGCTAGTGGACCCCGAAGGCGTCTGGGATG

CGAACGGGCCTGGAACCATAGCGTCAGGGAGGCCGGGGTCCCCCTGGGCCTGCCAGCCCCGG

GTGCGAGGAGGCGCGGGGGCAGTGCCAGCCGAAGTCTGCCGTTGCCCAAGAGGCCCAGGCGT

GGCGCTGCCCCTGAGCCGGAGCGGACGCCCGTTGGGCAGGGGTCCTGGGCCCACCCGGGCAG

GACGCGTGGACCGAGTGACCGTGGTTTCTGTGTGGTGTCACCTGCCAGACCCGCCGAAGAAGC

CACCTCTTTGGAGGGTGCGCTCTCTGGCACGCGCCACTCCCACCCATCCGTGGGCCGCCAGCA

CCACGCGGGCCCCCCATCCACATCGCGGCCACCACGTCCCTGGGACACGCCTTGTCCCCCGGT

GTACGCCGAGACCAAGCACTTCCTCTACTCCTCAGGCGACAAGGAGCAGCTGCGGCCCTCCTTC

-continued

CTACTCAGCTCTCTGAGGCCCAGCCTGACTGGCGCTCGGAGGCTCGTGGAGACCATCTTTCTGG

GTTCCAGGCCCTGGATGCCAGGGACTCCCCGCAGGTTGCCCCGCCTGCCCCAGCGCTACTGGC

AAATGCGGCCCCTGTTTCTGGAGCTGCTTGGGAACCACGCGCAGTGCCCCTACGGGGTGCTCCT

CAAGACGCACTGCCCGCTGCGAGCTGCGGTCACCCCAGCAGCCGGTGTCTGTGCCCGGGAGAA

GCCCCAGGGCTCTGTGGCGGCCCCCGAGGAGGAGGACACAGACCCCCGTCGCCTGGTGCAGC

TGCTCCGCCAGCACAGCAGCCCCTGGCAGGTGTACGGCTTCGTGCGGGCCTGCCTGCGCCGGC

TGGTGCCCCCAGGCCTCTGGGGCTCCAGGCACAACGAACGCCGCTTCCTCAGGAACACCAAGA

AGTTCATCTCCCTGGGGAAGCATGCCAAGCTCTCGCTGCAGGAGCTGACGTGGAAGATGAGCGT

GCGGGGCTGCGCTTGGCTGCGCAGGAGCCCAGGGGTTGGCTGTGTTCCGGCCGCAGAGCACC

GTCTGCGTGAGGAGATCCTGGCCAAGTTCCTGCACTGGCTGATGAGTGTGTACGTCGTCGAGCT

GCTCAGGTCTTTCTTTTATGTCACGGAGACCACGTTTCAAAAGAACAGGCTCTTTTTCTACCGGAA

GAGTGTCTGGAGCAAGTTGCAAAGCATTGGAATCAGACAGCACTTGAAGAGGGTGCAGCTGCGG

GAGCTGTCGGAAGCAGAGGTCAGGCAGCATCGGGAAGCCAGGCCCGCCCTGCTGACGTCCAGA

CTCCGCTTCATCCCCAAGCCTGACGGGCTGCGGCCGATTGTGAACATGGACTACGTCGTGGGAG

CCAGAACGTTCCGCAGAGAAAAGAGGGCCGAGCGTCTCACCTCCAGGGTGAAGGCACTGTTCA

GCGTGCTCAACTACGAGCGGGCGCGGCGCCCCGGCCTCCTGGGCGCCTCTGTGCTGGGCCTG

GACGATATCCACAGGGCCTGGCGCACCTTCGTGCTGCGTGTGCGGGCCCAGGACCCGCCGCCT

GAGCTGTACTTTGTCAAGGTGGATGTGACGGGCGCGTACGACACCATCCCCCAGGACAGGCTCA

CGGAGGTCATCGCCAGCATCATCAAACCCCAGAACACGTACTGCGTGCGTCGGTATGCCGTGGT

CCAGAAGGCCGCCCATGGGCACGTCCGCAAGGCCTTCAAGAGCCACGTCTCTACCTTGACAGAC

CTCCAGCCGTACATGCGACAGTTCGTGGCTCACCTGCAGGAGACCAGCCCGCTGAGGGATGCC

GTCGTCATCGAGCAGAGCTCCTCCCTGAATGAGGCCAGCAGTGGCCTCTTCGACGTCTTCCTAC

GCTTCATGTGCCACCACGCCGTGCGCATCAGGGGCAAGTCCTACGTCCAGTGCCAGGGGATCC

CGCAGGGCTCCATCCTCTCCACGCTGCTCTGCAGCCTGTGCTACGGCGACATGGAGAACAAGCT

GTTTGCGGGGATTCGGCGGGACGGGCTGCTCCTGCGTTTGGTGGATGATTTCTTGTTGGTGACA

CCTCACCTCACCCACGCGAAAACCTTCCTCAGGACCCTGGTCCGAGGTGTCCCTGAGTATGGCT

GCGTGGTGAACTTGCGGAAGACAGTGGTGAACTTCCCTGTAGAAGACGAGGCCCTGGGTGGCA

CGGCTTTTGTTCAGATGCCGGCCCACGGCCTATTCCCCTGGTGCGGCCTGCTGCTGGATACCCG

GACCCTGGAGGTGCAGAGCGACTACTCCAGCTATGCCCGGACCTCCATCAGAGCCAGTCTCACC

TTCAACCGCGGCTTCAAGGCTGGGAGGAACATGCGTCGCAAACTCTTTGGGGTCTTGCGGCTGA

AGTGTCACAGCCTGTTTCTGGATTTGCAGGTGAACAGCCTCCAGACGGTGTGCACCAACATCTAC

AAGATCCTCCTGCTGCAGGCGTACAGGTTTCACGCATGTGTGCTGCAGCTCCCATTTCATCAGCA

AGTTTGGAAGAACCCCACATTTTTCCTGCGCGTCATCTCTGACACGGCCTCCCTCTGCTACTCCA

TCCTGAAAGCCAAGAACGCAGGGATGTCGCTGGGGGCCAAGGGCGCCGCCGGCCCTCTGCCCT

CCGAGGCCGTGCAGTGGCTGTGCCACCAAGCATTCCTGCTCAAGCTGACTCGACACCGTGTCAC

CTACGTGCCACTCCTGGGGTCACTCAGGACAGCCCAGACGCAGCTGAGTCGGAAGCTCCCGGG

GACGACGCTGACTGCCCTGGAGGCCGCAGCCAACCCGGCACTGCCCTCAGACTTCAAGACCAT

CCTGGACTGAGTCGAAACTCGCGGCCGCCATATGCATCCTAGGCCTATTAATATTCCGGAGTATA

CGTAGCCGGCTAACGTTAACTTGTTTATTGCAGCTTATAATGGTTACAAATAAAGCAATAGCATCA

CAAATTTCACAAATAAAGCATTTTTTTCACTGCATTCTAGTTGTGGTTTGTCCAAACTCATCAATGT

ATCTTAACGCGGATCTGGGCGTGGTTAAGGGTGGGAAAGAATATATAAGGTGGGGGTCTTATGTA

-continued

GTTTTGTATCTGTTTTGCAGCAGCCGCCGCCGCCATGAGCACCAACTCGTTTGATGGAAGCATTG

TGAGCTCATATTTGACAACGCGCATGCCCCCATGGGCCGGGGTGCGTCAGAATGTGATGGGCTC

CAGCATTGATGGTCGCCCCGTCCTGCCCGCAAACTCTACTACCTTGACCTACGAGACCGTGTCT

GGAACGCCGTTGGAGACTGCAGCCTCCGCCGCCGCTTCAGCCGCTGCAGCCACCGCCCGCGG

GATTGTGACTGACTTTGCTTTCCTGAGCCCGCTTGCAAGCAGTGCAGCTTCCCGTTCATCCGCCC

GCGATGACAAGTTGACGGCTCTTTTGGCACAATTGGATTCTTTGACCCGGGAACTTAATGTCGTT

TCTCAGCAGCTGTTGGATCTGCGCCAGCAGGTTTCTGCCCTGAAGGCTTCCTCCCCTCCCAATG

CGGTTTAAAACATAAATAAAAAACCAGACTCTGTTTGGATTTGGATCAAGCAAGTGTCTTGCTGTC

TTTATTTAGGGGTTTTGCGCGCGCGGTAGGCCCGGGACCAGCGGTCTCGGTCGTTGAGGGTCCT

GTGTATTTTTTCCAGGACGTGGTAAAGGTGACTCTGGATGTTCAGATACATGGGCATAAGCCCGT

CTCTGGGGTGGAGGTAGCACCACTGCAGAGCTTCATGCTGCGGGGTGGTGTTGTAGATGATCCA

GTCGTAGCAGGAGCGCTGGGCGTGGTGCCTAAAAATGTCTTTCAGTAGCAAGCTGATTGCCAGG

GGCAGGCCCTTGGTGTAAGTGTTTACAAAGCGGTTAAGCTGGGATGGGTGCATACGTGGGGATA

TGAGATGCATCTTGGACTGTATTTTTAGGTTGGCTATGTTCCCAGCCATATCCCTCCGGGGATTCA

TGTTGTGCAGAACCACCAGCACAGTGTATCCGGTGCACTTGGGAAATTTGTCATGTAGCTTAGAA

GGAAATGCGTGGAAGAACTTGGAGACGCCCTTGTGACCTCCAAGATTTTCCATGCATTCGTCCAT

AATGATGGCAATGGGCCCACGGGCGGCGGCCTGGGCGAAGATATTTCTGGGATCACTAACGTCA

TAGTTGTGTTCCAGGATGAGATCGTCATAGGCCATTTTTACAAAGCGCGGGCGGAGGGTGCCAG

ACTGCGGTATAATGGTTCCATCCGGCCCAGGGGCGTAGTTACCCTCACAGATTTGCATTTCCCAC

GCTTTGAGTTCAGATGGGGGGATCATGTCTACCTGCGGGGCGATGAAGAAAACGGTTTCCGGGG

TAGGGGAGATCAGCTGGGAAGAAAGCAGGTTCCTGAGCAGCTGCGACTTACCGCAGCCGGTGG

GCCCGTAAATCACACCTATTACCGGGTGCAACTGGTAGTTAAGAGAGCTGCAGCTGCCGTCATC

CCTGAGCAGGGGGGCCACTTCGTTAAGCATGTCCCTGACTCGCATGTTTTCCCTGACCAAATCC

GCCAGAAGGCGCTCGCCGCCCAGCGATAGCAGTTCTTGCAAGGAAGCAAAGTTTTTCAACGGTT

TGAGACCGTCCGCCGTAGGCATGCTTTTGAGCGTTTGACCAAGCAGTTCCAGGCGGTCCCACAG

CTCGGTCACCTGCTCTACGGCATCTCGATCCAGCATATCTCCTCGTTTCGCGGGTTGGGGCGGC

TTTCGCTGTACGGCAGTAGTCGGTGCTCGTCCAGACGGGCCAGGGTCATGTCTTTCCACGGGCG

CAGGGTCCTCGTCAGCGTAGTCTGGGTCACGGTGAAGGGGTGCGCTCCGGGCTGCGCGCTGGC

CAGGGTGCGCTTGAGGCTGGTCCTGCTGGTGCTGAAGCGCTGCCGGTCTTCGCCCTGCGCGTC

GGCCAGGTAGCATTTGACCATGGTGTCATAGTCCAGCCCCTCCGCGGCGTGGCCCTTGGCGCG

CAGCTTGCCCTTGGAGGAGGCGCCGCACGAGGGGCAGTGCAGACTTTTGAGGGCGTAGAGCTT

GGGCGCGAGAAATACCGATTCCGGGGAGTAGGCATCCGCGCCGCAGGCCCCGCAGACGGTCTC

GCATTCCACGAGCCAGGTGAGCTCTGGCCGTTCGGGGTCAAAAACCAGGTTTCCCCCATGCTTT

TTGATGCGTTTCTTACCTCTGGTTTCCATGAGCCGGTGTCCACGCTCGGTGACGAAAAGGCTGTC

CGTGTCCCCGTATACAGACTTGAGAGGCCTGTCCTCGAGCGGTGTTCCGCGGTCCTCCTCGTAT

AGAAACTCGGACCACTCTGAGACAAAGGCTCGCGTCCAGGCCAGCACGAAGGAGGCTAAGTGG

GAGGGGTAGCGGTCGTTGTCCACTAGGGGGTCCACTCGCTCCAGGGTGTGAAGACACATGTCG

CCCTCTTCGGCATCAAGGAAGGTGATTGGTTTGTAGGTGTAGGCCACGTGACCGGGTGTTCCTG

AAGGGGGGCTATAAAAGGGGGTGGGGGCGCGTTCGTCCTCACTCTCTTCCGCATCGCTGTCTGC

GAGGGCCAGCTGTTGGGGTGAGTACTCCCTCTGAAAAGCGGGCATGACTTCTGCGCTAAGATTG

-continued

TCAGTTTCCAAAAACGAGGAGGATTTGATATTCACCTGGCCCGCGGTGATGCCTTTGAGGGTGG

CCGCATCCATCTGGTCAGAAAAGACAATCTTTTTGTTGTCAAGCTTGGTGGCAAACGACCCGTAG

AGGGCGTTGGACAGCAACTTGGCGATGGAGCGCAGGGTTTGGTTTTTGTCGCGATCGGCGCGC

TCCTTGGCCGCGATGTTTAGCTGCACGTATTCGCGCGCAACGCACCGCCATTCGGGAAAGACGG

TGGTGCGCTCGTCGGGCACCAGGTGCACGCGCCAACCGCGGTTGTGCAGGGTGACAAGGTCAA

CGCTGGTGGCTACCTCTCCGCGTAGGCGCTCGTTGGTCCAGCAGAGGCGGCCGCCCTTGCGCG

AGCAGAATGGCGGTAGGGGGTCTAGCTGCGTCTCGTCCGGGGGGTCTGCGTCCACGGTAAAGA

CCCCGGGCAGCAGGCGCGCGTCGAAGTAGTCTATCTTGCATCCTTGCAAGTCTAGCGCCTGCTG

CCATGCGCGGGCGGCAAGCGCGCGCTCGTATGGGTTGAGTGGGGGACCCCATGGCATGGGGT

GGGTGAGCGCGGAGGCGTACATGCCGCAAATGTCGTAAACGTAGAGGGGCTCTCTGAGTATTCC

AAGATATGTAGGGTAGCATCTTCCACCGCGGATGCTGGCGCGCACGTAATCGTATAGTTCGTGC

GAGGGAGCGAGGAGGTCGGGACCGAGGTTGCTACGGGCGGGCTGCTCTGCTCGGAAGACTATC

TGCCTGAAGATGGCATGTGAGTTGGATGATATGGTTGGACGCTGGAAGACGTTGAAGCTGGCGT

CTGTGAGACCTACCGCGTCACGCACGAAGGAGGCGTAGGAGTCGCGCAGCTTGTTGACCAGCT

CGGCGGTGACCTGCACGTCTAGGGCGCAGTAGTCCAGGGTTTCCTTGATGATGTCATACTTATC

CTGTCCCTTTTTTTTCCACAGCTCGCGGTTGAGGACAAACTCTTCGCGGTCTTTCCAGTACTCTTG

GATCGGAAACCCGTCGGCCTCCGAACGGTAAGAGCCTAGCATGTAGAACTGGTTGACGGCCTGG

TAGGCGCAGCATCCCTTTTCTACGGGTAGCGCGTATGCCTGCGCGGCCTTCCGGAGCGAGGTGT

GGGTGAGCGCAAAGGTGTCCCTGACCATGACTTTGAGGTACTGGTATTTGAAGTCAGTGTCGTC

GCATCCGCCCTGCTCCCAGAGCAAAAAGTCCGTGCGCTTTTTGGAACGCGGATTTGGCAGGGCG

AAGGTGACATCGTTGAAGAGTATCTTTCCCGCGCGAGGCATAAAGTTGCGTGTGATGCGGAAGG

GTCCCGGCACCTCGGAACGGTTGTTAATTACCTGGGCGGCGAGCACGATCTCGTCAAAGCCGTT

GATGTTGTGGCCCACAATGTAAAGTTCCAAGAAGCGCGGGATGCCCTTGATGGAAGGCAATTTTT

TAAGTTCCTCGTAGGTGAGCTCTTCAGGGGAGCTGAGCCCGTGCTCTGAAAGGGCCCAGTCTGC

AAGATGAGGGTTGGAAGCGACGAATGAGCTCCACAGGTCACGGGCCATTAGCATTTGCAGGTGG

TCGCGAAAGGTCCTAAACTGGCGACCTATGGCCATTTTTTCTGGGGTGATGCAGTAGAAGGTAAG

CGGGTCTTGTTCCCAGCGGTCCCATCCAAGGTTCGCGGCTAGGTCTCGCGCGGCAGTCACTAGA

GGCTCATCTCCGCCGAACTTCATGACCAGCATGAAGGGCACGAGCTGCTTCCCAAAGGCCCCCA

TCCAAGTATAGGTCTCTACATCGTAGGTGACAAAGAGACGCTCGGTGCGAGGATGCGAGCCGAT

CGGGAAGAACTGGATCTCCCGCCACCAATTGGAGGAGTGGCTATTGATGTGGTGAAAGTAGAAG

TCCCTGCGACGGGCCGAACACTCGTGCTGGCTTTTGTAAAAACGTGCGCAGTACTGGCAGCGGT

GCACGGGCTGTACATCCTGCACGAGGTTGACCTGACGACCGCGCACAAGGAAGCAGAGTGGGA

ATTTGAGCCCCTCGCCTGGCGGGTTTGGCTGGTGGTCTTCTACTTCGGCTGCTTGTCCTTGACC

GTCTGGCTGCTCGAGGGGAGTTACGGTGGATCGGACCACCACGCCGCGCGAGCCCAAAGTCCA

GATGTCCGCGCGCGGCGGTCGGAGCTTGATGACAACATCGCGCAGATGGGAGCTGTCCATGGT

CTGGAGCTCCCGCGGCGTCAGGTCAGGCGGGAGCTCCTGCAGGTTTACCTCGCATAGACGGGT

CAGGGCGCGGGCTAGATCCAGGTGATACCTAATTTCCAGGGGCTGGTTGGTGGCGGCGTCGAT

GGCTTGCAAGAGGCCGCATCCCCGCGGCGCGACTACGGTACCGCGCGGCGGGCGGTGGGCCG

CGGGGGTGTCCTTGGATGATGCATCTAAAAGCGGTGACGCGGGCGAGCCCCCGGAGGTAGGGG

GGGCTCCGGACCCGCCGGGAGAGGGGGCAGGGGCACGTCGGCGCCGCGCGCGGGCAGGAGC

TGGTGCTGCGCGCGTAGGTTGCTGGCGAACGCGACGACGCGGCGGTTGATCTCCTGAATCTGG

-continued

CGCCTCTGCGTGAAGACGACGGGCCCGGTGAGCTTGAGCCTGAAAGAGAGTTCGACAGAATCAA

TTTCGGTGTCGTTGACGGCGGCCTGGCGCAAAATCTCCTGCACGTCTCCTGAGTTGTCTTGATAG

GCGATCTCGGCCATGAACTGCTCGATCTCTTCCTCCTGGAGATCTCCGCGTCCGGCTCGCTCCA

CGGTGGCGGCGAGGTCGTTGGAAATGCGGGCCATGAGCTGCGAGAAGGCGTTGAGGCCTCCCT

CGTTCCAGACGCGGCTGTAGACCACGCCCCCTTCGGCATCGCGGGCGCGCATGACCACCTGCG

CGAGATTGAGCTCCACGTGCCGGGCGAAGACGGCGTAGTTTCGCAGGCGCTGAAAGAGGTAGT

TGAGGGTGGTGGCGGTGTGTTCTGCCACGAAGAAGTACATAACCCAGCGTCGCAACGTGGATTC

GTTGATATCCCCCAAGGCCTCAAGGCGCTCCATGGCCTCGTAGAAGTCCACGGCGAAGTTGAAA

AACTGGGAGTTGCGCGCCGACACGGTTAACTCCTCCTCCAGAAGACGGATGAGCTCGGCGACA

GTGTCGCGCACCTCGCGCTCAAAGGCTACAGGGGCCTCTTCTTCTTCTTCAATCTCCTCTTCCAT

AAGGGCCTCCCCTTCTTCTTCTTCTGGCGGCGGTGGGGGAGGGGGGACACGGCGGCGACGAC

GGCGCACCGGGAGGCGGTCGACAAAGCGCTCGATCATCTCCCCGCGGCGACGGCGCATGGTCT

CGGTGACGGCGCGGCCGTTCTCGCGGGGGCGCAGTTGGAAGACGCCGCCCGTCATGTCCCGG

TTATGGGTTGGCGGGGGGCTGCCATGCGGCAGGGATACGGCGCTAACGATGCATCTCAACAATT

GTTGTGTAGGTACTCCGCCGCCGAGGGACCTGAGCGAGTCCGCATCGACCGGATCGGAAAACC

TCTCGAGAAAGGCGTCTAACCAGTCACAGTCGCAAGGTAGGCTGAGCACCGTGGCGGGCGGCA

GCGGGCGGCGGTCGGGGTTGTTTCTGGCGGAGGTGCTGCTGATGATGTAATTAAAGTAGGCGG

TCTTGAGACGGCGGATGGTCGACAGAAGCACCATGTCCTTGGGTCCGGCCTGCTGAATGCGCAG

GCGGTCGGCCATGCCCCAGGCTTCGTTTTGACATCGGCGCAGGTCTTTGTAGTAGTCTTGCATG

AGCCTTTCTACCGGCACTTCTTCTTCTCCTTCCTCTTGTCCTGCATCTCTTGCATCTATCGCTGCG

GCGGCGGCGGAGTTTGGCCGTAGGTGGCGCCCTCTTCCTCCCATGCGTGTGACCCCGAAGCCC

CTCATCGGCTGAAGCAGGGCTAGGTCGGCGACAACGCGCTCGGCTAATATGGCCTGCTGCACCT

GCGTGAGGGTAGACTGGAAGTCATCCATGTCCACAAAGCGGTGGTATGCGCCCGTGTTGATGGT

GTAAGTGCAGTTGGCCATAACGGACCAGTTAACGGTCTGGTGACCCGGCTGCGAGAGCTCGGTG

TACCTGAGACGCGAGTAAGCCCTCGAGTCAAATACGTAGTCGTTGCAAGTCCGCACCAGGTACT

GGTATCCCACCAAAAAGTGCGGCGGCGGCTGGCGGTAGAGGGGCCAGCGTAGGGTGGCCGGG

GCTCCGGGGGCGAGATCTTCCAACATAAGGCGATGATATCCGTAGATGTACCTGGACATCCAGG

TGATGCCGGCGGCGGTGGTGGAGGCGCGCGGAAAGTCGCGGACGCGGTTCCAGATGTTGCGC

AGCGGCAAAAAGTGCTCCATGGTCGGGACGCTCTGGCCGGTCAGGCGCGCGCAATCGTTGACG

CTCTACCGTGCAAAAGGAGAGCCTGTAAGCGGGCACTCTTCCGTGGTCTGGTGGATAAATTCGC

AAGGGTATCATGGCGGACGACCGGGGTTCGAGCCCCGTATCCGGCCGTCCGCCGTGATCCATG

CGGTTACCGCCCGCGTGTCGAACCCAGGTGTGCGACGTCAGACAACGGGGGAGTGCTCCTTTT

GGCTTCCTTCCAGGCGCGGCGGCTGCTGCGCTAGCTTTTTTGGCCACTGGCCGCGCGCAGCGT

AAGCGGTTAGGCTGGAAAGCGAAAGCATTAAGTGGCTCGCTCCCTGTAGCCGGAGGGTTATTTT

CCAAGGGTTGAGTCGCGGGACCCCCGGTTCGAGTCTCGGACCGGCCGGACTGCGGCGAACGG

GGGTTTGCCTCCCCGTCATGCAAGACCCCGCTTGCAAATTCCTCCGGAAACAGGGACGAGCCCC

TTTTTTGCTTTTCCCAGATGCATCCGGTGCTGCGGCAGATGCGCCCCCCTCCTCAGCAGCGGCA

AGAGCAAGAGCAGCGGCAGACATGCAGGGCACCCTCCCCTCCTCCTACCGCGTCAGGAGGGGC

GACATCCGCGGTTGACGCGGCAGCAGATGGTGATTACGAACCCCCGCGGCGCCGGGCCCGGC

ACTACCTGGACTTGGAGGAGGGCGAGGGCCTGGCGCGGCTAGGAGCGCCCTCTCCTGAGCGGT

-continued

```
ACCCAAGGGTGCAGCTGAAGCGTGATACGCGTGAGGCGTACGTGCCGCGGCAGAACCTGTTTC

GCGACCGCGAGGGAGAGGAGCCCGAGGAGATGCGGGATCGAAAGTTCCACGCAGGGCGCGAG

CTGCGGCATGGCCTGAATCGCGAGCGGTTGCTGCGCGAGGAGGACTTTGAGCCCGACGCGCGA

ACCGGGATTAGTCCCGCGCGCGCACACGTGGCGGCCGCCGACCTGGTAACCGCATACGAGCAG

ACGGTGAACCAGGAGATTAACTTTCAAAAAAGCTTTAACAACCACGTGCGTACGCTTGTGGCGCG

CGAGGAGGTGGCTATAGGACTGATGCATCTGTGGGACTTTGTAAGCGCGCTGGAGCAAAACCCA

AATAGCAAGCCGCTCATGGCGCAGCTGTTCCTTATAGTGCAGCACAGCAGGGACAACGAGGCAT

TCAGGGATGCGCTGCTAAACATAGTAGAGCCCGAGGGCCGCTGGCTGCTCGATTTGATAAACAT

CCTGCAGAGCATAGTGGTGCAGGAGCGCAGCTTGAGCCTGGCTGACAAGGTGGCCGCCATCAA

CTATTCCATGCTTAGCCTGGGCAAGTTTTACGCCCGCAAGATATACCATACCCCTTACGTTCCCAT

AGACAAGGAGGTAAAGATCGAGGGGTTCTACATGCGCATGGCGCTGAAGGTGCTTACCTTGAGC

GACGACCTGGGCGTTTATCGCAACGAGCGCATCCACAAGGCCGTGAGCGTGAGCCGGCGGCGC

GAGCTCAGCGACCGCGAGCTGATGCACAGCCTGCAAAGGGCCCTGGCTGGCACGGGCAGCGG

CGATAGAGAGGCCGAGTCCTACTTTGACGCGGGCGCTGACCTGCGCTGGGCCCCAAGCCGACG

CGCCCTGGAGGCAGCTGGGGCCGGACCTGGGCTGGCGGTGGCACCCGCGCGCGCTGGCAACG

TCGGCGGCGTGGAGGAATATGACGAGGACGATGAGTACGAGCCAGAGGACGGCGAGTACTAAG

CGGTGATGTTTCTGATCAGATGATGCAAGACGCAACGGACCCGGCGGTGCGGGCGGCGCTGCA

GAGCCAGCCGTCCGGCCTTAACTCCACGGACGACTGGCGCCAGGTCATGGACCGCATCATGTC

GCTGACTGCGCGCAATCCTGACGCGTTCCGGCAGCAGCCGCAGGCCAACCGGCTCTCCGCAAT

TCTGGAAGCGGTGGTCCCGGCGCGCGCAAACCCCACGCACGAGAAGGTGCTGGCGATCGTAAA

CGCGCTGGCCGAAAACAGGGCCATCCGGCCCGACGAGGCCGGCCTGGTCTACGACGCGCTGC

TTCAGCGCGTGGCTCGTTACAACAGCGGCAACGTGCAGACCAACCTGGACCGGCTGGTGGGGG

ATGTGCGCGAGGCCGTGGCGCAGCGTGAGCGCGCGCAGCAGCAGGGCAACCTGGGCTCCATG

GTTGCACTAAACGCCTTCCTGAGTACACAGCCCGCCAACGTGCCGCGGGGACAGGAGGACTACA

CCAACTTTGTGAGCGCACTGCGGCTAATGGTGACTGAGACACCGCAAAGTGAGGTGTACCAGTC

TGGGCCAGACTATTTTTTCCAGACCAGTAGACAAGGCCTGCAGACCGTAAACCTGAGCCAGGCTT

TCAAAAACTTGCAGGGGCTGTGGGGGGTGCGGGCTCCCACAGGCGACCGCGCGACCGTGTCTA

GCTTGCTGACGCCCAACTCGCGCCTGTTGCTGCTGCTAATAGCGCCCTTCACGGACAGTGGCAG

CGTGTCCCGGGACACATACCTAGGTCACTTGCTGACACTGTACCGCGAGGCCATAGGTCAGGCG

CATGTGGACGAGCATACTTTCCAGGAGATTACAAGTGTCAGCCGCGCGCTGGGGCAGGAGGACA

CGGGCAGCCTGGAGGCAACCCTAAACTACCTGCTGACCAACCGGCGGCAGAAGATCCCCTCGTT

GCACAGTTTAAACAGCGAGGAGGAGCGCATTTTGCGCTACGTGCAGCAGAGCGTGAGCCTTAAC

CTGATGCGCGACGGGGTAACGCCCAGCGTGGCGCTGGACATGACCGCGCGCAACATGGAACCG

GGCATGTATGCCTCAAACCGGCCGTTTATCAACCGCCTAATGGACTACTTGCATCGCGCGGCCG

CCGTGAACCCCGAGTATTTCACCAATGCCATCTTGAACCCGCACTGGCTACCGCCCCCTGGTTTC

TACACCGGGGGATTCGAGGTGCCCGAGGGTAACGATGGATTCCTCTGGGACGACATAGACGACA

GCGTGTTTTCCCCGCAACCGCAGACCCTGCTAGAGTTGCAACAGCGCGAGCAGGCAGAGGCGG

CGCTGCGAAAGGAAAGCTTCCGCAGGCCAAGCAGCTTGTCCGATCTAGGCGCTGCGGCCCCGC

GGTCAGATGCTAGTAGCCCATTTCCAAGCTTGATAGGGTCTCTTACCAGCACTCGCACCACCCGC

CCGCGCCTGCTGGGCGAGGAGGAGTACCTAAACAACTCGCTGCTGCAGCCGCAGCGCGAAAAA

AACCTGCCTCCGGCATTTCCCAACAACGGGATAGAGAGCCTAGTGGACAAGATGAGTAGATGGA
```

-continued

AGACGTACGCGCAGGAGCACAGGGACGTGCCAGGCCCGCGCCCGCCCACCCGTCGTCAAAGG

CACGACCGTCAGCGGGGTCTGGTGTGGGAGGACGATGACTCGGCAGACGACAGCAGCGTCCTG

GATTTGGGAGGGAGTGGCAACCCGTTTGCGCACCTTCGCCCCAGGCTGGGGAGAATGTTTTAAA

AAAAAAAAAGCATGATGCAAAATAAAAAACTCACCAAGGCCATGGCACCGAGCGTTGGTTTTCTT

GTATTCCCCTTAGTATGCGGCGCGCGGCGATGTATGAGGAAGGTCCTCCTCCCTCCTACGAGAG

TGTGGTGAGCGCGGCGCCAGTGGCGGCGGCGCTGGGTTCTCCCTTCGATGCTCCCCTGGACCC

GCCGTTTGTGCCTCCGCGGTACCTGCGGCCTACCGGGGGGAGAAACAGCATCCGTTACTCTGA

GTTGGCACCCCTATTCGACACCACCCGTGTGTACCTGGTGGACAACAAGTCAACGGATGTGGCA

TCCCTGAACTACCAGAACGACCACAGCAACTTTCTGACCACGGTCATTCAAAACAATGACTACAG

CCCGGGGGAGGCAAGCACACAGACCATCAATCTTGACGACCGGTCGCACTGGGGCGGCGACCT

GAAAACCATCCTGCATACCAACATGCCAAATGTGAACGAGTTCATGTTTACCAATAAGTTTAAGGC

GCGGGTGATGGTGTCGCGCTTGCCTACTAAGGACAATCAGGTGGAGCTGAAATACGAGTGGGTG

GAGTTCACGCTGCCCGAGGGCAACTACTCCGAGACCATGACCATAGACCTTATGAACAACGCGA

TCGTGGAGCACTACTTGAAAGTGGGCAGACAGAACGGGGTTCTGGAAAGCGACATCGGGGTAAA

GTTTGACACCCGCAACTTCAGACTGGGGTTTGACCCCGTCACTGGTCTTGTCATGCCTGGGGTAT

ATACAAACGAAGCCTTCCATCCAGACATCATTTTGCTGCCAGGATGCGGGGTGGACTTCACCCAC

AGCCGCCTGAGCAACTTGTTGGGCATCCGCAAGCGGCAACCCTTCCAGGAGGGCTTTAGGATCA

CCTACGATGATCTGGAGGGTGGTAACATTCCCGCACTGTTGGATGTGGACGCCTACCAGGCGAG

CTTGAAAGATGACACCGAACAGGGCGGGGGTGGCGCAGGCGGCAGCAACAGCAGTGGCAGCG

GCGCGGAAGAGAACTCCAACGCGGCAGCCGCGGCAATGCAGCCGGTGGAGGACATGAACGATC

ATGCCATTCGCGGCGACACCTTTGCCACACGGGCTGAGGAGAAGCGCGCTGAGGCCGAAGCAG

CGGCCGAAGCTGCCGCCCCCGCTGCGCAACCCGAGGTCGAGAAGCCTCAGAAGAAACCGGTGA

TCAAACCCCTGACAGAGGACAGCAAGAAACGCAGTTACAACCTAATAAGCAATGACAGCACCTTC

ACCCAGTACCGCAGCTGGTACCTTGCATACAACTACGGCGACCCTCAGACCGGAATCCGCTCAT

GGACCCTGCTTTGCACTCCTGACGTAACCTGCGGCTCGGAGCAGGTCTACTGGTCGTTGCCAGA

CATGATGCAAGACCCCGTGACCTTCCGCTCCACGCGCCAGATCAGCAACTTTCCGGTGGTGGGC

GCCGAGCTGTTGCCCGTGCACTCCAAGAGCTTCTACAACGACCAGGCCGTCTACTCCCAACTCA

TCCGCCAGTTTACCTCTCTGACCCACGTGTTCAATCGCTTTCCCGAGAACCAGATTTTGGCGCGC

CCGCCAGCCCCCACCATCACCACCGTCAGTGAAAACGTTCCTGCTCTCACAGATCACGGGACGC

TACCGCTGCGCAACAGCATCGGAGGAGTCCAGCGAGTGACCATTACTGACGCCAGACGCCGCA

CCTGCCCCTACGTTTACAAGGCCCTGGGCATAGTCTCGCCGCGCGTCCTATCGAGCCGCACTTT

TTGAGCAAGCATGTCCATCCTTATATCGCCCAGCAATAACACAGGCTGGGGCCTGCGCTTCCCAA

GCAAGATGTTTGGCGGGGCCAAGAAGCGCTCCGACCAACACCCAGTGCGCGTGCGCGGGCACT

ACCGCGCGCCCTGGGGCGCGCACAAACGCGGCCGCACTGGGCGCACCACCGTCGATGACGCC

ATCGACGCGGTGGTGGAGGAGGCGCGCAACTACACGCCCACGCCGCCACCAGTGTCCACAGTG

GACGCGGCCATTCAGACCGTGGTGCGCGGAGCCCGGCGCTATGCTAAAATGAAGAGACGGCGG

AGGCGCGTAGCACGTCGCCACCGCCGCCGACCCGGCACTGCCGCCCAACGCGCGGCGGCGGC

CCTGCTTAACCGCGCACGTCGCACCGGCCGACGGGCGGCCATGCGGGCCGCTCGAAGGCTGG

CCGCGGGTATTGTCACTGTGCCCCCCAGGTCCAGGCGACGAGCGGCCGCCGCAGCAGCCGCG

GCCATTAGTGCTATGACTCAGGGTCGCAGGGGCAACGTGTATTGGGTGCGCGACTCGGTTAGCG

-continued

GCCTGCGCGTGCCCGTGCGCACCCGCCCCCCGCGCAACTAGATTGCAAGAAAAAACTACTTAGA

CTCGTACTGTTGTATGTATCCAGCGGCGGCGGCGCGCAACGAAGCTATGTCCAAGCGCAAAATC

AAAGAAGAGATGCTCCAGGTCATCGCGCCGGAGATCTATGGCCCCCCGAAGAAGGAAGAGCAG

GATTACAAGCCCCGAAAGCTAAAGCGGGTCAAAAAGAAAAAGAAAGATGATGATGATGAACTTGA

CGACGAGGTGGAACTGCTGCACGCTACCGCGCCCAGGCGACGGGTACAGTGGAAAGGTCGACG

CGTAAAACGTGTTTTGCGACCCGGCACCACCGTAGTCTTTACGCCCGGTGAGCGCTCCACCCGC

ACCTACAAGCGCGTGTATGATGAGGTGTACGGCGACGAGGACCTGCTTGAGCAGGCCAACGAG

CGCCTCGGGGAGTTTGCCTACGGAAAGCGGCATAAGGACATGCTGGCGTTGCCGCTGGACGAG

GGCAACCCAACACCTAGCCTAAAGCCCGTAACACTGCAGCAGGTGCTGCCCGCGCTTGCACCGT

CCGAAGAAAAGCGCGGCCTAAAGCGCGAGTCTGGTGACTTGGCACCCACCGTGCAGCTGATGG

TACCCAAGCGCCAGCGACTGGAAGATGTCTTGGAAAAAATGACCGTGGAACCTGGGCTGGAGCC

CGAGGTCCGCGTGCGGCCAATCAAGCAGGTGGCGCCGGGACTGGGCGTGCAGACCGTGGACG

TTCAGATACCCACTACCAGTAGCACCAGTATTGCCACCGCCACAGAGGGCATGGAGACACAAAC

GTCCCCGGTTGCCTCAGCGGTGGCGGATGCCGCGGTGCAGGCGGTCGCTGCGGCCGCGTCCA

AGACCTCTACGGAGGTGCAAACGGACCCGTGGATGTTTCGCGTTTCAGCCCCCCGGCGCCCGC

GCGGTTCGAGGAAGTACGGCGCCGCCAGCGCGCTACTGCCCGAATATGCCCTACATCCTTCCAT

TGCGCCTACCCCCGGCTATCGTGGCTACACCTACCGCCCCAGAAGACGAGCAACTACCCGACGC

CGAACCACCACTGGAACCCGCCGCCGCCGTCGCCGTCGCCAGCCCGTGCTGGCCCCGATTTCC

GTGCGCAGGGTGGCTCGCGAAGGAGGCAGGACCCTGGTGCTGCCAACAGCGCGCTACCACCC

CAGCATCGTTTAAAAGCCGGTCTTTGTGGTTCTTGCAGATATGGCCCTCACCTGCCGCCTCCGTT

TCCCGGTGCCGGGATTCCGAGGAAGAATGCACCGTAGGAGGGGCATGGCCGGCCACGGCCTGA

CGGGCGGCATGCGTCGTGCGCACCACCGGCGGCGGCGCGCGTCGCACCGTCGCATGCGCGGC

GGTATCCTGCCCCTCCTTATTCCACTGATCGCCGCGGCGATTGGCGCCGTGCCCGGAATTGCAT

CCGTGGCCTTGCAGGCGCAGAGACACTGATTAAAAACAAGTTGCATGTGGAAAAATCAAAATAAA

AAGTCTGGACTCTCACGCTCGCTTGGTCCTGTAACTATTTTGTAGAATGGAAGACATCAACTTTGC

GTCTCTGGCCCCGCGACACGGCTCGCGCCCGTTCATGGGAAACTGGCAAGATATCGGCACCAG

CAATATGAGCGGTGGCGCCTTCAGCTGGGGCTCGCTGTGGAGCGGCATTAAAAATTTCGGTTCC

ACCGTTAAGAACTATGGCAGCAAGGCCTGGAACAGCAGCACAGGCCAGATGCTGAGGGATAAGT

TGAAAGAGCAAAATTTCCAACAAAAGGTGGTAGATGGCCTGGCCTCTGGCATTAGCGGGGTGGT

GGACCTGGCCAACCAGGCAGTGCAAAATAAGATTAACAGTAAGCTTGATCCCCGCCCTCCCGTA

GAGGAGCCTCCACCGGCCGTGGAGACAGTGTCTCCAGAGGGGCGTGGCGAAAAGCGTCCGCG

CCCCGACAGGGAAGAAACTCTGGTGACGCAAATAGACGAGCCTCCCTCGTACGAGGAGGCACTA

AAGCAAGGCCTGCCCACCACCCGTCCCATCGCGCCCATGGCTACCGGAGTGCTGGGCCAGCAC

ACACCCGTAACGCTGGACCTGCCTCCCCCCGCCGACACCCAGCAGAAACCTGTGCTGCCAGGC

CCGACCGCCGTTGTTGTAACCCGTCCTAGCCGCGCGTCCCTGCGCCGCGCCGCCAGCGGTCCG

CGATCGTTGCGGCCCGTAGCCAGTGGCAACTGGCAAAGCACACTGAACAGCATCGTGGGTCTG

GGGGTGCAATCCCTGAAGCGCCGACGATGCTTCTGAATAGCTAACGTGTCGTATGTGTGTCATGT

ATGCGTCCATGTCGCCGCCAGAGGAGCTGCTGAGCCGCCGCGCGCCCGCTTTCCAAGATGGCT

ACCCCTTCGATGATGCCGCAGTGGTCTTACATGCACATCTCGGGCCAGGACGCCTCGGAGTACC

TGAGCCCCGGGCTGGTGCAGTTTGCCCGCGCCACCGAGACGTACTTCAGCCTGAATAACAAGTT

TAGAAACCCCACGGTGGCGCCTACGCACGACGTGACCACAGACCGGTCCCAGCGTTTGACGCT

-continued

GCGGTTCATCCCTGTGGACCGTGAGGATACTGCGTACTCGTACAAGGCGCGGTTCACCCTAGCT

GTGGGTGATAACCGTGTGCTGGACATGGCTTCCACGTACTTTGACATCCGCGGCGTGCTGGACA

GGGGCCCTACTTTTAAGCCCTACTCTGGCACTGCCTACAACGCCCTGGCTCCCAAGGGTGCCCC

AAATCCTTGCGAATGGGATGAAGCTGCTACTGCTCTTGAAATAAACCTAGAAGAAGAGGACGATG

ACAACGAAGACGAAGTAGACGAGCAAGCTGAGCAGCAAAAAACTCACGTATTTGGGCAGGCGCC

TTATTCTGGTATAAATATTACAAAGGAGGGTATTCAAATAGGTGTCGAAGGTCAAACACCTAAATA

TGCCGATAAAACATTTCAACCTGAACCTCAAATAGGAGAATCTCAGTGGTACGAAACTGAAATTAA

TCATGCAGCTGGGAGAGTCCTTAAAAAGACTACCCCAATGAAACCATGTTACGGTTCATATGCAA

AACCCACAAATGAAAATGGAGGGCAAGGCATTCTTGTAAAGCAACAAAATGGAAAGCTAGAAAGT

CAAGTGGAAATGCAATTTTTCTCAACTACTGAGGCGACCGCAGGCAATGGTGATAACTTGACTCC

TAAAGTGGTATTGTACAGTGAAGATGTAGATATAGAAACCCCAGACACTCATATTTCTTACATGCC

CACTATTAAGGAAGGTAACTCACGAGAACTAATGGGCCAACAATCTATGCCCAACAGGCCTAATT

ACATTGCTTTTAGGGACAATTTTATTGGTCTAATGTATTACAACAGCACGGGTAATATGGGTGTTC

TGGCGGGCCAAGCATCGCAGTTGAATGCTGTTGTAGATTTGCAAGACAGAAACACAGAGCTTTCA

TACCAGCTTTTGCTTGATTCCATTGGTGATAGAACCAGGTACTTTTCTATGTGGAATCAGGCTGTT

GACAGCTATGATCCAGATGTTAGAATTATTGAAAATCATGGAACTGAAGATGAACTTCCAAATTAC

TGCTTTCCACTGGGAGGTGTGATTAATACAGAGACTCTTACCAAGGTAAAACCTAAAACAGGTCA

GGAAAATGGATGGGAAAAAGATGCTACAGAATTTTCAGATAAAAATGAAATAAGAGTTGGAAATAA

TTTTGCCATGGAAATCAATCTAAATGCCAACCTGTGGAGAAATTTCCTGTACTCCAACATAGCGCT

GTATTTGCCCGACAAGCTAAAGTACAGTCCTTCCAACGTAAAAATTTCTGATAACCCAAACACCTA

CGACTACATGAACAAGCGAGTGGTGGCTCCCGGGTTAGTGGACTGCTACATTAACCTTGGAGCA

CGCTGGTCCCTTGACTATATGGACAACGTCAACCCATTTAACCACCACCGCAATGCTGGCCTGCG

CTACCGCTCAATGTTGCTGGGCAATGGTCGCTATGTGCCCTTCCACATCCAGGTGCCTCAGAAGT

TCTTTGCCATTAAAAACCTCCTTCTCCTGCCGGGCTCATACACCTACGAGTGGAACTTCAGGAAG

GATGTTAACATGGTTCTGCAGAGCTCCCTAGGAAATGACCTAAGGGTTGACGGAGCCAGCATTAA

GTTTGATAGCATTTGCCTTTACGCCACCTTCTTCCCCATGGCCCACAACACCGCCTCCACGCTTG

AGGCCATGCTTAGAAACGACACCAACGACCAGTCCTTTAACGACTATCTCTCCGCCGCCAACATG

CTCTACCCTATACCCGCCAACGCTACCAACGTGCCCATATCCATCCCCTCCCGCAACTGGGCGG

CTTTCCGCGGCTGGGCCTTCACGCGCCTTAAGACTAAGGAAACCCCATCACTGGGCTCGGGCTA

CGACCCTTATTACACCTACTCTGGCTCTATACCCTACCTAGATGGAACCTTTTACCTCAACCACAC

CTTTAAGAAGGTGGCCATTACCTTTGACTCTTCTGTCAGCTGGCCTGGCAATGACCGCCTGCTTA

CCCCCAACGAGTTTGAAATTAAGCGCTCAGTTGACGGGGAGGGTTACAACGTTGCCCAGTGTAA

CATGACCAAAGACTGGTTCCTGGTACAAATGCTAGCTAACTACAACATTGGCTACCAGGGCTTCT

ATATCCCAGAGAGCTACAAGGACCGCATGTACTCCTTCTTTAGAAACTTCCAGCCCATGAGCCGT

CAGGTGGTGGATGATACTAAATACAAGGACTACCAACAGGTGGGCATCCTACACCAACACAACAA

CTCTGGATTTGTTGGCTACCTTGCCCCCACCATGCGCGAAGGACAGGCCTACCCTGCTAACTTCC

CCTATCCGCTTATAGGCAAGACCGCAGTTGACAGCATTACCCAGAAAAAGTTTCTTTGCGATCGC

ACCCTTTGGCGCATCCCATTCTCCAGTAACTTTATGTCCATGGGCGCACTCACAGACCTGGGCCA

AAACCTTCTCTACGCCAACTCCGCCCACGCGCTAGACATGACTTTTGAGGTGGATCCCATGGACG

AGCCCACCCTTCTTTATGTTTTGTTTGAAGTCTTTGACGTGGTCCGTGTGCACCGGCCGCACCGC

-continued

GGCGTCATCGAAACCGTGTACCTGCGCACGCCCTTCTCGGCCGGCAACGCCACAACATAAAGAA

GCAAGCAACATCAACAACAGCTGCCGCCATGGGCTCCAGTGAGCAGGAACTGAAAGCCATTGTC

AAAGATCTTGGTTGTGGGCCATATTTTTTGGGCACCTATGACAAGCGCTTTCCAGGCTTTGTTTCT

CCACACAAGCTCGCCTGCGCCATAGTCAATACGGCCGGTCGCGAGACTGGGGGCGTACACTGG

ATGGCCTTTGCCTGGAACCCGCACTCAAAAACATGCTACCTCTTTGAGCCCTTTGGCTTTTCTGA

CCAGCGACTCAAGCAGGTTTACCAGTTTGAGTACGAGTCACTCCTGCGCCGTAGCGCCATTGCTT

CTTCCCCCGACCGCTGTATAACGCTGGAAAAGTCCACCCAAAGCGTACAGGGGCCCAACTCGGC

CGCCTGTGGACTATTCTGCTGCATGTTTCTCCACGCCTTTGCCAACTGGCCCCAAACTCCCATGG

ATCACAACCCCACCATGAACCTTATTACCGGGGTACCCAACTCCATGCTCAACAGTCCCCAGGTA

CAGCCCACCCTGCGTCGCAACCAGGAACAGCTCTACAGCTTCCTGGAGCGCCACTCGCCCTACT

TCCGCAGCCACAGTGCGCAGATTAGGAGCGCCACTTCTTTTTGTCACTTGAAAAACATGTAAAAA

TAATGTACTAGAGACACTTTCAATAAAGGCAAATGCTTTTATTTGTACACTCTCGGGTGATTATTTA

CCCCCACCCTTGCCGTCTGCGCCGTTTAAAAATCAAAGGGGTTCTGCCGCGCATCGCTATGCGC

CACTGGCAGGGACACGTTGCGATACTGGTGTTTAGTGCTCCACTTAAACTCAGGCACAACCATCC

GCGGCAGCTCGGTGAAGTTTTCACTCCACAGGCTGCGCACCATCACCAACGCGTTTAGCAGGTC

GGGCGCCGATATCTTGAAGTCGCAGTTGGGGCCTCCGCCCTGCGCGCGCGAGTTGCGATACAC

AGGGTTGCAGCACTGGAACACTATCAGCGCCGGGTGGTGCACGCTGGCCAGCACGCTCTTGTC

GGAGATCAGATCCGCGTCCAGGTCCTCCGCGTTGCTCAGGGCGAACGGAGTCAACTTTGGTAGC

TGCCTTCCCAAAAAGGGCGCGTGCCCAGGCTTTGAGTTGCACTCGCACCGTAGTGGCATCAAAA

GGTGACCGTGCCCGGTCTGGGCGTTAGGATACAGCGCCTGCATAAAAGCCTTGATCTGCTTAAA

AGCCACCTGAGCCTTTGCGCCTTCAGAGAAGAACATGCCGCAAGACTTGCCGGAAAACTGATTG

GCCGGACAGGCCGCGTCGTGCACGCAGCACCTTGCGTCGGTGTTGGAGATCTGCACCACATTTC

GGCCCCACCGGTTCTTCACGATCTTGGCCTTGCTAGACTGCTCCTTCAGCGCGCGCTGCCCGTT

TTCGCTCGTCACATCCATTTCAATCACGTGCTCCTTATTTATCATAATGCTTCCGTGTAGACACTTA

AGCTCGCCTTCGATCTCAGCGCAGCGGTGCAGCCACAACGCGCAGCCCGTGGGCTCGTGATGC

TTGTAGGTCACCTCTGCAAACGACTGCAGGTACGCCTGCAGGAATCGCCCCATCATCGTCACAAA

GGTCTTGTTGCTGGTGAAGGTCAGCTGCAACCCGCGGTGCTCCTCGTTCAGCCAGGTCTTGCAT

ACGGCCGCCAGAGCTTCCACTTGGTCAGGCAGTAGTTTGAAGTTCGCCTTTAGATCGTTATCCAC

GTGGTACTTGTCCATCAGCGCGCGCGCAGCCTCCATGCCCTTCTCCCACGCAGACACGATCGGC

ACACTCAGCGGGTTCATCACCGTAATTTCACTTTCCGCTTCGCTGGGCTCTTCCTCTTCCTCTTGC

GTCCGCATACCACGCGCCACTGGGTCGTCTTCATTCAGCCGCCGCACTGTGCGCTTACCTCCTT

TGCCATGCTTGATTAGCACCGGTGGGTTGCTGAAACCCACCATTTGTAGCGCCACATCTTCTCTT

TCTTCCTCGCTGTCCACGATTACCTCTGGTGATGGCGGGCGCTCGGGCTTGGGAGAAGGGCGCT

TCTTTTTCTTCTTGGGCGCAATGGCCAAATCCGCCGCCGAGGTCGATGGCCGCGGGCTGGGTGT

GCGCGGCACCAGCGCGTCTTGTGATGAGTCTTCCTCGTCCTCGGACTCGATACGCCGCCTCATC

CGCTTTTTTGGGGGCGCCCGGGGAGGCGGCGGCGACGGGGACGGGGACGACACGTCCTCCAT

GGTTGGGGGACGTCGCGCCGCACCGCGTCCGCGCTCGGGGGTGGTTTCGCGCTGCTCCTCTTC

CCGACTGGCCATTTCCTTCTCCTATAGGCAGAAAAAGATCATGGAGTCAGTCGAGAAGAAGGACA

GCCTAACCGCCCCCTCTGAGTTCGCCACCACCGCCTCCACCGATGCCGCCAACGCGCCTACCAC

CTTCCCCGTCGAGGCACCCCCGCTTGAGGAGGAGGAAGTGATTATCGAGCAGGACCCAGGTTTT

GTAAGCGAAGACGACGAGGACCGCTCAGTACCAACAGAGGATAAAAAGCAAGACCAGGACAACG

-continued

```
CAGAGGCAAACGAGGAACAAGTCGGGCGGGGGACGAAAGGCATGGCGACTACCTAGATGTGG
GAGACGACGTGCTGTTGAAGCATCTGCAGCGCCAGTGCGCCATTATCTGCGACGCGTTGCAAGA
GCGCAGCGATGTGCCCCTCGCCATAGCGGATGTCAGCCTTGCCTACGAACGCCACCTATTCTCA
CCGCGCGTACCCCCCAAACGCCAAGAAAACGGCACATGCGAGCCCAACCCGCGCCTCAACTTCT
ACCCCGTATTTGCCGTGCCAGAGGTGCTTGCCACCTATCACATCTTTTTCCAAAACTGCAAGATA
CCCCTATCCTGCCGTGCCAACCGCAGCCGAGCGGACAAGCAGCTGGCCTTGCGGCAGGGCGCT
GTCATACCTGATATCGCCTCGCTCAACGAAGTGCCAAAAATCTTTGAGGGTCTTGGACGCGACGA
GAAGCGCGCGGCAAACGCTCTGCAACAGGAAAACAGCGAAAATGAAAGTCACTCTGGAGTGTTG
GTGGAACTCGAGGGTGACAACGCGCGCCTAGCCGTACTAAAACGCAGCATCGAGGTCACCCACT
TTGCCTACCCGGCACTTAACCTACCCCCCAAGGTCATGAGCACAGTCATGAGTGAGCTGATCGT
GCGCCGTGCGCAGCCCCTGGAGAGGGATGCAAATTTGCAAGAACAAACAGAGGAGGGCCTACC
CGCAGTTGGCGACGAGCAGCTAGCGCGCTGGCTTCAAACGCGCGAGCCTGCCGACTTGGAGGA
GCGACGCAAACTAATGATGGCCGCAGTGCTCGTTACCGTGGAGCTTGAGTGCATGCAGCGGTTC
TTTGCTGACCCGGAGATGCAGCGCAAGCTAGAGGAAACATTGCACTACACCTTTCGACAGGGCT
ACGTACGCCAGGCCTGCAAGATCTCCAACGTGGAGCTCTGCAACCTGGTCTCCTACCTTGGAATT
TTGCACGAAAACCGCCTTGGGCAAAACGTGCTTCATTCCACGCTCAAGGGCGAGGCGCGCCGC
GACTACGTCCGCGACTGCGTTTACTTATTTCTATGCTACACCTGGCAGACGGCCATGGGCGTTTG
GCAGCAGTGCTTGGAGGAGTGCAACCTCAAGGAGCTGCAGAAACTGCTAAAGCAAAACTTGAAG
GACCTATGGACGGCCTTCAACGAGCGCTCCGTGGCCGCGCACCTGGCGGACATCATTTTCCCCG
AACGCCTGCTTAAAACCCTGCAACAGGGTCTGCCAGACTTCACCAGTCAAAGCATGTTGCAGAAC
TTTAGGAACTTTATCCTAGAGCGCTCAGGAATCTTGCCCGCCACCTGCTGTGCACTTCCTAGCGA
CTTTGTGCCCATTAAGTACCGCGAATGCCCTCCGCCGCTTTGGGGCCACTGCTACCTTCTGCAG
CTAGCCAACTACCTTGCCTACCACTCTGACATAATGGAAGACGTGAGCGGTGACGGTCTACTGGA
GTGTCACTGTCGCTGCAACCTATGCACCCCGCACCGCTCCCTGGTTTGCAATTCGCAGCTGCTTA
ACGAAAGTCAAATTATCGGTACCTTTGAGCTGCAGGGTCCCTCGCCTGACGAAAAGTCCGCGGC
TCCGGGGTTGAAACTCACTCCGGGGCTGTGGACGTCGGCTTACCTTCGCAAATTTGTACCTGAG
GACTACCACGCCCACGAGATTAGGTTCTACGAAGACCAATCCCGCCCGCCAAATGCGGAGCTTA
CCGCCTGCGTCATTACCCAGGGCCACATTCTTGGCCAATTGCAAGCCATCAACAAAGCCCGCCA
AGAGTTTCTGCTACGAAAGGGACGGGGGGTTTACTTGGACCCCCAGTCCGGCGAGGAGCTCAAC
CCAATCCCCCCGCCGCCGCAGCCCTATCAGCAGCAGCCGCGGGCCCTTGCTTCCCAGGATGGC
ACCCAAAAAGAAGCTGCAGCTGCCGCCGCCACCCACGGACGAGGAGGAATACTGGGACAGTCA
GGCAGAGGAGGTTTTGGACGAGGAGGAGGAGGACATGATGGAAGACTGGGAGAGCCTAGACGA
GGAAGCTTCCGAGGTCGAAGAGGTGTCAGACGAAACACCGTCACCCTCGGTCGCATTCCCCTCG
CCGGCGCCCCAGAAATCGGCAACCGGTTCCAGCATGGCTACAACCTCCGCTCCTCAGGCGCCG
CCGGCACTGCCCGTTCGCCGACCCAACCGTAGATGGGACACCACTGGAACCAGGGCCGGTAAG
TCCAAGCAGCCGCCGCCGTTAGCCCAAGAGCAACAACAGCGCCAAGGCTACCGCTCATGGCGC
GGGCACAAGAACGCCATAGTTGCTTGCTTGCAAGACTGTGGGGGCAACATCTCCTTCGCCCGCC
GCTTTCTTCTCTACCATCACGGCGTGGCCTTCCCCCGTAACATCCTGCATTACTACCGTCATCTCT
ACAGCCCATACTGCACCGGCGGCAGCGGCAGCGGCAGCAACAGCAGCGGCCACACAGAAGCAA
AGGCGACCGGATAGCAAGACTCTGACAAAGCCCAAGAAATCCACAGCGGCGGCAGCAGCAGGA
```

-continued

GGAGGAGCGCTGCGTCTGGCGCCCAACGAACCCGTATCGACCCGCGAGCTTAGAAACAGGATT

TTTCCCACTCTGTATGCTATATTTCAACAGAGCAGGGGCCAAGAACAAGAGCTGAAAATAAAAAAC

AGGTCTCTGCGATCCCTCACCCGCAGCTGCCTGTATCACAAAAGCGAAGATCAGCTTCGGCGCA

CGCTGGAAGACGCGGAGGCTCTCTTCAGTAAATACTGCGCGCTGACTCTTAAGGACTAGTTTCG

CGCCCTTTCTCAAATTTAAGCGCGAAAACTACGTCATCTCCAGCGGCCACACCCGGCGCCAGCA

CCTGTCGTCAGCGCCATTATGAGCAAGGAAATTCCCACGCCCTACATGTGGAGTTACCAGCCACA

AATGGGACTTGCGGCTGGAGCTGCCCAAGACTACTCAACCCGAATAAACTACATGAGCGCGGGA

CCCCACATGATATCCCGGGTCAACGGAATCCGCGCCCACCGAAACCGAATTCTCTTGGAACAGG

CGGCTATTACCACCACACCTCGTAATAACCTTAATCCCCGTAGTTGGCCCGCTGCCCTGGTGTAC

CAGGAAAGTCCCGCTCCCACCACTGTGGTACTTCCCAGAGACGCCCAGGCCGAAGTTCAGATGA

CTAACTCAGGGGCGCAGCTTGCGGGCGGCTTTCGTCACAGGGTGCGGTCGCCCGGGCAGGGTA

TAACTCACCTGACAATCAGAGGGCGAGGTATTCAGCTCAACGACGAGTCGGTGAGCTCCTCGCT

TGGTCTCCGTCCGGACGGGACATTTCAGATCGGCGGCGCCGGCCGTCCTTCATTCACGCCTCGT

CAGGCAATCCTAACTCTGCAGACCTCGTCCTCTGAGCCGCGCTCTGGAGGCATTGGAACTCTGC

AATTTATTGAGGAGTTTGTGCCATCGGTCTACTTTAACCCCTTCTCGGGACCTCCCGGCCACTAT

CCGGATCAATTTATTCCTAACTTTGACGCGGTAAAGGACTCGGCGGACGGCTACGACTGAATGTT

AAGTGGAGAGGCAGAGCAACTGCGCCTGAAACACCTGGTCCACTGTCGCCGCCACAAGTGCTTT

GCCCGCGACTCCGGTGAGTTTTGCTACTTTGAATTGCCCGAGGATCATATCGAGGGCCCGGCGC

ACGGCGTCCGGCTTACCGCCCAGGGAGAGCTTGCCCGTAGCCTGATTCGGGAGTTTACCCAGC

GCCCCCTGCTAGTTGAGCGGGACAGGGGACCCTGTGTTCTCACTGTGATTTGCAACTGTCCTAA

CCTTGGATTACATCAAGATCCTCTAGTTATAACTAGAGTACCCGGGGATCTTATTCCCTTTAACTA

ATAAAAAAAAATAATAAAGCATCACTTACTTAAAATCAGTTAGCAAATTTCTGTCCAGTTTATTCAG

CAGCACCTCCTTGCCCTCCTCCCAGCTCTGGTATTGCAGCTTCCTCCTGGCTGCAAACTTTCTCC

ACAATCTAAATGGAATGTCAGTTTCCTCCTGTTCCTGTCCATCCGCACCCACTATCTTCATGTTGT

TGCAGATGAAGCGCGCAAGACCGTCTGAAGATACCTTCAACCCCGTGTATCCATATGACACGGAA

ACCGGTCCTCCAACTGTGCCTTTTCTTACTCCTCCCTTTGTATCCCCCAATGGGTTTCAAGAGAGT

CCCCCTGGGGTACTCTCTTTGCGCCTATCCGAACCTCTAGTTACCTCCAATGGCATGCTTGCGCT

CAAAATGGGCAACGGCCTCTCTCTGGACGAGGCCGGCAACCTTACCTCCCAAAATGTAACCACT

GTGAGCCCACCTCTCAAAAAAACCAAGTCAAACATAAACCTGGAAATATCTGCACCCCTCACAGT

TACCTCAGAAGCCCTAACTGTGGCTGCCGCCGCACCTCTAATGGTCGCGGGCAACACACTCACC

ATGCAATCACAGGCCCCGCTAACCGTGCACGACTCCAAACTTAGCATTGCCACCCAAGGACCCC

TCACAGTGTCAGAAGGAAAGCTAGCCCTGCAAACATCAGGCCCCCTCACCACCACCGATAGCAG

TACCCTTACTATCACTGCCTCACCCCCTCTAACTACTGCCACTGGTAGCTTGGGCATTGACTTGAA

AGAGCCCATTTATACACAAAATGGAAAACTAGGACTAAAGTACGGGGCTCCTTTGCATGTAACAG

ACGACCTAAACACTTTGACCGTAGCAACTGGTCCAGGTGTGACTATTAATAATACTTCCTTGCAAA

CTAAAGTTACTGGAGCCTTGGGTTTTGATTCACAAGGCAATATGCAACTTAATGTAGCAGGAGGA

CTAAGGATTGATTCTCAAAACAGACGCCTTATACTTGATGTTAGTTATCCGTTTGATGCTCAAAAC

CAACTAAATCTAAGACTAGGACAGGGCCCTCTTTTTATAAACTCAGCCCACAACTTGGATATTAAC

TACAACAAAGGCCTTTACTTGTTTACAGCTTCAAACAATTCCAAAAAGCTTGAGGTTAACCTAAGC

ACTGCCAAGGGGTTGATGTTTGACGCTACAGCCATAGCCATTAATGCAGGAGATGGGCTTGAATT

TGGTTCACCTAATGCACCAAACACAAATCCCCTCAAAACAAAAATTGGCCATGGCCTAGAATTTGA

-continued

TTCAAACAAGGCTATGGTTCCTAAACTAGGAACTGGCCTTAGTTTTGACAGCACAGGTGCCATTA

CAGTAGGAAACAAAAATAATGATAAGCTAACTTTGTGGACCACACCAGCTCCATCTCCTAACTGTA

GACTAAATGCAGAGAAAGATGCTAAACTCACTTTGGTCTTAACAAAATGTGGCAGTCAAATACTTG

CTACAGTTTCAGTTTTGGCTGTTAAAGGCAGTTTGGCTCCAATATCTGGAACAGTTCAAAGTGCTC

ATCTTATTATAAGATTTGACGAAAATGGAGTGCTACTAAACAATTCCTTCCTGGACCCAGAATATT

GGAACTTTAGAAATGGAGATCTTACTGAAGGCACAGCCTATACAAACGCTGTTGGATTTATGCCTA

ACCTATCAGCTTATCCAAAATCTCACGGTAAAACTGCCAAAAGTAACATTGTCAGTCAAGTTTACT

TAAACGGAGACAAAACTAAACCTGTAACACTAACCATTACACTAAACGGTACACAGGAAACAGGA

GACACAACTCCAAGTGCATACTCTATGTCATTTTCATGGGACTGGTCTGGCCACAACTACATTAAT

GAAATATTTGCCACATCCTCTTACACTTTTTCATACATTGCCCAAGAATAAAGAATCGTTTGTGTTA

TGTTTCAACGTGTTTATTTTTCAATTGCAGAAAATTTCAAGTCATTTTTCATTCAGTAGTATAGCCC

CACCACCACATAGCTTATACAGATCACCGTACCTTAATCAAAC pSSI10902 (SEQ ID NO: 2):
AATGTAGTCTTATGCAATACTCTTGTAGTCTTGCAACATGGTAACGATGAGTTAGCAACATGCCTT

ACAAGGAGAGAAAAAGCACCGTGCATGCCGATTGGTGGAAGTAAGGTGGTACGATCGTGCCTTA

TTAGGAAGGCAACAGACGGGTCTGACATGGATTGGACGAACCACTGAATTGCCGCATTGCAGAG

ATATTGTATTTAAGTGCCTAGCTCGATACATAAACGGGTCTCTCTGGTTAGACCAGATCTGAGCCT

GGGAGCTCTCTGGCTAACTAGGGAACCCACTGCTTAAGCCTCAATAAAGCTTGCCTTGAGTGCTT

CAAGTAGTGTGTGCCCGTCTGTTGTGTGACTCTGGTAACTAGAGATCCCTCAGACCCTTTTAGTC

AGTGTGGAAAATCTCTAGCAGTGGCGCCCGAACAGGGACTTGAAAGCGAAAGGGAAACCAGAGG

AGCTCTCTCGACGCAGGACTCGGCTTGCTGAAGCGCGCACGGCAAGAGGCGAGGGGCGGCGA

CTGGTGAGTACGCCAAAAATTTTGACTAGCGGAGGCTAGAAGGAGAGAGATGGGTGCGAGAGCG

TCAGTATTAAGCGGGGGAGAATTAGATCGCGATGGGAAAAAATTCGGTTAAGGCCAGGGGGAAA

GAAAAAATATAAATTAAAACATATAGTATGGGCAAGCAGGGAGCTAGAACGATTCGCAGTTAATCC

TGGCCTGTTAGAAACATCAGAAGGCTGTAGACAAATACTGGGACAGCTACAACCATCCCTTCAGA

CAGGATCAGAAGAACTTAGATCATTATATAATACAGTAGCAACCCTCTATTGTGTGCATCAAAGGA

TAGAGATAAAAGACACCAAGGAAGCTTTAGACAAGATAGAGGAAGAGCAAAACAAAAGTAAGACC

ACCGCACAGCAAGCGGCCGCTGATCTTCAGACCTGGAGGAGGAGATATGAGGGACAATTGGAG

AAGTGAATTATATAAATATAAAGTAGTAAAAATTGAACCATTAGGAGTAGCACCCACCAAGGCAAA

GAGAAGAGTGGTGCAGAGAGAAAAAAGAGCAGTGGGAATAGGAGCTTTGTTCCTTGGGTTCTTG

GGAGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTGTTG

CAACTCACAGTCTGGGGCATCAAGCAGCTCCAGGCAAGAATCCTGGCTGTGGAAAGATACCTAA

AGGATCAACAGCTCCTGGGGATTTGGGGTTGCTCTGGAAAACTCATTTGCACCACTGCTGTGCCT

TGGAATGCTAGTTGGAGTAATAAATCTCTGGAACAGATTTGGAATCACACGACCTGGATGGAGTG

GGACAGAGAAATTAACAATTACACAAGCTTAATACACTCCTTAATTGAAGAATCGCAAAACCAGCA

AGAAAAGAATGAACAAGAATTATTGGAATTAGATAAATGGGCAAGTTTGTGGAATTGGTTTAACAT

AACAAATTGGCTGTGGTATATAAAATTATTCATAATGATAGTAGGAGGCTTGGTAGGTTTAAGAAT

AGTTTTTGCTGTACTTTCTATAGTGAATAGAGTTAGGCAGGGATATTCACCATTATCGTTTCAGAC

CCACCTCCCAACCCCGAGGGGACCCGACAGGCCCGAAGGAATAGAAGAAGAAGGTGGAGAGAG

AGACAGAGACAGATCCATTCGATTAGTGAACGGATCTCGACGGTATCGATTGGGCCCGAGATCT

-continued

CGCGCGCGAGGCCTGCCATGGGCATGCCTGCAGGTCGATGCGTGGCCGGCCTAGGATCCATAT

GGTACCGGTAAATGGCCCGCCTGGCTGACCGCCCAACGACCCCCGCCCATTGACGTCAATAATG

ACGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTCA

ATGACGGTAAATGGCCCGCCTGGCATTATGCCCAGTACATGACCTTATGGGACTTTCCTACTTGG

CAGTACATCTAGTATTAGTCATCGCTATTACCATGGTGATGCGGTTTTGGCAGTACATCAATGGGC

GTGGATAGCGGTTTGACTCACGGGGATTTCCAAGTCTCCACCCCATTGACGTCAATGGGAGTTTG

TTTTGGCACCAAAATCAACGGGACTTTCCAAAATGTCGTAACAACTCCGCCCCATTGACGCAAAT

GGGCGGTAGGCGTGTACGGTGGGAGGTCTATATAAGCAGAGCTCGTTTAGTGAACCGTCAGATC

GCCTGGAGACGCCATCCACGCTGTTTTGACCTCCATAGAAGACACCGGGACCGATCCAGCCTCC

GCGGCCGGGAACGGTGCATTGGAACGCGGATTCCCCGTGCCAAGAGTGACGTAAGTACCGCCT

ATAGACTCTATAGGCACACCCCTTTGGCTCTTATGCATGAATTAATACGACTCACTATAGGGAGAC

AGACTGTTCCTTTCCTGGGTCTTTTCTGCAGGCTAGCCCCACCATGCCGCGCGCTCCCCGCTGC

CGAGCCGTGCGCTCCCTGCTGCGCAGCCACTACCGCGAGGTGCTGCCGCTGGCCACGTTCGTG

CGGCGCCTGGGGCCCCAGGGCTGGCGGCTGGTGCAGCGCGGGGACCCGGCGGCTTTCCGCG

CGCTGGTGGCCCAGTGCCTGGTGTGCGTGCCCTGGGACGCACGGCCGCCCCCCGCCGCCCCC

TCCTTCCGCCAGGTGTCCTGCCTGAAGGAGCTGGTGGCCCGAGTGCTGCAGAGGCTGTGCGAG

CGCGGCGCGAAGAACGTGCTGGCCTTCGGCTTCGCGCTGCTGGACGGGGCCCGCGGGGGCCC

CCCCGAGGCCTTCACCACCAGCGTGCGCAGCTACCTGCCCAACACGGTGACCGACGCACTGCG

GGGGAGCGGGGCGTGGGGGCTGCTGTTGCGCCGCGTGGGCGACGACGTGCTGGTTCACCTGC

TGGCACGCTGCGCGCTCTTTGTGCTGGTGGCTCCCAGCTGCGCCTACCAGGTGTGCGGGCCGC

CGCTGTACCAGCTCGGCGCTGCCACTCAGGCCCGGCCCCCGCCACACGCTAGTGGACCCCGAA

GGCGTCTGGGATGCGAACGGGCCTGGAACCATAGCGTCAGGGAGGCCGGGGTCCCCCTGGGC

CTGCCAGCCCCGGGTGCGAGGAGGCGCGGGGGCAGTGCCAGCCGAAGTCTGCCGTTGCCCAA

GAGGCCCAGGCGTGGCGCTGCCCCTGAGCCGGAGCGGACGCCCGTTGGGCAGGGGTCCTGGG

CCCACCCGGGCAGGACGCGTGGACCGAGTGACCGTGGTTTCTGTGTGGTGTCACCTGCCAGAC

CCGCCGAAGAAGCCACCTCTTTGGAGGGTGCGCTCTCTGGCACGCGCCACTCCCACCCATCCGT

GGGCCGCCAGCACCACGCGGGCCCCCCATCCACATCGCGGCCACCACGTCCCTGGGACACGC

CTTGTCCCCCGGTGTACGCCGAGACCAAGCACTTCCTCTACTCCTCAGGCGACAAGGAGCAGCT

GCGGCCCTCCTTCCTACTCAGCTCTCTGAGGCCCAGCCTGACTGGCGCTCGGAGGCTCGTGGA

GACCATCTTTCTGGGTTCCAGGCCCTGGATGCCAGGGACTCCCCGCAGGTTGCCCCGCCTGCC

CCAGCGCTACTGGCAAATGCGGCCCCTGTTTCTGGAGCTGCTTGGGAACCACGCGCAGTGCCC

CTACGGGGTGCTCCTCAAGACGCACTGCCCGCTGCGAGCTGCGGTCACCCCAGCAGCCGGTGT

CTGTGCCCGGGAGAAGCCCCAGGGCTCTGTGGCGGCCCCCGAGGAGGAGGACACAGACCCCC

GTCGCCTGGTGCAGCTGCTCCGCCAGCACAGCAGCCCCTGGCAGGTGTACGGCTTCGTGCGGG

CCTGCCTGCGCCGGCTGGTGCCCCCAGGCCTCTGGGGCTCCAGGCACAACGAACGCCGCTTCC

TCAGGAACACCAAGAAGTTCATCTCCCTGGGGAAGCATGCCAAGCTCTCGCTGCAGGAGCTGAC

GTGGAAGATGAGCGTGCGGGGCTGCGCTTGGCTGCGCAGGAGCCCAGGGGTTGGCTGTGTTCC

GGCCGCAGAGCACCGTCTGCGTGAGGAGATCCTGGCCAAGTTCCTGCACTGGCTGATGAGTGT

GTACGTCGTCGAGCTGCTCAGGTCTTTCTTTTATGTCACGGAGACCACGTTTCAAAAGAACAGGC

-continued

TCTTTTTCTACCGGAAGAGTGTCTGGAGCAAGTTGCAAAGCATTGGAATCAGACAGCACTTGAAG

AGGGTGCAGCTGCGGGAGCTGTCGGAAGCAGAGGTCAGGCAGCATCGGGAAGCCAGGCCCGC

CCTGCTGACGTCCAGACTCCGCTTCATCCCCAAGCCTGACGGGCTGCGGCCGATTGTGAACATG

GACTACGTCGTGGGAGCCAGAACGTTCCGCAGAGAAAAGAGGGCCGAGCGTCTCACCTCCAGG

GTGAAGGCACTGTTCAGCGTGCTCAACTACGAGCGGGCGCGGCGCCCCGGCCTCCTGGGCGCC

TCTGTGCTGGGCCTGGACGATATCCACAGGGCCTGGCGCACCTTCGTGCTGCGTGTGCGGGCC

CAGGACCCGCCGCCTGAGCTGTACTTTGTCAAGGTGGATGTGACGGGCGCGTACGACACCATCC

CCCAGGACAGGCTCACGGAGGTCATCGCCAGCATCATCAAACCCCAGAACACGTACTGCGTGCG

TCGGTATGCCGTGGTCCAGAAGGCCGCCCATGGGCACGTCCGCAAGGCCTTCAAGAGCCACGT

CTCTACCTTGACAGACCTCCAGCCGTACATGCGACAGTTCGTGGCTCACCTGCAGGAGACCAGC

CCGCTGAGGGATGCCGTCGTCATCGAGCAGAGCTCCTCCCTGAATGAGGCCAGCAGTGGCCTC

TTCGACGTCTTCCTACGCTTCATGTGCCACCACGCCGTGCGCATCAGGGGCAAGTCCTACGTCC

AGTGCCAGGGGATCCCGCAGGGCTCCATCCTCTCCACGCTGCTCTGCAGCCTGTGCTACGGCG

ACATGGAGAACAAGCTGTTTGCGGGGATTCGGCGGGACGGGCTGCTCCTGCGTTTGGTGGATG

ATTTCTTGTTGGTGACACCTCACCTCACCCACGCGAAAACCTTCCTCAGGACCCTGGTCCGAGGT

GTCCCTGAGTATGGCTGCGTGGTGAACTTGCGGAAGACAGTGGTGAACTTCCCTGTAGAAGACG

AGGCCCTGGGTGGCACGGCTTTTGTTCAGATGCCGGCCCACGGCCTATTCCCCTGGTGCGGCC

TGCTGCTGGATACCCGGACCCTGGAGGTGCAGAGCGACTACTCCAGCTATGCCCGGACCTCCAT

CAGAGCCAGTCTCACCTTCAACCGCGGCTTCAAGGCTGGGAGGAACATGCGTCGCAAACTCTTT

GGGGTCTTGCGGCTGAAGTGTCACAGCCTGTTTCTGGATTTGCAGGTGAACAGCCTCCAGACGG

TGTGCACCAACATCTACAAGATCCTCCTGCTGCAGGCGTACAGGTTTCACGCATGTGTGCTGCAG

CTCCCATTTCATCAGCAAGTTTGGAAGAACCCCACATTTTTCCTGCGCGTCATCTCTGACACGGC

CTCCCTCTGCTACTCCATCCTGAAAGCCAAGAACGCAGGGATGTCGCTGGGGGCCAAGGGCGC

CGCCGGCCCTCTGCCCTCCGAGGCCGTGCAGTGGCTGTGCCACCAAGCATTCCTGCTCAAGCT

GACTCGACACCGTGTCACCTACGTGCCACTCCTGGGGTCACTCAGGACAGCCCAGACGCAGCTG

AGTCGGAAGCTCCCGGGGACGACGCTGACTGCCCTGGAGGCCGCAGCCAACCCGGCACTGCC

CTCAGACTTCAAGACCATCCTGGACTGAGTCGAAACTCGAGGATCCGGCTGTGGAATGTGTGTC

AGTTAGGGTGTGGAAAGTCCCCAGGCTCCCCAGCAGGCAGAAGTATGCAAAGCATGCATCTCAA

TTAGTCAGCAACCAGGTGTGGAAAGTCCCCAGGCTCCCCAGCAGGCAGAAGTATGCAAAGCATG

CATCTCAATTAGTCAGCAACCATAGTCCCGCCCCTAACTCCGCCCATCCCGCCCCTAACTCCGCC

CAGTTCCGCCCATTCTCCGCCCCATGGCTGACTAATTTTTTTTATTTATGCAGAGGCCGAGGCCG

CCTCGGCCTCTGAGCTATTCCAGAAGTAGTGAGGAGGCTTTTTTGGAGGCCGTCGGCCGCCACG

ACCGGTGCCGCCACCATCCCCTGACCCACGCCCCTGACCCCTCACAAGGAGACGACCTTCCATG

ACCGAGTACAAGCCCACGGTGCGCCTCGCCACCCGCGACGACGTCCCCCGGGCCGTACGCACC

CTCGCCGCCGCGTTCGCCGACTACCCTGCAACACGCCATACAGTGGACCCTGACCGCCACATCG

AGCGGGTCACCGAGCTGCAAGAACTCTTCCTCACGCGCGTCGGGCTCGACATCGGCAAGGTGT

GGGTCGCGGACGACGGCGCCGCGGTGGCGGTCTGGACCACGCCGGAGAGCGTCGAAGCGGG

GGCGGTGTTCGCCGAGATCGGCCCGCGCATGGCCGAGTTGAGCGGTTCCCGGCTGGCCGCGC

AGCAACAGATGGAAGGCCTCCTGGCGCCGCACCGGCCCAAGGAGCCCGCGTGGTTCCTGGCCA

CCGTCGGCGTCTCGCCCGACCACCAGGGCAAGGGTCTGGGCAGCGCCGTCGTGCTCCCCGGA

GTGGAGGCGGCCGAGCGCGCCGGGGTGCCCGCCTTCCTGGAGACCTCCGCGCCCCGCAACCT

-continued

CCCCTTCTACGAGCGGCTCGGCTTCACCGTCACCGCCGACGTCGAGGTGCCCGAAGGACCGCG

CACCTGGTGCATGACCCGCAAGCCCGGTGCCTGACGCCCGCCCCACGACCCGCAGCGCCCGAC

CGAAAGGAGCGCACGACCCCATGCATCGATAAAATAAAAGATTTTATTTAGTCTCCAGAAAAAGG

GGGGAATGAAAGACCCCACCTGTAGGTTTGGCAAGCTAGGCCTATTAATATTCCGGAGTATACGT

AGCCGGCTAACGTTAACAACCGGTACGATGCATTAGTTATTAATAGTAATCAATTACGGGGTCATT

AGTTCATAGCCCATATATGGAGTTCCGCGTTACATAACTTACGGTAAATGGCCCGCCTGGCTGAC

CGCCCAACGACCCCCGCCCATTGACGTCAATAATGACGTATGTTCCCATAGTAACGCCAATAGGG

ACTTTCCATTGACGTCAATGGGTGGAGTATTTACGGTAAACTGCCCACTTGGCAGTACATCAAGT

GTATCATATGCCAAGTACGCCCCCTATTGACGTCAATGACGGTAAATGGCCCGCCTGGCATTATG

CCCAGTACATGACCTTATGGGACTTTCCTACTTGGCAGTACATCTACGTATTAGTCATCGCTATTA

CCATGGTGATGCGGTTTTGGCAGTACATCAATGGGCGTGGATAGCGGTTTGACTCACGGGGATT

TCCAAGTCTCCACCCCATTGACGTCAATGGGAGTTTGTTTTGGCACCAAAATCAACGGGACTTTC

CAAAATGTCGTAACAACTCCGCCCCATTGACGCAAATGGGCGGTAGGCGTGTACGGTGGGAGGT

CTATATAAGCAGAGCTGGTTTAGTGAACCGTCAGATCCGCTAGCGCTACCGGACTCAGATCTCGA

GCTCAAGCTTCGAATTCTGCAGTCGACCCACCATGGCTCTTTCAAACAAGTTTATCGGAGATGAC

ATGAAAATGACCTACCATATGGATGGCTGTGTCAATGGGCATTACTTTACCGTCAAAGGTGAAGG

CAGCGGGAAGCCATACGAAGGGACGCAGACCTCGACTTTTAAAGTCACCATGGCCAACGGTGGG

CCCCTTGCATTCTCCTTTGACATACTATCTACAGTGTTCATGTATGGAAATCGATGCTTTACTGCG

TATCCTACCAGTATGCCCGACTATTTCAAACAAGCATTTCCTGACGGAATGTCATATGAAAGGACT

TTTACCTATGAAGATGGAGGAGTTGCTACAGCCAGTTGGGAAATAAGCCTTAAAGGCAACTGCTT

TGAGCACAAATCCACGTTTCATGGAGTGAACTTTCCTGCTGATGGACCTGTGATGGCGAAGATGA

CAACTGGTTGGGACCCATCTTTTGAGAAAATGACTGTCTGCGATGGAATATTGAAGGGTGATGTC

ACCGCGTTCCTCATGCTGCAAGGAGGTGGCAATTACAGATGCCAATTCCACACTTCTTACAAGAC

AAAAAAACCGGTGACGATGCCACCAAACCATGCGGTGGAACATCGCATTGCGAGGACCGACCTT

GACAAAGGTGGCAACAGTGTTCAGCTGACGGAGCACGCTGTTGCACATATAACCTCTGTTGTCCC

TTTCTAGCGGCCGCGATAATCAACCTCTGGATTACAAAATTTGTGAAAGATTGACTGGTATTCTTA

ACTATGTTGCTCCTTTTACGCTATGTGGATACGCTGCTTTAATGCCTTTGTATCATGCTATTGCTTC

CCGTATGGCTTTCATTTTCTCCTCCTTGTATAAATCCTGGTTGCTGTCTCTTTATGAGGAGTTGTG

GCCCGTTGTCAGGCAACGTGGCGTGGTGTGCACTGTGTTTGCTGACGCAACCCCCACTGGTTGG

GGCATTGCCACCACCTGTCAGCTCCTTTCCGGGACTTTCGCTTTCCCCCTCCCTATTGCCACGGC

GGAACTCATCGCCGCCTGCCTTGCCCGCTGCTGGACAGGGGCTCGGCTGTTGGGCACTGACAA

TTCCGTGGTGTTGTCGGGGAAGCTGACGTCCTTTCCATGGCTGCTCGCCTGTGTTGCCACCTGG

ATTCTGCGCGGGACGTCCTTCTGCTACGTCCCTTCGGCCCTCAATCCAGCGGACCTTCCTTCCC

GCGGCCTGCTGCCGGCTCTGCGGCCTCTTCCGCGTCTTCGCCTTCGCCCTCAGACGAGTCGGA

TCTCCCTTTGGGCCGCCTCCCCGCATCGGACGCGTGGTACCTTTAAGACCAATGACTTACAAGG

GAGGTGTAGATGTTAGGGAGTTTTTAAAAGAAAAGGGGGGAGTGGAAGGGGTAATTGAGTGGGAA

CGAAGACAAGATCTGCTTTTTGCTTGTACTGGGTCTCTCTGGTTAGACCAGATCTGAGCCTGGGA

GCTCTCTGGCTAACTAGGGAACCCACTGCTTAAGCCTCAATAAAGCTTGCCTTGAGTGCTTCAAG

TAGTGTGTGCCCGTCTGTTGTGTGACTCTGGTAACTAGAGATCCCTCAGACCCTTTTAGTCAGTG

TGGAAAATCTCTAGCAGTAGTAGTTCATGTCATCTTATTATTCAGTATTTATAACTTGCAAAGAAAT

-continued

GAATATCAGAGAGTGAGAGGAACTTGTTTATTGCAGCTTATAATGGTTACAAATAAAGCAATAGCA

TCACAAATTTCACAAATAAAGCATTTTTTTCACTGCATTCTAGTTGTGGTTTGTCCAAACTCATCAA

TGTATCTTATCATGTCTGGCTCTAGCTATCCCGCCCCTAACTCCGCCCATCCCGCCCCTAACTCC

GCCCAGTTCCGCCCATTCTCCGCCCCATGGCTGACTAATTTTTTTTATTTATGCAGAGGCCGAGG

CCGCCTCGGCCTCTGAGCTATTCCAGAAGTAGTGAGGAGGCTTTTTTGGAGGCCTAGGGACGTA

CCCAATTCGCCCTATAGTGAGTCGTATTACGCGCGCTCACTGGCCGTCGTTTTACAACGTCGTGA

CTGGGAAAACCCTGGCGTTACCCAACTTAATCGCCTTGCAGCACATCCCCCTTTCGCCAGCTGG

CGTAATAGCGAAGAGGCCCGCACCGATCGCCCTTCCCAACAGTTGCGCAGCCTGAATGGCGAAT

GGGACGCGCCCTGTAGCGGCGCATTAAGCGCGGCGGGTGTGGTGGTTACGCGCAGCGTGACC

GCTACACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATCGCCCTGATA

GACGGTTTTTCGCCCTTTGACGTTGGAGTCCACGTTCTTTAATAGTGGACTCTTGTTCCAAACTGG

AACAACACTCAACCCTATCTCGGTCTATTCTTTTGATTTATAAGGGATTTTGCCGATTTCGGCCTAT

TGGTTAAAAAATGAGCTGATTTAACAAAAATTTAACGCGAATTTTAACAAAATATTAACGCTTACAA

TTTAGGTGGCACTTTTCGGGGAAATGTGCGCGGAACCCCTATTTGTTTATTTTTCTAAATACATTC

AAATATGTATCCGCTCATGAGACAATAACCCTGATAAATGCTTCAATAATATTGAAAAAGGAAGAG

TATGAGTATTCAACATTTCCGTGTCGCCCTTATTCCCTTTTTTGCGGCATTTTGCCTTCCTGTTTTT

GCTCACCCAGAAACGCTGGTGAAAGTAAAAGATGCTGAAGATCAGTTGGGTGCACGAGTGGGTT

ACATCGAACTGGATCTCAACAGCGGTAAGATCCTTGAGAGTTTTCGCCCCGAAGAACGTTTTCCA

ATGATGAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCACAGAAA

AGCATCTTACGGATGGCATGACAGTAAGAGAATTATGCAGTGCTGCCATAACCATGAGTGATAAC

ACTGCGGCCAACTTACTTCTGACAACGATCGGAGGACCGAAGGAGCTAACCGCTTTTTTGCACAA

CATGGGGGATCATGTAACTCGCCTTGATCGTTGGGAACCGGAGCTGAATGAAGCCATACCAAAC

GACGAGCGTGACACCACGATGCCTGTAGCAATGGCAACAACGTTGCGCAAACTATTAACTGGCG

AACTACTTACTCTAGCTTCCCGGCAACAATTAATAGACTGGATGGAGGCGGATAAAGTTGCAGGA

CCACTTCTGCGCTCGGCCCTTCCGGCTGGCTGGTTTATTGCTGATAAATCTGGAGCCGGTGAGC

GTGGGTCTCGCGGTATCATTGCAGCACTGGGGCCAGATGGTAAGCCCTCCCGTATCGTAGTTAT

CTACACGACGGGGAGTCAGGCAACTATGGATGAACGAAATAGACAGATCGCTGAGATAGGTGCC

TCACTGATTAAGCATTGGTAACTGTCAGACCAAGTTTACTCATATATACTTTAGATTGATTTAAAAC

TTCATTTTTAATTTAAAAGGATCTAGGTGAAGATCCTTTTTGATAATCTCATGACCAAAATCCCTTA

ACGTGAGTTTTCGTTCCACTGAGCGTCAGACCCCGTAGAAAAGATCAAAGGATCTTCTTGAGATC

CTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCA

AATACTGTTCTTCTAGTGTAGCCGTAGTTAGGCCACCACTTCAAGAACTCTGTAGCACCGCCTAC

ATACCTCGCTCTGCTAATCCTGTTACCAGTGGCTGCTGCCAGTGGCGATAAGTCGTGTCTTACCG

GGTTGGACTCAAGACGATAGTTACCGGATAAGGCGCAGCGGTCGGGCTGAACGGGGGGTTCGT

GCACACAGCCCAGCTTGGAGCGAACGACCTACACCGAACTGAGATACCTACAGCGTGAGCTATG

AGAAAGCGCCACGCTTCCCGAAGGGAGAAAGGCGGACAGGTATCCGGTAAGCGGCAGGGTCGG

AACAGGAGAGCGCACGAGGGAGCTTCCAGGGGGAAACGCCTGGTATCTTTATAGTCCTGTCGGG

-continued

TTTCGCCACCTCTGACTTGAGCGTCGATTTTTGTGATGCTCGTCAGGGGGGCGGAGCCTATGGA

AAAACGCCAGCAACGCGGCCTTTTTACGGTTCCTGGCCTTTTGCTGGCCTTTTGCTCACATGTTC

TTTCCTGCGTTATCCCCTGATTCTGTGGATAACCGTATTACCGCCTTTGAGTGAGCTGATACCGCT

CGCCGCAGCCGAACGACCGAGCGCAGCGAGTCAGTGAGCGAGGAAGCGGAAGAGCGCCCAAT

ACGCAAACCGCCTCTCCCCGCGCGTTGGCCGATTCATTAATGCAGCTGGCACGACAGGTTTCCC

GACTGGAAAGCGGGCAGTGAGCGCAACGCAATTAATGTGAGTTAGCTCACTCATTAGGCACCCC

AGGCTTTACACTTTATGCTTCCGGCTCGTATGTTGTGTGGAATTGTGAGCGGATAACAATTTCACA

CAGGAAACAGCTATGACCATGATTACGCCAAGCGCGCAATTAACCCTCACTAAAGGGAACAAAAG

CTGGAGCTGCAAGCTT pSSI12112 (SEQ ID NO: 3):
AATGTAGTCTTATGCAATACTCTTGTAGTCTTGCAACATGGTAACGATGAGTTAGCAACATGCCTT

ACAAGGAGAGAAAAAGCACCGTGCATGCCGATTGGTGGAAGTAAGGTGGTACGATCGTGCCTTA

TTAGGAAGGCAACAGACGGGTCTGACATGGATTGGACGAACCACTGAATTGCCGCATTGCAGAG

ATATTGTATTTAAGTGCCTAGCTCGATACATAAACGGGTCTCTCTGGTTAGACCAGATCTGAGCCT

GGGAGCTCTCTGGCTAACTAGGGAACCCACTGCTTAAGCCTCAATAAAGCTTGCCTTGAGTGCTT

CAAGTAGTGTGTGCCCGTCTGTTGTGTGACTCTGGTAACTAGAGATCCCTCAGACCCTTTTAGTC

AGTGTGGAAAATCTCTAGCAGTGGCGCCCGAACAGGGACTTGAAAGCGAAAGGGAAACCAGAGG

AGCTCTCTCGACGCAGGACTCGGCTTGCTGAAGCGCGCACGGCAAGAGGCGAGGGGCGGCGA

CTGGTGAGTACGCCAAAAATTTTGACTAGCGGAGGCTAGAAGGAGAGAGATGGGTGCGAGAGCG

TCAGTATTAAGCGGGGGAGAATTAGATCGCGATGGGAAAAAATTCGGTTAAGGCCAGGGGGAAA

GAAAAAATATAAATTAAAACATATAGTATGGGCAAGCAGGGAGCTAGAACGATTCGCAGTTAATCC

TGGCCTGTTAGAAACATCAGAAGGCTGTAGACAAATACTGGGACAGCTACAACCATCCCTTCAGA

CAGGATCAGAAGAACTTAGATCATTATATAATACAGTAGCAACCCTCTATTGTGTGCATCAAAGGA

TAGAGATAAAAGACACCAAGGAAGCTTTAGACAAGATAGAGGAAGAGCAAAACAAAAGTAAGACC

ACCGCACAGCAAGCGGCCGCTGATCTTCAGACCTGGAGGAGGAGATATGAGGGACAATTGGAG

AAGTGAATTATATAAATATAAAGTAGTAAAAATTGAACCATTAGGAGTAGCACCCACCAAGGCAAA

GAGAAGAGTGGTGCAGAGAGAAAAAAGAGCAGTGGGAATAGGAGCTTTGTTCCTTGGGTTCTTG

GGAGCAGCAGGAAGCACTATGGGCGCAGCGTCAATGACGCTGACGGTACAGGCCAGACAATTAT

TGTCTGGTATAGTGCAGCAGCAGAACAATTTGCTGAGGGCTATTGAGGCGCAACAGCATCTGTTG

CAACTCACAGTCTGGGGCATCAAGCAGCTCCAGGCAAGAATCCTGGCTGTGGAAAGATACCTAA

AGGATCAACAGCTCCTGGGGATTTGGGGTTGCTCTGGAAAACTCATTTGCACCACTGCTGTGCCT

TGGAATGCTAGTTGGAGTAATAAATCTCTGGAACAGATTTGGAATCACACGACCTGGATGGAGTG

GGACAGAGAAATTAACAATTACACAAGCTTAATACACTCCTTAATTGAAGAATCGCAAAACCAGCA

AGAAAAGAATGAACAAGAATTATTGGAATTAGATAAATGGGCAAGTTTGTGGAATTGGTTTAACAT

AACAAATTGGCTGTGGTATATAAAATTATTCATAATGATAGTAGGAGGCTTGGTAGGTTTAAGAAT

AGTTTTTGCTGTACTTTCTATAGTGAATAGAGTTAGGCAGGGATATTCACCATTATCGTTTCAGAC

CCACCTCCCAACCCCGAGGGGACCCGACAGGCCCGAAGGAATAGAAGAAGAAGGTGGAGAGAG

AGACAGAGACAGATCCATTCGATTAGTGAACGGATCTCGACGGTATCGATACTAGTAATTTTTCTG

CAGAAAACGTACCCGGGGATCCTCTAGGATCCCACCGAAAGGTTGCTCCTTAACACAGGCTAAG

GACCAGCTTCTTTGGGAGAGAACAGACGCAGGGGCGGGAGGGAAAAAGGGAGAGGCAGACGTC

ACTTCCCCTTGGCGGCTCTGGCAGCAGATTGGTCGGTTGAGTGGCAGAAAGGCAGACGGGGAC

TGGGCAAGGCACTGTCGGTGACATCACGGACAGGGCGACTTCTATGTAGATGAGGCAGCGCAG

AGGCTGCTGCTTCGCCACTTGCTGCTTCGCCACGAAGGAGTTCCCGTGCCCTGGGAGCGGGTTC

AGGACCGCGGATCGGAAGTGAGAATCCCAGCTGTGTGTCAGGGCTGGAAAGGGCTCGGGAGTG

CGCGGGGCAAGTGACCGTGTGTGTAAAGAGTGAGGCGTATGAGGCTGTGTCGGGGCAGAGCCC

GAAGATCCGGGTTGCGGAGGGTGGGCCTGGGAGGGGTGGTGGCCATTTTTTGTCTAACCCTAAC

TGAGAAGGGCGTAGGCGCCGTGCTTTTGCTCCCCGCGCGCTGTTTTTCTCGCTGACTTTCAGCG

GGCGGAAAAGCCTCGGCCTGCCGCCTTCCACCGTTCATTCTAGAGCAAACAAAAAATGTCAGCT

GCTGGCCCGTTCGCCCCTCCCGGGGACCTGCGGCGGGTCGCCTGCCCAGCCCCCGAACCCCG

CCTGGAGGCCGCGGTCGGCCCGGGGCTTCTCCGGAGGCACCCACTGCCACCGCGAAGAGTTG

GGCTCTGTCAGCCGCGGGTCTCTCGGGGGCGAGGGCGAGGTTCAGGCCTTTCAGGCCGCAGG

AAGAGGAACGGAGCGAGTCCCCGCGCGCGGCGCGATTCCCTGAGCTGTGGGACGTGCACCCA

GGACTCGGCTCACACATGCAGTTCGCTTTCCTGTTGGTGGGGGGAACGCCGATCGTGCGCATCC

GTCACCCCTCGCCGGCAATGGGGGCTTGTGAACCCCCAAACCTGACTGACTGGGCCAGTGTGCT

GCAAATTGGCAGGAGACGTGAAGGCACCTCCAAAGTCGACTTTCTGGAGTTTCAAAAACAGACC

GTACATGTCCGCGGTCGCGACGTACCTACCGGGTAGGGGAGGCGCTTTTCCCAAGGCAGTCTG

GAGCATGCGCTTTAGCAGCCCCGCTGGGCACTTGGCGCTACACAAGTGGCCTCTGGCCTCGCA

CACATTCCACATCCACCGGTAGGCGCCAACCGGCTCCGTTCTTTGGTGGCCCCTTCGCGCCACC

TTCTACTCCTCCCCTAGTCAGGAAGTTCCCCCCCGCCCCGCAGCTCGCGTCGTGCAGGACGTGA

CAAATGGAAGTAGCACGTCTCACTAGTCTCGTGCAGATGGACAGCACCGCTGAGCAATGGAAGC

GGGTAGGCCTTTGGGGCAGCGGCCAATAGCAGCTTTGCTCCTTCGCTTTCTGGGCTCAGAGGCT

GGGAAGGGGTGGGTCCGGGGGCGGGCTCAGGGGCGGGCTCAGGGGCGGGGCGGGCGCCCG

AAGTCCTCCGGAGGCCCGGCATTCTGCACGCTTCAAAAGCGCACGTCTGCCGCGCTGTTCTCCT

CTTCCTCATCTCCGGGCCTTTCGACTCTAGACACGTGTTGACAATTAATCATCGGCATAGTATATC

GGCATAGTATAATACGACAAGGTGAGGAACTAAACCATGGCCAAGCCTTTGTCTCAAGAAGAATC

CACCCTCATTGAAAGAGCAACGGCTACAATCAACAGCATCCCCATCTCTGAAGACTACAGCGTCG

CCAGCGCAGCTCTCTCTAGCGACGGCCGCATCTTCACTGGTGTCAATGTATATCATTTTACTGGG

GGACCTTGTGCAGAACTCGTGGTGCTGGGCACTGCTGCTGCTGCGGCAGCTGGCAACCTGACTT

GTATCGTCGCGATCGGAAATGAGAACAGGGGCATCTTGAGCCCCTGCGGACGGTGCCGACAGG

TGCTTCTCGATCTGCATCCTGGGATCAAAGCCATAGTGAAGGACAGTGATGGACAGCCGACGGC

AGTTGGGATTCGTGAATTGCTGCCCTCTGGTTATGTGTGGGAGGGCTAAGCACAATTCGAGCTC

GGTACGCGTATCGATGGCGCCAGCTGCAGGCGGCCGCCATATGCATCCTAGGCCTATTAATATT

CCGGAGTATACGTAGCCGGCTAACGTTAACAACCGGTACGATGCATTAGTTATTAATAGTAATCAA

TTACGGGGTCATTAGTTCATAGCCCATATATGGAGTTCCGCGTTACATAACTTACGGTAAATGGCC

CGCCTGGCTGACCGCCCAACGACCCCCGCCCATTGACGTCAATAATGACGTATGTTCCCATAGT

AACGCCAATAGGGACTTTCCATTGACGTCAATGGGTGGAGTATTTACGGTAAACTGCCCACTTGG

CAGTACATCAAGTGTATCATATGCCAAGTACGCCCCCTATTGACGTCAATGACGGTAAATGGCCC

GCCTGGCATTATGCCCAGTACATGACCTTATGGGACTTTCCTACTTGGCAGTACATCTACGTATTA

GTCATCGCTATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGCACCAAAATC

AACGGGACTTTCCAAAATGTCGTAACAACTCCGCCCCATTGACGCAAATGGGCGGTAGGCGTGT

-continued

```
ACGGTGGGAGGTCTATATAAGCAGAGCTGGTTTAGTGAACCGTCAGATCCGCTAGCCCCACCAT

GCCGCGCGCTCCCCGCTGCCGAGCCGTGCGCTCCCTGCTGCGCAGCCACTACCGCGAGGTGCT

GCCGCTGGCCACGTTCGTGCGGCGCCTGGGGCCCCAGGGCTGGCGGCTGGTGCAGCGCGGG

GACCCGGCGGCTTTCCGCGCGCTGGTGGCCCAGTGCCTGGTGTGCGTGCCCTGGGACGCACG

GCCGCCCCCCGCCGCCCCCTCCTTCCGCCAGGTGTCCTGCCTGAAGGAGCTGGTGGCCCGAGT

GCTGCAGAGGCTGTGCGAGCGCGGCGCGAAGAACGTGCTGGCCTTCGGCTTCGCGCTGCTGGA

CGGGGCCCGCGGGGGCCCCCCCGAGGCCTTCACCACCAGCGTGCGCAGCTACCTGCCCAACA

CGGTGACCGACGCACTGCGGGGGAGCGGGGCGTGGGGGCTGCTGTTGCGCCGCGTGGGCGA

CGACGTGCTGGTTCACCTGCTGGCACGCTGCGCGCTCTTTGTGCTGGTGGCTCCCAGCTGCGC

CTACCAGGTGTGCGGGCCGCCGCTGTACCAGCTCGGCGCTGCCACTCAGGCCCGGCCCCCGC

CACACGCTAGTGGACCCCGAAGGCGTCTGGGATGCGAACGGGCCTGGAACCATAGCGTCAGGG

AGGCCGGGGTCCCCCTGGGCCTGCCAGCCCCGGGTGCGAGGAGGCGCGGGGGCAGTGCCAG

CCGAAGTCTGCCGTTGCCCAAGAGGCCCAGGCGTGGCGCTGCCCCTGAGCCGGAGCGGACGC

CCGTTGGGCAGGGGTCCTGGGCCCACCCGGGCAGGACGCGTGGACCGAGTGACCGTGGTTTCT

GTGTGGTGTCACCTGCCAGACCCGCCGAAGAAGCCACCTCTTTGGAGGGTGCGCTCTCTGGCAC

GCGCCACTCCCACCCATCCGTGGGCCGCCAGCACCACGCGGGCCCCCCATCCACATCGCGGCC

ACCACGTCCCTGGGACACGCCTTGTCCCCCGGTGTACGCCGAGACCAAGCACTTCCTCTACTCC

TCAGGCGACAAGGAGCAGCTGCGGCCCTCCTTCCTACTCAGCTCTCTGAGGCCCAGCCTGACTG

GCGCTCGGAGGCTCGTGGAGACCATCTTTCTGGGTTCCAGGCCCTGGATGCCAGGGACTCCCC

GCAGGTTGCCCCGCCTGCCCCAGCGCTACTGGCAAATGCGGCCCCTGTTTCTGGAGCTGCTTG

GGAACCACGCGCAGTGCCCCTACGGGGTGCTCCTCAAGACGCACTGCCCGCTGCGAGCTGCGG

TCACCCCAGCAGCCGGTGTCTGTGCCCGGGAGAAGCCCCAGGGCTCTGTGGCGGCCCCCGAG

GAGGAGGACACAGACCCCCGTCGCCTGGTGCAGCTGCTCCGCCAGCACAGCAGCCCCTGGCAG

GTGTACGGCTTCGTGCGGGCCTGCCTGCGCCGGCTGGTGCCCCCAGGCCTCTGGGGCTCCAG

GCACAACGAACGCCGCTTCCTCAGGAACACCAAGAAGTTCATCTCCCTGGGGAAGCATGCCAAG

CTCTCGCTGCAGGAGCTGACGTGGAAGATGAGCGTGCGGGGCTGCGCTTGGCTGCGCAGGAGC

CCAGGGGTTGGCTGTGTTCCGGCCGCAGAGCACCGTCTGCGTGAGGAGATCCTGGCCAAGTTC

CTGCACTGGCTGATGAGTGTGTACGTCGTCGAGCTGCTCAGGTCTTTCTTTTATGTCACGGAGAC

CACGTTTCAAAAGAACAGGCTCTTTTTCTACCGGAAGAGTGTCTGGAGCAAGTTGCAAAGCATTG

GAATCAGACAGCACTTGAAGAGGGTGCAGCTGCGGGAGCTGTCGGAAGCAGAGGTCAGGCAGC

ATCGGGAAGCCAGGCCCGCCCTGCTGACGTCCAGACTCCGCTTCATCCCCAAGCCTGACGGGC

TGCGGCCGATTGTGAACATGGACTACGTCGTGGGAGCCAGAACGTTCCGCAGAGAAAAGAGGG

CCGAGCGTCTCACCTCCAGGGTGAAGGCACTGTTCAGCGTGCTCAACTACGAGCGGGCGCGGC

GCCCCGGCCTCCTGGGCGCCTCTGTGCTGGGCCTGGACGATATCCACAGGGCCTGGCGCACCT

TCGTGCTGCGTGTGCGGGCCCAGGACCCGCCGCCTGAGCTGTACTTTGTCAAGGTGGATGTGA

CGGGCGCGTACGACACCATCCCCCAGGACAGGCTCACGGAGGTCATCGCCAGCATCATCAAAC

CCCAGAACACGTACTGCGTGCGTCGGTATGCCGTGGTCCAGAAGGCCGCCCATGGGCACGTCC

GCAAGGCCTTCAAGAGCCACGTCTCTACCTTGACAGACCTCCAGCCGTACATGCGACAGTTCGT

GGCTCACCTGCAGGAGACCAGCCCGCTGAGGGATGCCGTCGTCATCGAGCAGAGCTCCTCCCT

GAATGAGGCCAGCAGTGGCCTCTTCGACGTCTTCCTACGCTTCATGTGCCACCACGCCGTGCGC

ATCAGGGGCAAGTCCTACGTCCAGTGCCAGGGGATCCCGCAGGGCTCCATCCTCTCCACGCTG
```

-continued

CTCTGCAGCCTGTGCTACGGCGACATGGAGAACAAGCTGTTTGCGGGGATTCGGCGGGACGGG

CTGCTCCTGCGTTTGGTGGATGATTTCTTGTTGGTGACACCTCACCTCACCCACGCGAAAACCTT

CCTCAGGACCCTGGTCCGAGGTGTCCCTGAGTATGGCTGCGTGGTGAACTTGCGGAAGACAGTG

GTGAACTTCCCTGTAGAAGACGAGGCCCTGGGTGGCACGGCTTTTGTTCAGATGCCGGCCCACG

GCCTATTCCCCTGGTGCGGCCTGCTGCTGGATACCCGGACCCTGGAGGTGCAGAGCGACTACT

CCAGCTATGCCCGGACCTCCATCAGAGCCAGTCTCACCTTCAACCGCGGCTTCAAGGCTGGGAG

GAACATGCGTCGCAAACTCTTTGGGGTCTTGCGGCTGAAGTGTCACAGCCTGTTTCTGGATTTGC

AGGTGAACAGCCTCCAGACGGTGTGCACCAACATCTACAAGATCCTCCTGCTGCAGGCGTACAG

GTTTCACGCATGTGTGCTGCAGCTCCCATTTCATCAGCAAGTTTGGAAGAACCCCACATTTTTCCT

GCGCGTCATCTCTGACACGGCCTCCCTCTGCTACTCCATCCTGAAAGCCAAGAACGCAGGGATG

TCGCTGGGGGCCAAGGGCGCCGCCGGCCCTCTGCCCTCCGAGGCCGTGCAGTGGCTGTGCCA

CCAAGCATTCCTGCTCAAGCTGACTCGACACCGTGTCACCTACGTGCCACTCCTGGGGTCACTC

AGGACAGCCCAGACGCAGCTGAGTCGGAAGCTCCCGGGGACGACGCTGACTGCCCTGGAGGC

CGCAGCCAACCCGGCACTGCCCTCAGACTTCAAGACCATCCTGGACTGAGTCGAAACTCGCGGC

CGCATGCGTCGACGCGTATCGATGCATCTTAAGTAGATGTACCTTTAAGACCAATGACTTACAAG

GCAGCTGTAGATCTTAGCCACTTTTTAAAAGAAAAGGGGGGACTGGAAGGGCTAATTCACTCCCA

ACGAAGACAAGATCTGCTTTTTGCTTGTACTGGGTCTCTCTGGTTAGACCAGATCTGAGCCTGGG

AGCTCTCTGGCTAACTAGGGAACCCACTGCTTAAGCCTCAATAAAGCTTGCCTTGAGTGCTTCAA

GTAGTGTGTGCCCGTCTGTTGTGTGACTCTGGTAACTAGAGATCCCTCAGACCCTTTTAGTCAGT

GTGGAAAATCTCTAGCAGTAGTAGTTCATGTCATCTTATTATTCAGTATTTATAACTTGCAAAGAAA

TGAATATCAGAGAGTGAGAGGAACTTGTTTATTGCAGCTTATAATGGTTACAAATAAAGCAATAGC

ATCACAAATTTCACAAATAAAGCATTTTTTTCACTGCATTCTAGTTGTGGTTTGTCCAAACTCATCA

ATGTATCTTATCATGTCTGGCTCTAGCTATCCCGCCCCTAACTCCGCCCATCCCGCCCCTAACTC

CGCCCAGTTCCGCCCATTCTCCGCCCCATGGCTGACTAATTTTTTTTATTTATGCAGAGGCCGAG

GCCGCCTCGGCCTCTGAGCTATTCCAGAAGTAGTGAGGAGGCTTTTTTGGAGGCCTAGGGACGT

ACCCAATTCGCCCTATAGTGAGTCGTATTACGCGCGCTCACTGGCCGTCGTTTTACAACGTCGTG

ACTGGGAAAACCCTGGCGTTACCCAACTTAATCGCCTTGCAGCACATCCCCCTTTCGCCAGCTGG

CGTAATAGCGAAGAGGCCCGCACCGATCGCCCTTCCCAACAGTTGCGCAGCCTGAATGGCGAAT

GGGACGCGCCCTGTAGCGGCGCATTAAGCGCGGCGGGTGTGGTGGTTACGCGCAGCGTGACC

GCTACACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATCGCCCTGATA

GACGGTTTTTCGCCCTTTGACGTTGGAGTCCACGTTCTTTAATAGTGGACTCTTGTTCCAAACTGG

AACAACACTCAACCCTATCTCGGTCTATTCTTTTGATTTATAAGGGATTTTGCCGATTTCGGCCTAT

TGGTTAAAAAATGAGCTGATTTAACAAAAATTTAACGCGAATTTTAACAAAATATTAACGCTTACAA

TTTAGGTGGCACTTTTCGGGGAAATGTGCGCGGAACCCCTATTTGTTTATTTTTCTAAATACATTC

AAATATGTATCCGCTCATGAGACAATAACCCTGATAAATGCTTCAATAATATTGAAAAAGGAAGAG

-continued

```
TATGAGTATTCAACATTTCCGTGTCGCCCTTATTCCCTTTTTTGCGGCATTTTGCCTTCCTGTTTTT

GCTCACCCAGAAACGCTGGTGAAAGTAAAAGATGCTGAAGATCAGTTGGGTGCACGAGTGGGTT

ACATCGAACTGGATCTCAACAGCGGTAAGATCCTTGAGAGTTTTCGCCCCGAAGAACGTTTTCCA

ATGATGAGCACTTTTAAAGTTCTGCTATGTGGCGCGGTATTATCCCGTATTGACGCCGGGCAAGA

GCAACTCGGTCGCCGCATACACTATTCTCAGAATGACTTGGTTGAGTACTCACCAGTCACAGAAA

AGCATCTTACGGATGGCATGACAGTAAGAGAATTATGCAGTGCTGCCATAACCATGAGTGATAAC

ACTGCGGCCAACTTACTTCTGACAACGATCGGAGGACCGAAGGAGCTAACCGCTTTTTTGCACAA

CATGGGGGATCATGTAACTCGCCTTGATCGTTGGGAACCGGAGCTGAATGAAGCCATACCAAAC

GACGAGCGTGACACCACGATGCCTGTAGCAATGGCAACAACGTTGCGCAAACTATTAACTGGCG

AACTACTTACTCTAGCTTCCCGGCAACAATTAATAGACTGGATGGAGGCGGATAAAGTTGCAGGA

CCACTTCTGCGCTCGGCCCTTCCGGCTGGCTGGTTTATTGCTGATAAATCTGGAGCCGGTGAGC

GTGGGTCTCGCGGTATCATTGCAGCACTGGGGCCAGATGGTAAGCCCTCCCGTATCGTAGTTAT

CTACACGACGGGGAGTCAGGCAACTATGGATGAACGAAATAGACAGATCGCTGAGATAGGTGCC

TCACTGATTAAGCATTGGTAACTGTCAGACCAAGTTTACTCATATATACTTTAGATTGATTTAAAAC

TTCATTTTTAATTTAAAAGGATCTAGGTGAAGATCCTTTTTGATAATCTCATGACCAAAATCCCTTA

ACGTGAGTTTTCGTTCCACTGAGCGTCAGACCCCGTAGAAAAGATCAAAGGATCTTCTTGAGATC

CTTTTTTTCTGCGCGTAATCTGCTGCTTGCAAACAAAAAAACCACCGCTACCAGCGGTGGTTTGTT

TGCCGGATCAAGAGCTACCAACTCTTTTTCCGAAGGTAACTGGCTTCAGCAGAGCGCAGATACCA

AATACTGTTCTTCTAGTGTAGCCGTAGTTAGGCCACCACTTCAAGAACTCTGTAGCACCGCCTAC

ATACCTCGCTCTGCTAATCCTGTTACCAGTGGCTGCTGCCAGTGGCGATAAGTCGTGTCTTACCG

GGTTGGACTCAAGACGATAGTTACCGGATAAGGCGCAGCGGTCGGGCTGAACGGGGGGTTCGT

GCACACAGCCCAGCTTGGAGCGAACGACCTACACCGAACTGAGATACCTACAGCGTGAGCTATG

AGAAAGCGCCACGCTTCCCGAAGGGAGAAAGGCGGACAGGTATCCGGTAAGCGGCAGGGTCGG

AACAGGAGAGCGCACGAGGGAGCTTCCAGGGGGAAACGCCTGGTATCTTTATAGTCCTGTCGGG

TTTCGCCACCTCTGACTTGAGCGTCGATTTTTGTGATGCTCGTCAGGGGGGCGGAGCCTATGGA

AAAACGCCAGCAACGCGGCCTTTTTACGGTTCCTGGCCTTTTGCTGGCCTTTTGCTCACATGTTC

TTTCCTGCGTTATCCCCTGATTCTGTGGATAACCGTATTACCGCCTTTGAGTGAGCTGATACCGCT

CGCCGCAGCCGAACGACCGAGCGCAGCGAGTCAGTGAGCGAGGAAGCGGAAGAGCGCCCAAT

ACGCAAACCGCCTCTCCCCGCGCGTTGGCCGATTCATTAATGCAGCTGGCACGACAGGTTTCCC

GACTGGAAAGCGGGCAGTGAGCGCAACGCAATTAATGTGAGTTAGCTCACTCATTAGGCACCCC

AGGCTTTACACTTTATGCTTCCGGCTCGTATGTTGTGTGGAATTGTGAGCGGATAACAATTTCACA

CAGGAAACAGCTATGACCATGATTACGCCAAGCGCGCAATTAACCCTCACTAAAGGGAACAAAAG

CTGGAGCTGCAAGCTT
```

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating an age-related disorder in a mammalian subject, the method comprising administering to the subject a nucleic acid viral vector comprising a coding sequence for telomerase reverse transcriptase (TERT) and a coding sequence for telomerase RNA TR to express functional telomerase in the subject.

2. The method of claim 1, wherein the coding sequence for TERT is human TERT, or an active fragment or functional equivalent of human TERT having at least 80% or more sequence identity to human TERT.

3. The method of claim 1, wherein the nucleic acid sequence encoding TERT is operably linked to a regulatory sequence that drives expression of the coding sequence.

4. The method of claim 3, wherein the vector is a non-integrative vector.

5. The method of claim 3, wherein the vector is an adeno-associated virus-based vector.

6. The method of claim 3, wherein the vector is a lentivirus-based vector.

7. The method of claim 1, wherein the vector is represented by one of the following formulae:

LITR-U1-TR-CMV-TERT-SV40pA-RITR

LTR-U1-TR-PGK-BSD-CMV-TERT-LTR or an active fragment or functional equivalent thereof.

8. The method of claim 7, wherein the vector is selected from pSSI14342, and pSSI12112.

9. The method of claim 1, wherein the subject is healthy and free of chronic illness.

10. The method of claim 9, wherein the subject is an aged adult mammal.

11. The method of claim 9, wherein the subject is human.

12. The method of claim 9, wherein the subject is an animal selected from cat, dog and horse.

13. The method of claim 1, wherein the age-related disorder is selected from the group consisting of osteoporosis, arthrosis, glucose intolerance, insulin resistant, reduced heart, circulatory and/or lung function, cardiovascular disease, loss of memory, loss of neuromuscular coordination and decrease of longevity, or combinations thereof.

14. The method of claim 13, wherein the method elicits an increase in lifespan in the subject.

15. A method of expressing a functional TERT protein in a mammalian cell, the method comprising:

contacting the cell with a lentivirus-based nucleic acid vector comprising a coding sequence for telomerase reverse transcriptase (TERT) and a coding sequence for telomerase RNA (TR);

to express functional TERT in the cell without toxicity to the cell.

16. The method of claim 15, wherein the vector is represented by the formula: LTR-U1-TR-PGK-BSD-CMV-TERT-LTR; or an active fragment or functional equivalent thereof.

17. The method of claim 16, wherein the vector is pSSI12112.

18. The method of claim 15, wherein the cell is human.

19. The method of claim 15, wherein the cell is an animal cell selected from cat, dog and horse.

* * * * *